United States Patent
García Antón et al.

(10) Patent No.: US 9,266,921 B2
(45) Date of Patent: Feb. 23, 2016

(54) PGC-1α-MODULATING PEPTIDES

(75) Inventors: José María García Antón, Barcelona (ES); Nuria Almiñana Domenech, Barcelona (ES); Antonio Vicente Ferrer Montiel, Alicante (ES)

(73) Assignee: Lipotec, S.A., Gava, Barcelona (ES)

( * ) Notice: Subject to any disclaimer, the term of this patent is extended or adjusted under 35 U.S.C. 154(b) by 69 days.

(21) Appl. No.: 14/006,981

(22) PCT Filed: Mar. 23, 2012

(86) PCT No.: PCT/EP2012/055259
§ 371 (c)(1),
(2), (4) Date: Dec. 9, 2013

(87) PCT Pub. No.: WO2012/130775
PCT Pub. Date: Oct. 4, 2012

(65) Prior Publication Data
US 2014/0086981 A1    Mar. 27, 2014

Related U.S. Application Data

(60) Provisional application No. 61/467,648, filed on Mar. 25, 2011.

(30) Foreign Application Priority Data

Mar. 25, 2011    (ES) .................................. 201130439

(51) Int. Cl.
| | | |
|---|---|---|
| *A61K 38/00* | (2006.01) | |
| *A61K 38/08* | (2006.01) | |
| *A61K 38/28* | (2006.01) | |
| *A61P 3/10* | (2006.01) | |
| *A61P 7/12* | (2006.01) | |
| *A61P 9/12* | (2006.01) | |
| *A61P 25/28* | (2006.01) | |
| *C07K 14/47* | (2006.01) | |
| *C07K 7/06* | (2006.01) | |
| *A61K 36/896* | (2006.01) | |
| *A61K 38/01* | (2006.01) | |
| *A61K 38/06* | (2006.01) | |
| *A61K 38/07* | (2006.01) | |
| *A61K 36/23* | (2006.01) | |
| *A61K 36/25* | (2006.01) | |
| *A61K 36/53* | (2006.01) | |
| *A61K 36/736* | (2006.01) | |
| *A61K 36/74* | (2006.01) | |

(52) U.S. Cl.
CPC . *C07K 7/06* (2013.01); *A61K 36/23* (2013.01); *A61K 36/25* (2013.01); *A61K 36/53* (2013.01); *A61K 36/736* (2013.01); *A61K 36/74* (2013.01); *A61K 36/896* (2013.01); *A61K 38/011* (2013.01); *A61K 38/06* (2013.01); *A61K 38/07* (2013.01); *A61K 38/08* (2013.01); *A61K 38/00* (2013.01)

(58) Field of Classification Search
CPC ........................................................ C07K 7/06
See application file for complete search history.

(56) References Cited

U.S. PATENT DOCUMENTS

| | | | |
|---|---|---|---|
| 5,348,943 | A | 9/1994 | Pickart |
| 6,403,656 | B1 | 6/2002 | Rivier et al. |
| 7,410,658 | B2 | 8/2008 | Wang et al. |
| 7,618,662 | B2 | 11/2009 | Hines et al. |
| 2002/0160064 | A1 | 10/2002 | Zulli et al. |
| 2003/0044475 | A1 | 3/2003 | Van De Wiel et al. |
| 2004/0152746 | A1 | 8/2004 | Bardsley et al. |
| 2006/0035849 | A1 | 2/2006 | Spiegelman et al. |
| 2008/0182780 | A1 | 7/2008 | Linge et al. |
| 2009/0005341 | A1 | 1/2009 | Oreste et al. |
| 2009/0029933 | A1 | 1/2009 | Velloso et al. |
| 2010/0184721 | A1 | 7/2010 | Choulot et al. |
| 2011/0129546 | A1 | 6/2011 | Umbert Mill |

FOREIGN PATENT DOCUMENTS

| | | |
|---|---|---|
| DE | 202009010648 | 1/2010 |
| EP | 1041977 B1 | 10/2000 |
| EP | 1234572 A1 | 8/2002 |
| EP | 1331934 B1 | 8/2003 |
| EP | 1781297 B1 | 5/2007 |
| EP | 2046283 A2 | 4/2009 |
| EP | 2210610 A1 | 7/2010 |
| WO | WO 95/35108 A1 | 12/1995 |
| WO | WO 02/32938 A2 | 4/2002 |
| WO | WO 02/38150 | 5/2002 |
| WO | WO 2009/153373 | 12/2009 |
| WO | WO 2010/089421 A2 | 8/2010 |

OTHER PUBLICATIONS

Yamaguchi et al, Development of a Substrate-Based Cyclic Phosphopeptide Inhibitor of Protein Phosphatase 2Cä, Wip1, Biochemistry 2006, 45, 13193-13202.*

(Continued)

*Primary Examiner* — Karlheinz R Skowronek
*Assistant Examiner* — Sergio Coffa
(74) *Attorney, Agent, or Firm* — Fay Sharpe LLP

(57) ABSTRACT

Peptides of general formula (I): $R_1-W_n-X_m\text{-}AA_1\text{-}AA_2\text{-}AA_3\text{-}AA_4\text{-}AA_5\text{-}AA_6\text{-}Y_p-Z_q-R_2$ their stereoisomers, mixtures thereof and/or their cosmetically or pharmaceutically acceptable salts, a preparation process, cosmetic or pharmaceutical compositions which contain them and their use in the treatment and/or care of conditions, disorders and/or diseases which improve or are prevented by PGC-1α modulation.

$$R_1-W_n-X_m\text{-}AA_1\text{-}AA_2\text{-}AA_3\text{-}AA_4\text{-}AA_5\text{-}AA_6\text{-}Y_p-Z_q-R_2 \quad (I)$$

17 Claims, No Drawings

(56) References Cited

OTHER PUBLICATIONS

Liang et al, PGC-1__: a key regulator of energy metabolism, Advan in Physiol Edu 30:145-151, 2006.*

Anderson et al, PGC-1α in aging and anti-aging interventions, Biochimica et Biophysica Acta 1790 (2009) 1059-1066.*

IUPAC-IUB Joint Commission on Biochemical Nomenclature (JCBN), Nomenclature and Symbolism for Amino Acids and Peptides, Recommendations 1983, in Eur. J. Biochem. 138, pp. 9-37 (1984).

Yamaguchi, et al. "Development of a Substrate-based cyclic phosphopeptide inhibitor of protein phosphate" Biochemistry, vol. 45, No. 44, Jan. 1, 2006, pp. 13193-13202.

Tontonoz, et al. "Regulation of adipocyte gene expression and differentiation by peroxisome proliferator activated receptor gamma" Curr. Opin. Genet. Dev., 5(5), 1995, pp. 571-576.

Jones, et al. "Deletion of PPARgamma in adipose tissues of mice protects against high fat diet-induced obesity and insulin resistance" Proc. Natl. Acad. Sci. U.S.A., 2005, 102(17), pp. 6207-6212.

Tontonoz, et al. "Stimulation of adipogenesis in fibroblasts by PPARγ2, a lipid-activated transcription factor" Cell, 1994, vol. 79, pp. 7355-7359.

Okuno, et al. "Troglitazone increases the Number of small adipocytes without the change of white adipose tissue mass in obese Zucker rats" J. Clin. Invest., 1998, vol. 101, pp. 1354-1361.

Ristow, et al. "Obesity associated with a mutation in a genetic regulator of adipocyte differentiation" N. Engl. J. Med., 1998, vol. 339, pp. 953-959.

Classon, et al. "Opposing roles of pRB and p107 in adipocyte differentiation" P.N.A.S., 2000, vol. 97, pp. 10826-10831.

Krentz, et al. "Type 2 diabetes, psoriasis and thiazolidinediones" Int. J. Clin. Pract., 2006, vol. 60, pp. 362-363.

Handschin, et al. "Peroxisome proliferator-activated receptor gamma coactivator 1 coactivators, energy homeostasis, and metabolism" Endocr. Rev., 2006, 27(7):728-735.

Semple, et al. "Expression of the thermogenic nuclear hormone receptor coactivator PGC-1α is reduced in the adipose tissue of morbidly obese subjects" Int. J. Obes., 2004, vol. 28, pp. 176-179.

Terranova, et al. "Cellulite: nature and aetiopathogenesis" Int. J. Cosmet. Sci., 2006, vol. 28(3), pp. 157-167.

Berge, et al. "Pharmaceutical salts" J. Pharm. Sci., 1977, vol. 66, pp. 1-19.

Kullmann, W. "Proteases as catalysts for enzymic syntheses of opioid peptides" J. Biol. Chem., 1980, vol. 255, pp. 8234-8238.

Lloyd-Williams, et al. "Convergent solid-phase peptide synthesis" Tetrahedron, 1993, vol. 49, pp. 11065-11133.

Matsueda, et al. "A p-methylbenzhydrylamine resin for improved solid-phase synthesis of peptide amides" Peptides, 1981, vol. 2, pp. 45-50.

Albericio, et al. "Preparation and application of the 5-(4-(9-fluorenylmethyloxycarbonyl) aminomethyl-3, 5-dimethoxyphenoxy)valeric acid (PAL) handle for the solid-phase synthesis of C-terminal peptide amides under mild conditions" J. Org. Chem., 1990, vol. 55, pp. 3730-3743.

Rink, H., "Solid-phase synthesis of protected peptide fragments using a trialkoxy-diphenyl-methylester resin" Tetrahedron Lett., 1987, vol. 28, pp. 3787-3790.

Nelson, G. "Application of microencapsulation in textiles" Int. J. Pharm., 2002, vol. 242, pp. 55-62.

Malcom, et al. "Controlled release of a model antibacterial drug from a novel self-lubricating silicone biomaterial" J. Cont. Release, 2004, vol. 97, pp. 313-320.

Quatresooz, et al. "Cellulite histopathology and related mechanobiology", Int. J. Cosm. Sci., 2006, vol. 28, pp. 207-210.

* cited by examiner

SEQUENCE LISTING

```
<160> NUMBER OF SEQ ID NOS: 71

<210> SEQ ID NO 1
<211> LENGTH: 6
<212> TYPE: PRT
<213> ORGANISM: Artificial Sequence
<220> FEATURE:
<223> OTHER INFORMATION: Synthetic peptide

<400> SEQUENCE: 1

Ser Ile Tyr Val Ala Thr
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic peptide

<400> SEQUENCE: 2

Ser Val Val Val Arg Thr
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic peptide

<400> SEQUENCE: 3

His Ile Tyr Val Ala Thr
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic peptide
```

```
<400> SEQUENCE: 4

His Val Tyr Val Ala Thr
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide

<400> SEQUENCE: 5

Ser Val Tyr Val Ala Thr
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic peptide

<400> SEQUENCE: 6

His Ile Val Val Ala Thr
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic peptide

<400> SEQUENCE: 7

Ser Ile Val Val Ala Thr
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic peptide

<400> SEQUENCE: 8

His Val Val Val Ala Thr
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic peptide

<400> SEQUENCE: 9

Ser Val Val Val Ala Thr
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic peptide
```

```
<400> SEQUENCE: 10

His Ile Tyr Val Arg Thr
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic peptide

<400> SEQUENCE: 11

Ser Ile Tyr Val Arg Thr
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic peptide

<400> SEQUENCE: 12

His Val Tyr Val Arg Thr
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic peptide

<400> SEQUENCE: 13

Ser Val Tyr Val Arg Thr
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic peptide

<400> SEQUENCE: 14

His Ile Val Val Arg Thr
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic peptide

<400> SEQUENCE: 15

Ser Ile Val Val Arg Thr
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic peptide

<400> SEQUENCE: 16
```

His Val Val Val Arg Thr
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic peptide

<400> SEQUENCE: 17

His Ile Tyr Val Gly Thr
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic peptide

<400> SEQUENCE: 18

Ser Ile Tyr Val Gly Thr
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic peptide

<400> SEQUENCE: 19

His Val Tyr Val Gly Thr
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic peptide

<400> SEQUENCE: 20

Ser Val Tyr Val Gly Thr
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic peptide

<400> SEQUENCE: 21

His Ile Val Val Gly Thr
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic peptide

<400> SEQUENCE: 22

```
Ser Ile Val Val Gly Thr
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic peptide

<400> SEQUENCE: 23

His Val Val Val Gly Thr
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic peptide

<400> SEQUENCE: 24

Ser Val Val Val Gly Thr
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic peptide

<400> SEQUENCE: 25

His Ile Tyr Val Ala Val
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic peptide

<400> SEQUENCE: 26

Ser Ile Tyr Val Ala Val
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic peptide

<400> SEQUENCE: 27

His Val Tyr Val Ala Val
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic peptide

<400> SEQUENCE: 28

Ser Val Tyr Val Ala Val
```

```
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic peptide

<400> SEQUENCE: 29

His Ile Val Val Ala Val
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic peptide

<400> SEQUENCE: 30

Ser Ile Val Val Ala Val
1               5

<210> SEQ ID NO 31
<211> LENGTH: 6
<212> TYPE: PRT
<213> ORGANISM: Artificial Sequence
<220> FEATURE:
<223> OTHER INFORMATION: Synthetic peptide

<400> SEQUENCE: 31

His Val Val Val Ala Val
1               5

<210> SEQ ID NO 32
<211> LENGTH: 6
<212> TYPE: PRT
<213> ORGANISM: Artificial Sequence
<220> FEATURE:
<223> OTHER INFORMATION: Synthetic peptide

<400> SEQUENCE: 32

Ser Val Val Val Ala Val
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic peptide

<400> SEQUENCE: 33

His Ile Tyr Val Arg Val
1               5

<210> SEQ ID NO 34
<211> LENGTH: 6
<212> TYPE: PRT
<213> ORGANISM: Artificial Sequence
<220> FEATURE:
<223> OTHER INFORMATION: Synthetic peptide

<400> SEQUENCE: 34

Ser Ile Tyr Val Arg Val
1               5
```

```
<210> SEQ ID NO 35
<211> LENGTH: 6
<212> TYPE: PRT
<213> ORGANISM: Artificial Sequence
<220> FEATURE:
<223> OTHER INFORMATION: Synthetic peptide

<400> SEQUENCE: 35

His Val Tyr Val Arg Val
1               5

<210> SEQ ID NO 36
<211> LENGTH: 6
<212> TYPE: PRT
<213> ORGANISM: Artificial Sequence
<220> FEATURE:
<223> OTHER INFORMATION: Synthetic peptide

<400> SEQUENCE: 36

Ser Val Tyr Val Arg Val
1               5

<210> SEQ ID NO 37
<211> LENGTH: 6
<212> TYPE: PRT
<213> ORGANISM: Artificial Sequence
<220> FEATURE:
<223> OTHER INFORMATION: Synthetic peptide

<400> SEQUENCE: 37

His Ile Val Val Arg Val
1               5

<210> SEQ ID NO 38
<211> LENGTH: 6
<212> TYPE: PRT
<213> ORGANISM: Artificial Sequence
<220> FEATURE:
<223> OTHER INFORMATION: Synthetic peptide

<400> SEQUENCE: 38

Ser Ile Val Val Arg Val
1               5

<210> SEQ ID NO 39
<211> LENGTH: 6
<212> TYPE: PRT
<213> ORGANISM: Artificial Sequence
<220> FEATURE:
<223> OTHER INFORMATION: Synthetic peptide

<400> SEQUENCE: 39

His Val Val Val Arg Val
1               5

<210> SEQ ID NO 40
<211> LENGTH: 6
<212> TYPE: PRT
<213> ORGANISM: Artificial Sequence
<220> FEATURE:
<223> OTHER INFORMATION: Synthetic peptide

<400> SEQUENCE: 40

Ser Val Val Val Arg Val
1               5
```

```
<210> SEQ ID NO 41
<211> LENGTH: 6
<212> TYPE: PRT
<213> ORGANISM: Artificial Sequence
<220> FEATURE:
<223> OTHER INFORMATION: Synthetic peptide

<400> SEQUENCE: 41

His Ile Tyr Val Gly Val
1               5

<210> SEQ ID NO 42
<211> LENGTH: 6
<212> TYPE: PRT
<213> ORGANISM: Artificial Sequence
<220> FEATURE:
<223> OTHER INFORMATION: Synthetic peptide

<400> SEQUENCE: 42

Ser Ile Tyr Val Gly Val
1               5

<210> SEQ ID NO 43
<211> LENGTH: 6
<212> TYPE: PRT
<213> ORGANISM: Artificial Sequence
<220> FEATURE:
<223> OTHER INFORMATION: Synthetic peptide

<400> SEQUENCE: 43

His Val Tyr Val Gly Val
1               5

<210> SEQ ID NO 44
<211> LENGTH: 6
<212> TYPE: PRT
<213> ORGANISM: Artificial Sequence
<220> FEATURE:
<223> OTHER INFORMATION: Synthetic peptide

<400> SEQUENCE: 44

Ser Val Tyr Val Gly Val
1               5

<210> SEQ ID NO 45
<211> LENGTH: 6
<212> TYPE: PRT
<213> ORGANISM: Artificial Sequence
<220> FEATURE:
<223> OTHER INFORMATION: Synthetic peptide

<400> SEQUENCE: 45

His Ile Val Val Gly Val
1               5

<210> SEQ ID NO 46
<211> LENGTH: 6
<212> TYPE: PRT
<213> ORGANISM: Artificial Sequence
<220> FEATURE:
<223> OTHER INFORMATION: Synthetic peptide

<400> SEQUENCE: 46

Ser Ile Val Val Gly Val
1               5
```

```
<210> SEQ ID NO 47
<211> LENGTH: 6
<212> TYPE: PRT
<213> ORGANISM: Artificial Sequence
<220> FEATURE:
<223> OTHER INFORMATION: Synthetic peptide

<400> SEQUENCE: 47

His Val Val Val Gly Val
1               5

<210> SEQ ID NO 48
<211> LENGTH: 6
<212> TYPE: PRT
<213> ORGANISM: Artificial Sequence
<220> FEATURE:
<223> OTHER INFORMATION: Synthetic peptide

<400> SEQUENCE: 48

Ser Val Val Val Gly Val
1               5

<210> SEQ ID NO 49
<211> LENGTH: 7
<212> TYPE: PRT
<213> ORGANISM: Artificial Sequence
<220> FEATURE:
<223> OTHER INFORMATION: Synthetic peptide

<400> SEQUENCE: 49

Gly Ser Ile Tyr Val Ala Thr
1               5

<210> SEQ ID NO 50
<211> LENGTH: 7
<212> TYPE: PRT
<213> ORGANISM: Artificial Sequence
<220> FEATURE:
<223> OTHER INFORMATION: Synthetic peptide

<400> SEQUENCE: 50

Ser Ile Tyr Val Ala Thr Ala
1               5

<210> SEQ ID NO 51
<211> LENGTH: 8
<212> TYPE: PRT
<213> ORGANISM: Artificial Sequence
<220> FEATURE:
<223> OTHER INFORMATION: Synthetic peptide

<400> SEQUENCE: 51

Gly Gly Ser Ile Tyr Val Ala Thr
1               5

<210> SEQ ID NO 52
<211> LENGTH: 8
<212> TYPE: PRT
<213> ORGANISM: Artificial Sequence
<220> FEATURE:
<223> OTHER INFORMATION: Synthetic peptide

<400> SEQUENCE: 52

Ala Ser Ile Tyr Val Ala Thr Ala
1               5

<210> SEQ ID NO 53
```

```
<211> LENGTH: 8
<212> TYPE: PRT
<213> ORGANISM: Artificial Sequence
<220> FEATURE:
<223> OTHER INFORMATION: Synthetic peptide

<400> SEQUENCE: 53

Gly Gly Ser Val Tyr Val Ala Thr
1               5

<210> SEQ ID NO 54
<211> LENGTH: 7
<212> TYPE: PRT
<213> ORGANISM: Artificial Sequence
<220> FEATURE:
<223> OTHER INFORMATION: Synthetic peptide

<400> SEQUENCE: 54

Ala Ser Val Tyr Val Ala Thr
1               5

<210> SEQ ID NO 55
<211> LENGTH: 7
<212> TYPE: PRT
<213> ORGANISM: Artificial Sequence
<220> FEATURE:
<223> OTHER INFORMATION: Synthetic peptide

<400> SEQUENCE: 55

Gly Ser Val Tyr Val Ala Thr
1               5

<210> SEQ ID NO 56
<211> LENGTH: 8
<212> TYPE: PRT
<213> ORGANISM: Artificial Sequence
<220> FEATURE:
<223> OTHER INFORMATION: Synthetic peptide

<400> SEQUENCE: 56

Ser Val Tyr Val Ala Thr Ala Ala
1               5

<210> SEQ ID NO 57
<211> LENGTH: 8
<212> TYPE: PRT
<213> ORGANISM: Artificial Sequence
<220> FEATURE:
<223> OTHER INFORMATION: Synthetic peptide

<400> SEQUENCE: 57

Gly Ser Val Tyr Val Ala Thr Ala
1               5

<210> SEQ ID NO 58
<211> LENGTH: 7
<212> TYPE: PRT
<213> ORGANISM: Artificial Sequence
<220> FEATURE:
<223> OTHER INFORMATION: Synthetic peptide

<400> SEQUENCE: 58

Tyr Ser Ile Val Val Gly Thr
1               5

<210> SEQ ID NO 59
<211> LENGTH: 8
```

```
<212> TYPE: PRT
<213> ORGANISM: Artificial Sequence
<220> FEATURE:
<223> OTHER INFORMATION: Synthetic peptide

<400> SEQUENCE: 59

Thr Gly Ser Ile Val Val Gly Thr
1               5

<210> SEQ ID NO 60
<211> LENGTH: 8
<212> TYPE: PRT
<213> ORGANISM: Artificial Sequence
<220> FEATURE:
<223> OTHER INFORMATION: Synthetic peptide

<400> SEQUENCE: 60

Gly Ser Ile Val Val Gly Thr His
1               5

<210> SEQ ID NO 61
<211> LENGTH: 8
<212> TYPE: PRT
<213> ORGANISM: Artificial Sequence
<220> FEATURE:
<223> OTHER INFORMATION: Synthetic peptide

<400> SEQUENCE: 61

Ser Ile Val Val Gly Thr Ala Gly
1               5

<210> SEQ ID NO 62
<211> LENGTH: 8
<212> TYPE: PRT
<213> ORGANISM: Artificial Sequence
<220> FEATURE:
<223> OTHER INFORMATION: Synthetic peptide

<400> SEQUENCE: 62

Gly Ser Ile Val Val Gly Thr Gly
1               5

<210> SEQ ID NO 63
<211> LENGTH: 7
<212> TYPE: PRT
<213> ORGANISM: Artificial Sequence
<220> FEATURE:
<223> OTHER INFORMATION: Synthetic peptide

<400> SEQUENCE: 63

Ser Val Val Val Arg Thr Ile
1               5

<210> SEQ ID NO 64
<211> LENGTH: 8
<212> TYPE: PRT
<213> ORGANISM: Artificial Sequence
<220> FEATURE:
<223> OTHER INFORMATION: Synthetic peptide

<400> SEQUENCE: 64

Ser Val Val Val Arg Thr Ile Val
1               5

<210> SEQ ID NO 65
<211> LENGTH: 7
<212> TYPE: PRT
```

<213> ORGANISM: Artificial Sequence
<220> FEATURE:
<223> OTHER INFORMATION: Synthetic peptide

<400> SEQUENCE: 65

Gly Ser Val Val Val Arg Thr
1               5

<210> SEQ ID NO 66
<211> LENGTH: 8
<212> TYPE: PRT
<213> ORGANISM: Artificial Sequence
<220> FEATURE:
<223> OTHER INFORMATION: Synthetic peptide

<400> SEQUENCE: 66

Gly Gly Ser Val Val Val Arg Thr
1               5

<210> SEQ ID NO 67
<211> LENGTH: 8
<212> TYPE: PRT
<213> ORGANISM: Artificial Sequence
<220> FEATURE:
<223> OTHER INFORMATION: Synthetic peptide

<400> SEQUENCE: 67

Gly Ser Val Val Val Arg Thr Gly
1               5

<210> SEQ ID NO 68
<211> LENGTH: 7
<212> TYPE: PRT
<213> ORGANISM: Artificial Sequence
<220> FEATURE:
<223> OTHER INFORMATION: Synthetic peptide

<400> SEQUENCE: 68

Ala His Ile Val Val Gly Thr
1               5

<210> SEQ ID NO 69
<211> LENGTH: 8
<212> TYPE: PRT
<213> ORGANISM: Artificial Sequence
<220> FEATURE:
<223> OTHER INFORMATION: Synthetic peptide

<400> SEQUENCE: 69

Gly His Ile Val Val Gly Thr Ala
1               5

<210> SEQ ID NO 70
<211> LENGTH: 8
<212> TYPE: PRT
<213> ORGANISM: Artificial Sequence
<220> FEATURE:
<223> OTHER INFORMATION: Synthetic peptide

<400> SEQUENCE: 70

His Ile Val Val Gly Thr Leu Ala
1               5

<210> SEQ ID NO 71
<211> LENGTH: 8
<212> TYPE: PRT
<213> ORGANISM: Artificial Sequence

```
<220> FEATURE:
<223> OTHER INFORMATION: Synthetic peptide

<400> SEQUENCE: 71

Ala Leu His Ile Val Val Gly Thr
1               5
```

PGC-1α-MODULATING PEPTIDES

This application claims the priority and benefit of International Application PCT/EP2012/055259, filed Mar. 23, 2012, ES 201130439, filed Mar. 25, 2011, and U.S. Application Ser. No. 61/467,648, filed Mar. 25, 2011, from which the PCT application claims priority, the disclosures of which are incorporated herein by reference in their entireties.

FIELD OF THE INVENTION

This invention relates to peptides capable of modulating PGC-1α and cosmetic or pharmaceutical compositions which contain these peptides useful in the treatment and/or care of those conditions, disorders and/or diseases which improve or are prevented by PGC-1α modulation.

BACKGROUND OF THE INVENTION

Adipose tissue or body fat is a connective tissue derived from mesenchyme made up of the association of cells which accumulate lipids in their cytoplasm: adipocytes. The adipose tissue of mammals can be classified into two types: white adipose tissue and brown adipose tissue. White adipose tissue is the predominant tissue, formed by unilocular adipocytes which accumulate their entire lipid content in just one drop, and whose main function is the accumulation of energy reserves in the form of triglycerides. Brown adipose tissue which less common and is formed by multilocular adipocytes and usually disappears soon after birth, being particularly relevant in hibernating mammals. In humans, fetuses and newborns present brown adipose tissue in their cervical, axillary, peri-renal and peri-adrenal deposits; in adults, however, there are no brown fatty deposits but instead there are populations of multilocular adipocytes intercalated between white adipose tissue. Brown adipose tissue is highly thermogenic, it has a large number of mitochondria in its cytoplasm and high levels of mitochondrial gene expression, and its function consists of energy dissipation in the form of heat.

One of the distinctive features of adipose tissue is its plasticity. This plasticity is a particular result of the ability of the adipose tissue to change its volume either because of a change in the amount of intracellular lipids (increase in size of adipocytes) or due to the change in number of the adipocytes. Mature adipocytes accumulate fat as a source of energy (i.e. excess calorie intake) and are able to release it in the case that energy is needed (i.e. periods of fasting, exposure to cold, etc.). The number of mature adipocytes is maintained more or less constant from adulthood. However, adipocyte precursor cells or pre-adipocytes are continually multiplied and differentiate into mature adipocytes able to accumulate fat. This mechanism is called differentiation or adipogenesis.

Adipogenesis is principally characterized by a morphological modification of the precursor cells, a phenotype change and the appearance of adipocyte-specific markers. When differentiation begins, the majority of genes are activated, among them PPARγ (peroxisome proliferator-activated receptor-γ). PPARγ, a member of the PPAR nuclear receptor family which is expressed in adipose tissue, is a master regulator of adipocyte differentiation [Tontonoz P. et al., "Regulation of adipocyte gene expression and differentiation by peroxisome proliferator activated receptor gamma". Curr. Opin. Genet. Dev., (1995), 5(5), 571-576]. These receptors act as transcription factors and regulate gene expression in cell differentiation processes. PPARγ is essential in adipose tissue and forms heterodimers with the retinoid X receptors which are bound to specific regions in the DNA of the target genes and regulate their expression. The genes activated by PPARγ stimulate lipid uptake by the fatty cells and strongly induce white adipose tissue differentiation. PPARγ knockout mice are capable of producing adipose tissue when they are fed on a diet high in fat [Jones J. R. et al., "Deletion of PPARgamma in adipose tissues of mice protects against high fat diet-induced obesity and insulin resistance". Proc. Natl. Acad. Sci. U.S.A., (2005), 102(17), 6207-6212].

PPARγ has a transcriptional role in the differentiation of pre-adipocytes into mature adipocytes, since it has been seen that PPARγ activation through ligand binding gives rise to the accumulation of lipids, morphological changes and promotes the expression of adipose tissue-specific genes [Tontonoz P. et al., "Stimulation of adipogenesis in fibroblasts by PPARγ2, a lipid-activated transcription factor", (1994), Cell, 79, 7355-7359]. In addition, there is data which demonstrates that adipogenesis stimulation due to PPARγ activation through ligand binding also occurs in vivo [Okuno A. et al., "Troglitazone increases the number of small adipocytes without the change of white adipose tissue mass in obese Zucker rats". J. Clin. Invest., (1998), 101, 1354-1361]. The involvement of PPARγ in adipogenesis is also supported by the fact that patients with a mutation in PPARγ which makes this receptor constantly activated present greater adipocyte differentiation and obesity [Ristow M. et al., "Obesity associated with a mutation in a genetic regulator of adipocyte differentiation". N. Engl. J. Med., (1998), 339, 953-959]. The mechanism by which PPARγ stimulates adipogenesis seems to be related to its mediating effect of the cell cycle arrest [Classon M. et al., "Opposing roles of pRB and p107 in adipocyte differentiation". P.N.A.S., (2000), 97, 10826-10831], since, in general cell division and cell differentiation are considered to be mutually exclusive processes.

Serious efforts have been made by the pharmaceutical to developing new PPARγ modulatory compounds with the aim of slowing down the advance of obesity and type 2 diabetes in developed countries. PPARγ agonists have also been described for the treatment and/or prevention of disorders or diseases of the skin such as disorders due to keratinocyte hyperproliferation such as psoriasis, lichen planus, skin lesions associated with lupus, dermatitis such as atopic, seborrheic or solar dermatitis, keratosis such as seborrheic, senile, actinic, photoinduced or follicular keratosis, acne vulgar, nevus, keloids or wrinkles among others [WO 95/535108 A1; EP 1041977 B1; WO 2009/153373 A2; Krentz A. J. et al., "Type 2 diabetes, psoriasis and thiazolidinediones", (2006), Int. J. Clin. Pract., 60, 362-363], keratinization disorders such as common acne, comedones, polymorphous, rosacea, nodulocystic acne, conglobate acne, senile acne, ichthyosis, Darier's disease, keratodermia palmoplantaris, leukoplakia, mucosal lichen or cutaneous lichen; conditions with an inflammatory component such as cutaneous psoriasis, mucosal or nail psoriasis, psoriatic rheumatism, cutaneous atopia including eczema; dermal proliferations such as common warts, flat warts, epidermodysplasia verruciformis, oral papillomatosis; immune dermatoses such as lupus erythematosus, bullous diseases, scleroderma, skin aging, actinic keratosis, and pigmentation disorders [EP 1781297 B1], alopecia greata or vitiligo [EP 1331934 B1], cutaneous lipid metabolism disorders such as hyperseborrhea of acne and simple seborrhea [EP 1781297 B1], regulation of the fibroblasts or myofibroblasts function, excess of extracellular matrix production, healing or reepithelialization processes, nodular fascitis or Dupuytren's contracture [US 2004/0152746 A1; US 2008/0182780 A1] among others.

PPAR receptors are transcription factors which regulate adipocyte-specific gene expression, but there is another level of regulation formed by a group of proteins which modulate these transcription factors: transcriptional coactivators. A transcription coactivator is a protein complex which increases the transcription rate of its target by interacting with transcription factors but does not recognize nor is it bound to specific DNA sequences. These complexes comprise proteins which mediate the anchorage in the transcription and protein factors which exercise specific functions, such as the modification of histones through acetyltransferase activity, through phosphorylation and through methylation, unwinding and remodeling ATP-dependent chromatin, and others. Coactivators are recruited to the target genes by protein-protein interactions with transcription factors which are bound to DNA. The latter modify the structure of the chromatin in the target gene by association with the RNA polymerase machinery, giving rise to an increase in the transcription of the target genes. Interactions between coactivators and DNA-binding factors are specific, and depend on the presence of certain protein interfaces and signals which activate transcription factors. These interactions are highly versatile: the same coactivator can interact with multiple transcription factors, and a transcription factor can interact with several coactivators. The possibility of regulating gene expression by modulation of transcription coactivators opens the door to their study for therapeutic purposes.

In mammals, one of the most notable examples of the regulation of metabolic routes by transcription coactivators is PPARγ coactivator 1α [Handschin C. et al., "*Peroxisome proliferator-activated receptor gamma coactivator 1 coactivators, energy homeostasis, and metabolism*" Endocr Rev., (2006), 27(7), 728-735]. PGC-1α is activated by signals which control energy and nutrient homeostasis. PGC-1α activates gene expression through specific interaction with transcription factors, among them PPARγ, which are bound to metabolism gene promoters. The fact that PGC-1α controls the activity of PPARγ suggests that it can be a target for the development of compounds useful in the treatment and/or care of those conditions, disorders and/or diseases mediated by PPARγ, such as obesity, type 2 diabetes, resistance to insulin, or skin complaints due to keratinocyte hyperproliferation disorders, keratinization disorders or healing or reepithelialization processes, among others.

It has been described in the bibliography that during the adipogenesis process the PGC-1α expression levels increase independently of PPAR [Semple R. C. et al., "*Expression of the thermogenic nuclear hormone receptor coactivator PGC-1α is reduced in the adipose tissue of morbidly obese subjects*". Int. J. Obes., (2004), 28, 176-179] which suggests that PGC-1α is a potential target per se for processes in which the regulation of adipogenesis is desirable and, therefore, the regulation of the volume of adipose tissue.

Described in the prior art are PGC-1α modulators not solely for treating obesity, type 2 diabetes or the resistance to insulin [US 2009/0029933 A1], but also for the treatment of neurological disorders and diseases [US 2009/0005314 A1] or to regulate the formation of type I muscular fibers [US 2006/0035849 A1].

The variable distribution of adipose tissue is what defines the body's figure and facial shape. Subcutaneous adipose tissue is located in places such as the cheeks, lips, eyelids, extremities, hands, buttocks, thighs and bust. An increase in the volume of the subcutaneous adipocytes in certain areas of the human body can be related to smooth skin and a youthful, healthy appearance, as with the face, whilst in other areas it is considered an undesired aesthetic defect, as it happens with the thighs. Thus, regulation of PGC-1α and therefore, regulation of the volume of adipose tissue is an objective not just for the pharmaceutical sector, due to its potential benefit in the treatment and/or prevention of different disorders or diseases such as obesity, type 2 diabetes, neurological disorders and diseases and the resistance to insulin, but also by the cosmetic sector with the aim of shaping ones figure.

With age, facial marks such as expression lines appear to be normal, due to the senescence of the cells which make up the skin, due to elastosis, to a decrease in collagen levels and lipoatrophy. The gradual loss of subcutaneous fat greatly contributes to skin sagging, greater depth of wrinkle furrows, greater skin dryness, and in general results in thinner and weaker skin. This effect is clearly visible on the hands and the lower part of the neck and neckline. Likewise, some diseases involve lipolytic processes which are clearly visible on the face, as is the case of acquired immune deficiency syndrome (AIDS), stigmatizing the sufferer. Therefore, the increase in the volume of adipose tissue in the areas affected by lipoatrophy or lipodystrophy is of interest to restore a more youthful appearance. Likewise, an increase in the layer of subcutaneous adipocytes is also desirable in the case of women who wish to increase the size of their breasts or buttocks. The breasts are formed by mammary glands, connective tissue and adipose tissue. The volume of adipose tissue is variable, and therefore it is a determining factor of the volume and shape of the breast. Topical application of compounds that decrease lipolysis and/or increase lipogenesis or adipogenesis presents many advantages over usual process for breast enlargement, such as silicone breast implants or tissue transplants, invasive techniques which require surgery and are not risk free.

The decrease in the volume of adipose tissue is also an aim of the cosmetics and aesthetics industry, since at present there are no satisfactory solutions for the treatment and/or prevention of cellulitis. Cellulitis is an adipose and subcutaneous tissue condition which is characterized by providing the skin with a characteristic and aesthetically unpleasant orange peel appearance. Also called local lipodystrophy, cellulitis mainly and almost exclusively affects women, and can be considered a trait of sexual dimorphism. The common areas for the formation of cellulitis are the thighs, buttocks, upper arms, and less frequently, the back part of the neck and the lower legs. Although local lipodystrophy or cellulitis is not synonymous with obesity or being overweight, there is a correlation between cellulitis and adipose tissue hypertrophy. The origin of cellulitis is not well defined, but it is known that, as well as the excess of adipose tissue, its appearance is due to several causes. One of them is the difference between sexes in the histological distribution of the subcutaneous fat lobes due to differences in the connective adipose tissue septa: males have diagonal septa and small lobes, whilst the septa in women are rectangular and the lobes are larger. Another cause may be the existence of changes to the microvascular network which irrigates the adipose tissue. The presence of plasmatic exudate in the subcutaneous connective tissue, giving rise to non-inflammatory edema, is another possible cause, together with the changes to the fundamental interstitial substance of proteoglycans.

A four stage classification of the establishment of cellulitis has been determined [Terranova F. et al., "*Cellulite: nature and aetiopathogenesis*". Int. J. Cosmet. Sci., 2006, 28(3), 157-167]. Initially, phase I, the walls of the blood capillaries become more permeable and this causes blood plasma to be released from the vessels situated between the layers of adipose tissue, which leads to the appearance of edema. In the following phase II, the aggregation of adipose cells and the amplification of the fibrillar network of collagen bundles which interconnect the adipocytes prevent the circulation of blood leading to hemostasis. In phase III, the adipocytes are added forming millimeter-sized micronodules, enveloped by less mobile collagen fibers. Lastly, in phase IV many of these micronodules are added forming larger macronodules (from 2 to 20 mm), which can compress the adjoining nerve endings, causing an increase in the sensitivity of the skin of the cellulitis patient, which can become painful. It is for this reason that phase IV is considered to be pathological due to the clinical symptoms which appear, whilst the other three phases are considered to be aesthetic skin problems. It is believed that the initial phases are more or less reversible whilst the final phases are irreversible.

Both the cosmetic and pharmaceutical sector and the food sector have made various efforts to develop compounds able to regulate the volume of the adipose tissue. Examples of compounds intended to increase the volume of the adipose tissue are found in the prior art, whether they are from plant extracts, such as those described in documents U.S. Pat. No. 7,618,662 B2 and US 2003/0044475 A1 among others, compounds which are natural in origin [EP 2046283 A2] as well as compounds that are synthetic in origin [U.S. Pat. No. 5,348,943 A]. Likewise, several treatments against cellulitis whose objective is to reduce the volume of adipose tissue are available on the market. These are based principally on deep lymphatic drainage massage (manual or electromechanical), sequential pneumatic compression, electrolipolysis or mesotherapy. Physiotherapy treatments such as massages and lymphatic drainage stimulate blood and lymphatic microcirculation and increase the removal of excess fluids in the adipose tissue. Massage also has the effect of delaying the subsequent development of fibrosclerosis and the aggregation of adipocytes into nodules. These treatments are usually combined with the application of cosmetic products with anti-cellulite effectiveness. The most widely used compounds are caffeine and its derivatives, carnitine, forskolin as well as plant extracts such as those described in documents EP 2210610 A1, DE 202009010648 U1 and U.S. Pat. No. 7,410,658 B2 among others, or compounds which are natural in origin (isoflavones such as those described in document EP 1234572 A1 or menthol derivatives such as those described in international application WO 2010/089421 A2 among others).

However, despite the arsenal of existing compounds and/or extracts, the cosmetic, pharmaceutical and food industry is still interested in developing alternatives to the existing compounds capable of modulating PGC-1α.

BRIEF DESCRIPTION

In one aspect of the exemplary embodiment, a peptide of general formula (I)

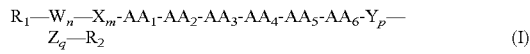

its stereoisomers, mixtures thereof and/or its cosmetic or pharmaceutical acceptable salts is disclosed, wherein $AA_1$ is selected from the group consisting of -His- and -Ser-; $AA_2$ is selected from the group consisting of -Ile- and -Val-; $AA_3$ is selected from the group consisting of -Tyr- and -Val-; $AA_4$ is -Val-; $AA_5$ is selected from the group consisting of -Ala-, -Arg- and -Gly-; $AA_6$ is selected from the group consisting of -Thr- and -Val-; W, X, Y and Z are amino acids and are independently selected from amongst themselves; n, m, p and q are independently selected from amongst themselves and have a value of 0 or 1; n+m+p+q is lower or equal to 2; $R_1$ is selected from the group consisting of H, substituted and unsubstituted non-cyclic aliphatic groups, substituted and unsubstituted alicyclyls, substituted and unsubstituted heterocyclyls, substituted and unsubstituted heteroarylalkyls, substituted and unsubstituted aryls, substituted and unsubstituted aralkyls and $R_5$—CO—, wherein $R_5$ is selected from the group consisting of H, substituted and unsubstituted non-cyclic aliphatic groups, substituted and unsubstituted alicyclyls, substituted and unsubstituted aryls, substituted and unsubstituted aralkyls, substituted and unsubstituted heterocyclyls and substituted and unsubstituted heteroarylalkyls; $R_2$ is selected from the group consisting of —$NR_3R_4$, —$OR_3$ and —$SR_3$, wherein $R_3$ and $R_4$ are independently selected from the group consisting of H, substituted and unsubstituted non-cyclic aliphatic groups, substituted and unsubstituted alicyclyls, substituted and unsubstituted heterocyclyls, substituted and unsubstituted heteroarylalkyls, substituted and unsubstituted aryls, substituted and unsubstituted aralkyls; and wherein $R_1$ and $R_2$ are not α-amino acids.

DETAILED DESCRIPTION OF THE INVENTION

This invention provides a solution to the above-mentioned problem. Surprisingly the applicant of this invention has found that the expression of the coactivator PGC-1α can be modulated by certain synthetic peptides. The inventors have therefore determined that these synthetic peptides are capable of modulating the coactivator PGC-1α. These peptides are useful for the treatment and/or care of those conditions, disorders and/or diseases which improve or are prevented by the modulation of PGC-1α.

DEFINITIONS

In order to facilitate the comprehension of this invention, the meanings of some terms and expressions as used in the context of the invention are included.

In the context of this invention "PGC-1α modulation" is understood to be both the increase and decrease of PGC-1α synthesis and the increase or inhibition of its activity. In the same way, "PPARγ modulation" is understood to be both the increase or decrease of PPARγ synthesis and the increase or inhibition of its activity.

In the context of this invention "skin" is understood to be the layers which comprise it, from the uppermost layer or stratum corneum to the lowermost layer or hypodermis, both inclusive. These layers are composed of different types of cells such as keratinocytes, fibroblasts, melanocytes and/or adipocytes among others. In the context of this invention, the term "skin" includes the scalp.

The term "treatment", as used in the context of this report, refers to the administration of a peptide according to the invention to alleviate or eliminate a disease or disorder or reduce or eliminate one or more symptoms associated with this disease or disorder. The term "treatment" also covers the ability to alleviate or eliminate the physiological consequences of the disease or disorder.

In the context of this invention "care" comprises the prevention of diseases and/or disorders.

The term "prevention", as used in this invention, refers to the ability of a peptide in the invention to prevent, delay, or hinder the appearance or development of a disease or disorder before its appearance.

In the context of this invention, the term "aging" refers to the changes experienced by the skin with age (chronoaging) or through exposure to the sun (photoaging) or to environmental agents such as tobacco smoke, extreme climatic conditions of cold or wind, chemical contaminants or pollutants, and includes all the external visible and/or perceptible changes through touch, such as and not restricted to, the development of discontinuities on the skin such as wrinkles, fine lines, furrows, irregularities or roughness, increase in the size of pores, loss of elasticity, loss of firmness, loss of smoothness, loss of the capacity to recover from deformation, loss of resilience, sagging of the skin such as sagging cheeks, the appearance of bags under the eyes or the appearance of a double chin, among others, changes to the color of the skin such as marks, reddening, bags or the appearance of hyperpigmented areas such as age spots or freckles among others, anomalous differentiation, hyperkeratinization, elastosis, keratosis, hair loss, orange peel skin, loss of collagen structure and other histological changes of the stratum corneum, of the dermis, epidermis, vascular system (for example the appearance of spider veins or telangiectasias) or of those tissues close to the skin, among others. The term "photoaging" groups together the set of processes due to the prolonged exposure of the skin to ultraviolet radiation which result in the premature aging of the skin, and present the same physical characteristics as aging, such as and not restricted to, flaccidity, sagging, changes to the color or irregularities in the pigmentation, abnormal and/or excessive keratinization. The sum of different environmental factors as exposure to tobacco smoke, exposure to pollution, and climatic conditions such as cold and/or wind also contributes to the aging of the skin.

In this description the abbreviations used for amino acids follow the recommendations of the 1983 IUPACIUB Commission of Biochemical Nomenclature specified in *Eur. J. Biochem.*, (1984), 138, 9-37.

Thus, for example, Ala represents $NH_2—CH(CH_3)—COOH$, Ala- represents $NH_2—CH(CH_3)—CO$, -Ala represents $—NH—CH(CH_3)—COOH$ and -Ala- represents $—NH—CH(CH_3)—CO—$. Therefore, the hyphen, which represents the peptide bond, eliminates the OH in the 1-carboxyl group of the amino acid (represented here in the conventional non-ionized form) when situated to the right of the symbol, and eliminates the H of the 2-amino group of the amino acid when situated to the left of the symbol; both modifications can be applied to the same symbol (see Table 1).

TABLE 1

Structures of the amino acids and their nomenclature in one and three letter code

| Symbol | Residue |
| --- | --- |
| Alanyl-Ala-A | |
| Seryl-Ser-S | |
| Valyl-Val-V | |
| Histidyl-His-H | |
| Isoleucyl-Ile-I | |
| Glycyl-Gly-G | |
| Tyrosyl-Tyr-Y | |
| Treonyl-Thr-T | |
| Arginyl-Arg-R | |

The abbreviation "Ac-" is used in this description to denote the acetyl group ($CH_3—CO—$) and the abbreviation "Palm-" is used to denote the palmitoyl group ($CH_3—(CH_2)_{14}—CO—$).

The term "non-cyclic aliphatic group" is used in this invention to cover, for example and not restricted to, the linear or branched alkyl, alkenyl and alkynyl groups.

The term "alkyl group" refers to a saturated, linear or branched group, which has between 1 and 24, preferably between 1 and 16, more preferably between 1 and 14, even more preferably between 1 and 12, yet more preferably 1, 2, 3, 4, 5 or 6 carbon atoms and is bound to the rest of the molecule by a single bond, including, for example and not restricted to, methyl, ethyl, isopropyl, isobutyl, tert-butyl, heptyl, octyl, decyl, dodecyl, lauryl, hexadecyl, octadecyl, amyl, 2-ethylhexyl, 2-methylbutyl, 5-methylhexyl and similar.

The term "alkenyl group" refers to a linear or branched group, which has between 2 and 24, preferably between 2 and 16, more preferably between 2 and 14, even more preferably between 2 and 12, yet more preferably 2, 3, 4, 5 or 6 carbon atoms, with one or more double carbon-carbon bonds, preferably with 1, 2 or 3 double carbon-carbon bonds, conjugated or unconjugated, which is bound to the rest of the molecule by a single bond, including, for example and not restricted to, vinyl, oleyl, linoleyl and similar groups.

The term "alkynyl group" refers to a linear or branched group, which has between 2 and 24, preferably between 2 and 16, more preferably between 2 and 14, even more preferably between 2 and 12, yet more preferably 2, 3, 4, 5 or 6 carbon atoms, with one or more triple carbon-carbon bonds, preferably 1, 2 or 3 triple carbon-carbon bonds, conjugated or unconjugated, which is bound to the rest of the molecule by a single bond, including, for example and not restricted to, the ethynyl group, 1-propinyl, 2-propinyl, 1-butinyl, 2-butinyl, 3-butinyl, pentinyl, such as 1-pentinyl, and similar.

The term "alycyclyl group" is used in this invention to cover, for example and not restricted to, cycloalkyl or cycloalkenyl or cycloalkynyl groups.

The term "cycloalkyl" refers to a saturated mono- or polycyclic aliphatic group which has between 3 and 24, preferably between 3 and 16, more preferably between 3 and 14, even more preferably between 3 and 12, yet more preferably between 3, 4, 5 or 6 carbon atoms and which is bound to the rest of the molecule by a single bond, including, for example and not restricted to, cyclopropyl, cyclobutyl, cyclopentyl, cyclohexyl, cycloheptyl, methyl cyclohexyl, dimethyl cyclohexyl, octahydroindene, decahydronaphthalene, dodecahydrophenalene and similar.

The term "cycloalkenyl" refers to a non-aromatic mono- or polycyclic aliphatic group which has between 5 and 24, preferably between 5 and 16, more preferably between 5 and 14, even more preferably between 5 and 12, yet more preferably 5 or 6 carbon atoms, with one or more double carbon-carbon bonds, preferably 1, 2 or 3 double carbon-carbon bonds, conjugated or unconjugated, and which is bound to the rest of the molecule by a single bond, including, for example and not restricted to, the cyclopent-1-en-1-yl group and similar.

The term "cycloalkynyl" refers to a non-aromatic mono- or polycyclic aliphatic group which has between 8 and 24, preferably between 8 and 16, more preferably between 8 and 14, even more preferably between 8 and 12, yet more preferably 8 or 9 carbon atoms, with one or more triple carbon-carbon bonds, preferably 1, 2 or 3 triple carbon-carbon bonds, conjugated or unconjugated, and which is bound to the rest of the molecule by a single bond, including, for example and not restricted to, the cycloct-2-in-1-yl group and similar.

The term "aryl group" refers to an aromatic group which has between 6 and 30, preferably between 6 and 18, more preferably between 6 and 10, even more preferably between 6 or 10 carbon atoms, which comprises 1, 2, 3 or 4 aromatic rings, bound by a carbon-carbon bond or fused, including, for example and not restricted to, phenyl, naphthyl, diphenyl, indenyl, phenanthryl or antranyl, among others; or a aralkyl group.

The term "aralkyl group" refers to an alkyl group substituted by an aromatic group, with between 7 and 24 carbon atoms and including, for example and not restricted to, —$(CH_2)_{1-6}$-phenyl, —$(CH_2)_{1-6}$-(1-naphthyl), —$(CH_2)_{1-6}$-(2-naphthyl), —$(CH_2)_{1-6}$—CH(phenyl)$_2$ and similar.

The term "heterocyclyl group" refers to a hydrocarbonated ring of 3-10 members, in which one or more of the atoms in the ring, preferably 1, 2 or 3 of the atoms in the ring, is a different element to carbon, such as nitrogen, oxygen or sulfur and can be saturated or unsaturated. For the purposes of this invention, the heterocycle can be a monocyclic, bicyclic or tricyclic system, which can include systems of condensed rings; and the nitrogen, carbon or sulfur atoms can optionally be oxidized in the radical heterocyclyl; the nitrogen atom can optionally be quaternized; and the radical heterocyclyl can be partially or completely saturated or aromatic. The greatest preference is for the term heterocyclyl to refer to a ring of 5 or 6 members.

The term "heteroarylalkyl group" refers to an alkyl group substituted by a substituted or unsubstituted aromatic heterocyclyl group, the alkyl group having from 1 to 6 carbon atoms and the aromatic heterocyclyl between 2 and 24 carbon atoms and from 1 to 3 atoms other than carbon and including, for example and not restricted to, —$(CH_2)_{1-6}$-imidazolyl, —$(CH_2)_{1-6}$-triazolyl, —$(CH_2)_{1-6}$-thienyl, —$(CH_2)_{1-6}$-furyl, —$(CH_2)_{1-6}$-pyrrolidinyl and similar.

As it is understood in this technical field, there can be a certain level of substitution of the aforementioned groups. Therefore, there can be substitution in any of the groups of this invention. The references in this document to substituted groups in the groups of this invention indicate that the specified radical can be substituted in one or more positions available by one or more substituents, preferably in 1, 2 or 3 positions, more preferably in 1 or 2 positions, yet more preferably in 1 position. These substituents include, for example and not restricted to, $C_1$-$C_4$ alkyl; hydroxyl; $C_1$-$C_4$ alcoxyl; amino; $C_1$-$C_4$ aminoalkyl; $C_1$-$C_4$ carbonyloxy; $C_1$-$C_4$ oxycarbonyl; halogen such as fluoride, chlorine, bromine and iodine; cyano; nitro; azide; $C_1$-$C_4$ alkylsulfonyl; thiol; $C_1$-$C_4$ alkylthio; $C_6$-$C_{30}$ aryloxy such as phenoxyl; —$NR_b$ (C=$NR_b$)$NR_bR_c$; wherein $R_b$ and $R_c$ are independently selected from the group formed by H, $C_1$-$C_4$ alkyl, $C_2$-$C_4$ alkenyl, $C_2$-$C_4$ alkynyl, $C_3$-$C_{10}$ cycloalkyl, $C_6$-$C_{18}$ aryl, $C_7$-$C_{17}$ aralkyl, heterocyclyl of 3-10 members or protective group of the amino group.

Compounds in the Invention

The peptides of the invention are defined by the general formula (I)

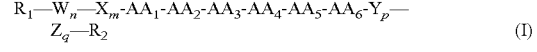
(I)

their stereoisomers, mixtures thereof and/or their cosmetically or pharmaceutically acceptable salts, wherein:
$AA_1$ is selected from the group formed by -His- and -Ser-;
$AA_2$ is selected from the group formed by -Ile- and -Val-;
$AA_3$ is selected from the group formed by -Tyr- and -Val-;
$AA_4$ is -Val-;
$AA_5$ is selected from the group formed by -Ala-, -Arg- and -Gly-;
$AA_6$ is selected from the group formed by -Thr- and -Val-;
W, X, Y, Z are amino acids and are independently selected from among themselves;
n, m, p and q are independently selected from among themselves and have a value of 0 or 1;
n+m+p+q is lower or equal to 2;
$R_1$ is selected from the group formed by H, a non-cyclic substituted or unsubstituted aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO—, wherein $R_5$ is selected from the group formed by H, a non-cyclic substituted or unsubstituted aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl;

$R_2$ is selected from the group formed by —$NR_3R_4$, —$OR_3$ and —$SR_3$, wherein $R_3$ and $R_4$ are independently selected from the group formed by H, a non-cyclic substituted or unsubstituted aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl; and with the condition that $R_1$ and $R_2$ are not α-amino acids.

Groups $R_1$ and $R_2$ are respectively bound to the amino-terminal (N-terminal) and carboxy-terminal (C-terminal) of the peptide sequences.

In accordance with a preferred embodiment of this invention $R_1$ is selected from the group formed by H or $R_5$—CO—, wherein $R_5$ is selected from the group formed by substituted or unsubstituted $C_1$-$C_{24}$ alkyl radical, substituted or unsubstituted $C_2$-$C_{24}$ alkenyl, substituted or unsubstituted $C_2$-$C_{24}$ alkynyl, substituted or unsubstituted $C_3$-$C_{24}$ cycloalkyl, substituted or unsubstituted $C_5$-$C_{24}$ cycloalkenyl, substituted or unsubstituted $C_8$-$C_{24}$ cycloalkynyl, substituted or unsubstituted $C_6$-$C_{30}$ aryl, substituted or unsubstituted $C_7$-$C_{24}$ aralkyl, substituted or unsubstituted heterocyclyl ring of 3-10 members, and substituted or unsubstituted heteroarylalkyl of 2 to 24 carbon atoms and 1 to 3 atoms other than carbon and an alkyl chain of 1 to 6 carbon atoms. More preferably, $R_1$ is selected from H, acetyl, tert-butanoyl, hexanoyl, 2-methylhexanoyl, cyclohexanecarboxyl, octanoyl, decanoyl, lauroyl myristoyl, palmitoyl, stearoyl, oleoyl and linoleoyl. Even more preferably, $R_1$ is H, acetyl, lauroyl, myristoyl or palmitoyl. In an even more preferred embodiment, $R_1$ is acetyl or palmitoyl.

In accordance with another preferred embodiment, $R_2$ is —$NR_3R_4$, —$OR_3$ or —$SR_3$ wherein $R_3$ and $R_4$ are independently selected from the group formed by H, substituted or unsubstituted $C_1$-$C_{24}$ alkyl, substituted or unsubstituted $C_2$-$C_{24}$ alkenyl, substituted or unsubstituted $C_2$-$C_{24}$ alkynyl, substituted or unsubstituted $C_3$-$C_{24}$ cycloalkyl, substituted or unsubstituted $C_5$-$C_{24}$ cycloalkenyl, substituted or unsubstituted $C_8$-$C_{24}$ cycloalkynyl, substituted or unsubstituted $C_6$-$C_{30}$ aryl, substituted or unsubstituted $C_7$-$C_{24}$ aralkyl, substituted or unsubstituted heterocyclyl ring of 3-10 members, and substituted or unsubstituted heteroarylalkyl of 2 to 24 carbon atoms and 1 to 3 atoms other than carbon wherein the alkyl chain is of 1 to 6 carbon atoms. Optionally, $R_3$ and $R_4$ can be bound by a saturated or unsaturated carbon-carbon bond, forming a cycle with the nitrogen atom. More preferably $R_2$ is —$NR_3R_4$ or —$OR_3$, wherein $R_3$ and $R_4$ are independently selected from the group formed by H, substituted or unsubstituted $C_1$-$C_{24}$ alkyl, substituted or unsubstituted $C_2$-$C_{24}$ alkenyl, substituted or unsubstituted $C_2$-$C_{24}$ alkynyl, substituted or unsubstituted $C_3$-$C_{10}$ cycloalkyl, substituted or unsubstituted $C_6$-$C_{15}$ aryl and substituted or unsubstituted heterocyclyl of 3-10 members, substituted or unsubstituted heteroarylalkyl with a ring of 3 to 10 members and an alkyl chain of 1 to 6 carbon atoms. More preferably $R_3$ and $R_4$ are selected from the group formed by H, methyl, ethyl, hexyl, dodecyl, or hexadecyl. Even more preferably $R_3$ is H and $R_4$ is selected from the group formed by H, methyl, ethyl, hexyl, dodecyl, or hexadecyl. In accordance with an even more preferred embodiment, $R_2$ is selected from —OH and —$NH_2$.

In accordance with another preferred embodiment of this invention, $R_1$ is selected from the group formed by H, acetyl, lauroyl, myristoyl or palmitoyl, $AA_1$ is -L-Ser-, $AA_2$ is -L-Ile-, $AA_3$ is -L-Tyr-, $AA_4$ is -L-Val-, $AA_5$ is -L-Ala-, $AA_6$ is -L-Thr- and $R_2$ is —$NR_3R_4$ or —$OR_3$ wherein $R_3$ and $R_4$ are independently selected from H, methyl, ethyl, hexyl, dodecyl and hexadecyl, preferably $R_2$ is —OH or —$NH_2$. More preferably, $R_1$ is acetyl or palmitoyl and $R_2$ is —$NH_2$. Even more preferably, n, m, p and q are 0.

In accordance with another preferred embodiment $R_1$ is selected from the group formed by H, acetyl, lauroyl, myristoyl or palmitoyl, $AA_1$ is -L-Ser-, $AA_2$ is -L-Val-, $AA_3$ is -L-Tyr-, $AA_4$ is -L-Val-, $AA_5$ is -L-Ala-, $AA_6$ is -L-Thr- and $R_2$ is —$NR_3R_4$ or —$OR_3$ wherein $R_3$ and $R_4$ are independently selected from H, methyl, ethyl, hexyl, dodecyl and hexadecyl, preferably $R_2$ is —OH or —$NH_2$. More preferably, $R_1$ is acetyl or palmitoyl and $R_2$ is —$NH_2$. Even more preferably, n, m, p and q are 0.

In accordance with another embodiment of this invention $R_1$ is selected from the group formed by H, acetyl, lauroyl, myristoyl or palmitoyl, $AA_1$ is -L-Ser-, $AA_2$ is -L-Ile-, $AA_3$ is -L-Val-, $AA_4$ is -L-Val-, $AA_5$ is -L-Gly-, $AA_6$ is -L-Thr- and $R_2$ is —$NR_3R_4$ or —$OR_3$ wherein $R_3$ and $R_4$ are independently selected from H, methyl, ethyl, hexyl, dodecyl and hexadecyl, preferably $R_2$ is —OH or —$NH_2$. More preferably, $R_1$ is acetyl or palmitoyl and $R_2$ is —$NH_2$. Even more preferably, n, m, p and q are 0.

In accordance with another embodiment of this invention $R_1$ is selected from the group formed by H, acetyl, lauroyl, myristoyl or palmitoyl, $AA_1$ is -L-Ser-, $AA_2$ is -L-Val-, $AA_3$ is -L-Val-, $AA_4$ is -L-Val-, $AA_5$ is -L-Arg-, $AA_6$ is -L-Thr- and $R_2$ is —$NR_3R_4$ or —$OR_3$ wherein $R_3$ and $R_4$ are independently selected from H, methyl, ethyl, hexyl, dodecyl and hexadecyl, preferably $R_2$ is —OH or —$NH_2$. More preferably, $R_1$ is acetyl or palmitoyl and $R_2$ is —$NH_2$. Even more preferably, n, m, p and q are 0.

In accordance with another embodiment of this invention $R_1$ is selected from the group formed by H, acetyl, lauroyl, myristoyl or palmitoyl, $AA_1$ is -L-His-, $AA_2$ is -L-Ile-, $AA_3$ is -L-Val-, $AA_4$ is -L-Val-, $AA_5$ is -L-Gly-, $AA_6$ is -L-Thr- and $R_2$ is —$NR_3R_4$ or —$OR_3$ wherein $R_3$ and $R_4$ are independently selected from H, methyl, ethyl, hexyl, dodecyl and hexadecyl, preferably $R_2$ is —OH or —$NH_2$. More preferably, $R_1$ is acetyl or palmitoyl and $R_2$ is —$NH_2$. Even more preferably, n, m, p and q are 0.

In accordance with another embodiment of this invention $R_1$ is selected from the group formed by H, acetyl, lauroyl, myristoyl and palmitoyl, preferably $R_1$ is selected from the group formed by H, acetyl and palmitoyl and $R_2$ is selected from the group formed by —OH and —$NH_2$.

In accordance with another embodiment of this invention n, m, p and q are 0.

Preferably, the peptides in formula (I) are selected from the group formed by:

| | |
|---|---|
| Ac-SEQ. ID NO. 1-$NH_2$ | Palm-SEQ. ID NO. 35-OH |
| Ac-SEQ. ID NO. 2-$NH_2$ | Palm-SEQ. ID NO. 36-OH |
| Ac-SEQ. ID NO. 3-$NH_2$ | Palm-SEQ. ID NO. 37-OH |
| Ac-SEQ. ID NO. 1-$NH_2$ | Palm-SEQ. ID NO. 38-OH |
| Ac-SEQ. ID NO. 4-$NH_2$ | Palm-SEQ. ID NO. 39-OH |
| Ac-SEQ. ID NO. 5-$NH_2$ | Palm-SEQ. ID NO. 40OH |
| Ac-SEQ. ID NO. 6-$NH_2$ | Palm-SEQ. ID NO. 41-OH |
| Ac-SEQ. ID NO. 7-$NH_2$ | Palm-SEQ. ID NO. 42-OH |
| Ac-SEQ. ID NO. 8-$NH_2$ | Palm-SEQ. ID NO. 43-OH |
| Ac-SEQ. ID NO. 9-$NH_2$ | Palm-SEQ. ID NO. 44-OH |

| | |
|---|---|
| Ac-SEQ. ID NO. 10-NH₂ | Palm-SEQ. ID NO. 45-OH |
| Ac-SEQ. ID NO. 11-NH₂ | Palm-SEQ. ID NO. 46-OH |
| Ac-SEQ. ID NO. 12-NH₂ | Palm-SEQ. ID NO. 47-OH |
| Ac-SEQ. ID NO. 13-NH₂ | Palm-SEQ. ID NO. 48-OH |
| Ac-SEQ. ID NO. 14-NH₂ | Palm-SEQ. ID NO. 3-NH₂ |
| Ac-SEQ. ID NO. 15-NH₂ | Palm-SEQ. ID NO. 1-NH₂ |
| Ac-SEQ. ID NO. 16-NH₂ | Palm-SEQ. ID NO. 4-NH₂ |
| Ac-SEQ. ID NO. 2-NH₂ | Palm-SEQ. ID NO. 5-NH₂ |
| Ac-SEQ. ID NO. 17-NH₂ | Palm-SEQ. ID NO. 6-NH₂ |
| Ac-SEQ. ID NO. 18-NH₂ | Palm-SEQ. ID NO. 7-NH₂ |
| Ac-SEQ. ID NO. 19-NH₂ | Palm-SEQ. ID NO. 8-NH₂ |
| Ac-SEQ. ID NO. 20-NH₂ | Palm-SEQ. ID NO. 9-NH₂ |
| Ac-SEQ. ID NO. 21-NH₂ | Palm-SEQ. ID NO. 10-NH₂ |
| Ac-SEQ. ID NO. 22-NH₂ | Palm-SEQ. ID NO. 11-NH₂ |
| Ac-SEQ. ID NO. 23-NH₂ | Palm-SEQ. ID NO. 12-NH₂ |
| Ac-SEQ. ID NO. 24-NH₂ | Palm-SEQ. ID NO. 13-NH₂ |
| Ac-SEQ. ID NO. 25-NH₂ | Palm-SEQ. ID NO. 14-NH₂ |
| Ac-SEQ. ID NO. 26-NH₂ | Palm-SEQ. ID NO. 15-NH₂ |
| Ac-SEQ. ID NO. 27-NH₂ | Palm-SEQ. ID NO. 16-NH₂ |
| Ac-SEQ. ID NO. 28-NH₂ | Palm-SEQ. ID NO. 2-NH₂ |
| Ac-SEQ. ID NO. 29-NH₂ | Palm-SEQ. ID NO. 17-NH₂ |
| Ac-SEQ. ID NO. 30-NH₂ | Palm-SEQ. ID NO. 18-NH₂ |
| Ac-SEQ. ID NO. 31-NH₂ | Palm-SEQ. ID NO. 19-NH₂ |
| Ac-SEQ. ID NO. 32-NH₂ | Palm-SEQ. ID NO. 20-NH₂ |
| Ac-SEQ. ID NO. 33-NH₂ | Palm-SEQ. ID NO. 21-NH₂ |
| Ac-SEQ. ID NO. 34-NH₂ | Palm-SEQ. ID NO. 22-NH₂ |
| Ac-SEQ. ID NO. 35-NH₂ | Palm-SEQ. ID NO. 23-NH₂ |
| Ac-SEQ. ID NO. 36-NH₂ | Palm-SEQ. ID NO. 24-NH₂ |
| Ac-SEQ. ID NO. 37-NH₂ | Palm-SEQ. ID NO. 25-NH₂ |
| Ac-SEQ. ID NO. 38-NH₂ | Palm-SEQ. ID NO. 26-NH₂ |
| Ac-SEQ. ID NO. 39-NH₂ | Palm-SEQ. ID NO. 27-NH₂ |
| Ac-SEQ. ID NO. 40-NH₂ | Palm-SEQ. ID NO. 28-NH₂ |
| Ac-SEQ. ID NO. 41-NH₂ | Palm-SEQ. ID NO. 29-NH₂ |
| Ac-SEQ. ID NO. 42-NH₂ | Palm-SEQ. ID NO. 30-NH₂ |
| Ac-SEQ. ID NO. 43-NH₂ | Palm-SEQ. ID NO. 31-NH₂ |
| Ac-SEQ. ID NO. 44-NH₂ | Palm-SEQ. ID NO. 32-NH₂ |
| Ac-SEQ. ID NO. 45-NH₂ | Palm-SEQ. ID NO. 33-NH₂ |
| Ac-SEQ. ID NO. 46-NH₂ | Palm-SEQ. ID NO. 34-NH₂ |
| Ac-SEQ. ID NO. 47-NH₂ | Palm-SEQ. ID NO. 35-NH₂ |
| Ac-SEQ. ID NO. 48-NH₂ | Palm-SEQ. ID NO. 36-NH₂ |
| Ac-SEQ. ID NO. 3-OH | Palm-SEQ. ID NO. 37-NH₂ |
| Ac-SEQ. ID NO. 1-OH | Palm-SEQ. ID NO. 38-NH₂ |
| Ac-SEQ. ID NO. 4-OH | Palm-SEQ. ID NO. 39-NH₂ |
| Ac-SEQ. ID NO. 5-OH | Palm-SEQ. ID NO. 40-NH₂ |
| Ac-SEQ. ID NO. 6-OH | Palm-SEQ. ID NO. 41-NH₂ |
| Ac-SEQ. ID NO. 7-OH | Palm-SEQ. ID NO. 42-NH₂ |
| Ac-SEQ. ID NO. 8-OH | Palm-SEQ. ID NO. 43-NH₂ |
| Ac-SEQ. ID NO. 9-OH | Palm-SEQ. ID NO. 44-NH₂ |
| Ac-SEQ. ID NO. 10-OH | Palm-SEQ. ID NO. 45-NH₂ |
| Ac-SEQ. ID NO. 11-OH | Palm-SEQ. ID NO. 46-NH₂ |
| Ac-SEQ. ID NO. 12-OH | Palm-SEQ. ID NO. 47-NH₂ |
| Ac-SEQ. ID NO. 13-OH | Palm-SEQ. ID NO. 48-NH₂ |
| Ac-SEQ. ID NO. 14-OH | Ac-SEQ. ID NO. 3-NH—(CH₂)₁₅—CH₃ |
| Ac-SEQ. ID NO. 15-OH | Ac-SEQ. ID NO. 1-NH—(CH₂)₁₅—CH₃ |
| Ac-SEQ. ID NO. 16-OH | Ac-SEQ. ID NO. 4-NH—(CH₂)₁₅—CH₃ |
| Ac-SEQ. ID NO. 2-OH | Ac-SEQ. ID NO. 5-NH—(CH₂)₁₅—CH₃ |
| Ac-SEQ. ID NO. 17-OH | Ac-SEQ. ID NO. 6-NH—(CH₂)₁₅—CH₃ |
| Ac-SEQ. ID NO. 18-OH | Ac-SEQ. ID NO. 7-NH—(CH₂)₁₅—CH₃ |
| Ac-SEQ. ID NO. 19-OH | Ac-SEQ. ID NO. 8-NH—(CH₂)₁₅—CH₃ |
| Ac-SEQ. ID NO. 20-OH | Ac-SEQ. ID NO. 9-NH—(CH₂)₁₅—CH₃ |
| Ac-SEQ. ID NO. 21-OH | Ac-SEQ. ID NO. 10-NH—(CH₂)₁₅—CH₃ |
| Ac-SEQ. ID NO. 22-OH | Ac-SEQ. ID NO. 11-NH—(CH₂)₁₅—CH₃ |
| Ac-SEQ. ID NO. 23-OH | Ac-SEQ. ID NO. 12-NH—(CH₂)₁₅—CH₃ |
| Ac-SEQ. ID NO. 24-OH | Ac-SEQ. ID NO. 13-NH—(CH₂)₁₅—CH₃ |
| Ac-SEQ. ID NO. 25-OH | Ac-SEQ. ID NO. 14-NH—(CH₂)₁₅—CH₃ |
| Ac-SEQ. ID NO. 26-OH | Ac-SEQ. ID NO. 15-NH—(CH₂)₁₅—CH₃ |
| Ac-SEQ. ID NO. 27-OH | Ac-SEQ. ID NO. 16-(CH₂)₁₅—CH₃ |
| Ac-SEQ. ID NO. 28-OH | Ac-SEQ. ID NO. 2-NH—(CH₂)₁₅—CH₃ |
| Ac-SEQ. ID NO. 29-OH | Ac-SEQ. ID NO. 17-NH—(CH₂)₁₅—CH₃ |
| Ac-SEQ. ID NO. 30-OH | Ac-SEQ. ID NO. 18-NH—(CH₂)₁₅—CH₃ |
| Ac-SEQ. ID NO. 31-OH | Ac-SEQ. ID NO. 19-NH—(CH₂)₁₅—CH₃ |
| Ac-SEQ. ID NO. 32-OH | Ac-SEQ. ID NO. 20-NH—(CH₂)₁₅—CH₃ |
| Ac-SEQ. ID NO. 33-OH | Ac-SEQ. ID NO. 21-NH—(CH₂)₁₅—CH₃ |
| Ac-SEQ. ID NO. 34-OH | Ac-SEQ. ID NO. 22-NH—(CH₂)₁₅—CH₃ |
| Ac-SEQ. ID NO. 35-OH | Ac-SEQ. ID NO. 23-NH—(CH₂)₁₅—CH₃ |
| Ac-SEQ. ID NO. 36-OH | Ac-SEQ. ID NO. 24-NH—(CH₂)₁₅—CH₃ |
| Ac-SEQ. ID NO. 37-OH | Ac-SEQ. ID NO. 25-NH—(CH₂)₁₅—CH₃ |
| Ac-SEQ. ID NO. 38-OH | Ac-SEQ. ID NO. 26-NH—(CH₂)₁₅—CH₃ |
| Ac-SEQ. ID NO. 39-OH | Ac-SEQ. ID NO. 27-NH—(CH₂)₁₅—CH₃ |
| Ac-SEQ. ID NO. 40-OH | Ac-SEQ. ID NO. 28-NH—(CH₂)₁₅—CH₃ |
| Ac-SEQ. ID NO. 41-OH | Ac-SEQ. ID NO. 29-NH—(CH₂)₁₅—CH₃ |
| Ac-SEQ. ID NO. 42-OH | Ac-SEQ. ID NO. 30-NH—(CH₂)₁₅—CH₃ |
| Ac-SEQ. ID NO. 43-OH | Ac-SEQ. ID NO. 31-NH—(CH₂)₁₅—CH₃ |
| Ac-SEQ. ID NO. 404-OH | Ac-SEQ. ID NO. 32-NH—(CH₂)₁₅—CH₃ |
| Ac-SEQ. ID NO. 45-OH | Ac-SEQ. ID NO. 33-NH—(CH₂)₁₅—CH₃ |
| Ac-SEQ. ID NO. 46-OH | Ac-SEQ. ID NO. 34-NH—(CH₂)₁₅—CH₃ |
| Ac-SEQ. ID NO. 47-OH | Ac-SEQ. ID NO. 35-NH—(CH₂)₁₅—CH₃ |
| Ac-SEQ. ID NO. 48-OH | Ac-SEQ. ID NO. 36-NH—(CH₂)₁₅—CH₃ |
| Palm-SEQ. ID NO. 3-OH | Ac-SEQ. ID NO. 37-NH—(CH₂)₁₅—CH₃ |
| Palm-SEQ. ID NO. 1-OH | Ac-SEQ. ID NO. 38-NH—(CH₂)₁₅—CH₃ |
| Palm-SEQ. ID NO. 4-OH | Ac-SEQ. ID NO. 39-NH—(CH₂)₁₅—CH₃ |
| Palm-SEQ. ID NO. 5-OH | Ac-SEQ. ID NO. 40-NH—(CH₂)₁₅—CH₃ |
| Palm-SEQ. ID NO. 6-OH | Ac-SEQ. ID NO. 41-NH—(CH₂)₁₅—CH₃ |
| Palm-SEQ. ID NO. 7-OH | Ac-SEQ. ID NO. 42-NH—(CH₂)₁₅—CH₃ |
| Palm-SEQ. ID NO. 8-OH | Ac-SEQ. ID NO. 43-NH—(CH₂)₁₅—CH₃ |
| Palm-SEQ. ID NO. 9-OH | Ac-SEQ. ID NO. 44-NH—(CH₂)₁₅—CH₃ |
| Palm-SEQ. ID NO. 10-OH | Ac-SEQ. ID NO. 45-NH—(CH₂)₁₅—CH₃ |
| Palm-SEQ. ID NO. 11-OH | Ac-SEQ. ID NO. 46-NH—(CH₂)₁₅—CH₃ |
| Palm-SEQ. ID NO. 12-OH | Ac-SEQ. ID NO. 47-NH—(CH₂)₁₅—CH₃ |
| Palm-SEQ. ID NO. 13-OH | Ac-SEQ. ID NO. 48-NH—(CH₂)₁₅—CH₃ |
| Palm-SEQ. ID NO. 14-OH | Ac-SEQ. ID NO. 49-NH₂ |
| Palm-SEQ. ID NO. 15-OH | Ac-SEQ. ID NO. 50-NH₂ |
| Palm-SEQ. ID NO. 16-OH | Ac-SEQ. ID NO. 49-Thr-OH |
| Palm-SEQ. ID NO. 2-OH | Ac-SEQ. ID NO. 51-NH₂ |
| Palm-SEQ. ID NO. 17-OH | Palm-SEQ. ID NO. 52-NH₂ |
| Palm-SEQ. ID NO. 18-OH | Ac-SEQ. ID NO. 53-OH |
| Palm-SEQ. ID NO. 19-OH | Ac-SEQ. ID NO. 54-NH₂ |
| Palm-SEQ. ID NO. 20-OH | Ac-SEQ. ID NO. 55-NH₂ |
| Palm-SEQ. ID NO. 21-OH | Ac-SEQ. ID NO. 56-NH₂ |
| Palm-SEQ. ID NO. 22-OH | Palm-SEQ. ID NO. 57-NH₂ |
| Palm-SEQ. ID NO. 23-OH | Ac-SEQ. ID NO. 58-NH₂ |
| Palm-SEQ. ID NO. 24-OH | Ac-SEQ. ID NO. 59-NH₂ |
| Palm-SEQ. ID NO. 25-OH | Ac-SEQ. ID NO. 60-NH₂ |
| Palm-SEQ. ID NO. 26-OH | Ac-SEQ. ID NO. 61-OH |
| Palm-SEQ. ID NO. 27-OH | Palm-SEQ. ID NO. 62-NH₂ |
| Palm-SEQ. ID NO. 28-OH | Ac-SEQ. ID NO. 63-NH₂ |
| Palm-SEQ. ID NO. 29-OH | Palm-SEQ. ID NO. 64-NH₂ |
| Palm-SEQ. ID NO. 30-OH | Ac-SEQ. ID NO. 65-OH |
| Palm-SEQ. ID NO. 31-OH | PalmSEQ. ID NO. 66-OH |
| Palm-SEQ. ID NO. 32-OH | Ac-SEQ. ID NO. 67-NH₂ |
| Palm-SEQ. ID NO. 33-OH | Ac-SEQ. ID NO. 68-NH₂ |
| Palm-SEQ. ID NO. 34-OH | Palm-SEQ. ID NO. 69-NH₂ |
| Palm-SEQ. ID NO. 70-OH | Ac-SEQ. ID NO. 71-OH | their stereoisomers, mixtures thereof and/or their cosmetically or pharmaceutically acceptable salts, where:

SEQ. ID No. 1 is Ser-Ile-Tyr-Val-Ala-Thr; SEQ. ID No.2 is Ser-Val-Val-Val-Arg-Thr; SEQ. ID No. 3 is His-Ile-Tyr-Val-Ala-Thr; SEQ. ID No. 4 is His-Val-Tyr-Val-Ala-Thr; SEQ. ID No. 5 is Ser-Val-Tyr-Val-Ala-Thr; SEQ. ID No. 6 is His-Ile-Val-Val-Ala-Thr; SEQ. ID No. 7 is Ser-Ile-Val-Val-Ala-Thr; SEQ. ID No. 8 is His-Val-Val-Val-Ala-Thr; SEQ. ID No. 9 is Ser-Val-Val-Val-Ala-Thr; SEQ. ID No. 10 is His-Ile-Tyr-Val-Arg-Thr; SEQ. ID No. 11 is Ser-Ile-Tyr-Val-Arg-Thr; SEQ. ID No. 12 is His-Val-Tyr-Val-Arg-Thr; SEQ. ID No. 13 is Ser-Val-Tyr-Val-Arg-Thr; SEQ. ID No. 14 is His-Ile-Val-Val-Arg-Thr; SEQ. ID No. 15 is Ser-Ile-Val-Val-Arg-Thr, SEQ. ID No. 16 is His-Val-Val-Val-Arg-Thr; SEQ. ID No. 17 is His-Ile-Tyr-Val-Gly-Thr; SEQ. ID No. 18 is Ser-Ile-Tyr-Val-Gly-Thr; SEQ. ID No. 19 is His-Val-Tyr-Val-Gly-Thr; SEQ. ID No. 20 is Ser-Val-Tyr-Val-Gly-Thr; SEQ. ID No. 21 is His-Ile-Val-Val-Gly-Thr; SEQ. ID No. 22 is Ser-Ile-Val-Val-Gly-Thr; SEQ. ID No. 23 is His-Val-Val-Val-Gly-Thr; SEQ. ID No. 24 is Ser-Val-Val-Val-Gly-Thr; SEQ. ID No. 25 is His-Ile-Tyr-Val-Ala-Val; SEQ. ID No. 26 is Ser-Ile-Tyr-Val-Ala-Val; SEQ. ID No. 27 is His-Val-Tyr-Val-Ala-Val; SEQ. ID No. 28 is Ser-Val-Tyr-Val-Ala-Val; SEQ. ID No. 29 is His-Ile-Val-Val-Ala-Val; SEQ. ID No. 30 is Ser-Ile-Val-Val-Ala-Val; SEQ. ID No. 31 is His-Val-Val-Val-Ala-Val; SEQ. ID No. 32 is Ser-Val-Val-Val-Ala-Val; SEQ. ID No. 33 is His-Ile-Tyr-Val-Arg-Val; SEQ. ID No. 34 is Ser-Ile-Tyr-Val-Arg-Val; SEQ. ID No. 35 is His-Val-Tyr-Val-Arg-Val; SEQ.

ID No. 36 is Ser-Val-Tyr-Val-Arg-Val; SEQ. ID No. 37 is His-Ile-Val-Val-Arg-Val; SEQ. ID No. 38 is Ser-Ile-Val-Val-Arg-Val; SEQ. ID No. 39 is His-Val-Val-Val-Arg-Val; SEQ. ID No. 40 is Ser-Val-Val-Val-Arg-Val; SEQ. ID No. 41 is His-Ile-Tyr-Val-Gly-Val; SEQ. ID No. 42 is Ser-Ile-Tyr-Val-Gly-Val; SEQ. ID No. 43 is His-Val-Tyr-Val-Gly-Val; SEQ. ID No. 44 is Ser-Val-Tyr-Val-Gly-Val; SEQ. ID No. 45 is His-Ile-Val-Val-Gly-Val; SEQ. ID No. 46 is Ser-Ile-Val-Val-Gly-Val; SEQ. ID No. 47 is His-Val-Val-Val-Gly-Val; SEQ. ID No. 48 is Ser-Val-Val-Val-Gly-Val; SEQ. ID No. 49 is Gly-Ser-Ile-Tyr-Val-Ala-Thr; SEQ. ID No. 50 is Ser-Ile-Tyr-Val-Ala-Thr-Ala; SEQ. ID No. 51 is Gly-Gly-Ser-Ile-Tyr-Val-Ala-Thr; SEQ. ID No. 52 is Ala-Ser-Ile-Tyr-Val-Ala-Thr-Ala; SEQ. ID No. 53 is Gly-Gly-Ser-Val-Tyr-Val-Ala-Thr; SEQ. ID No. 54 is Ala-Ser-Val-Tyr-Val-Ala-Thr; SEQ. ID No. 55 is Gly-Ser-Val-Tyr-Val-Ala-Thr; SEQ. ID No. 56 is Ser-Val-Tyr-Val-Ala-Thr-Ala-Ala; SEQ. ID No. 57 is Gly-Ser-Val-Tyr-Val-Ala-Thr-Ala; SEQ. ID No. 58 is Tyr-Ser-Ile-Val-Val-Gly-Thr; SEQ. ID No. 59 is Thr-Gly-Ser-Ile-Val-Val-Gly-Thr; SEQ. ID No. 60 is Gly-Ser-Ile-Val-Val-Gly-Thr-His; SEQ. ID No. 61 is Ser-Ile-Val-Val-Gly-Thr-Ala-Gly; SEQ. ID No. 62 is Gly-Ser-Ile-Val-Val-Gly-Thr-Gly; SEQ. ID No. 63 is Ser-Val-Val-Val-Arg-Thr-Ile; SEQ. ID No. 64 is Ser-Val-Val-Val-Arg-Thr-Ile-Val; SEQ. ID No. 65 is Gly-Ser-Val-Val-Val-Arg-Thr; SEQ. ID No. 66 is Gly-Gly-Ser-Val-Val-Val-Arg-Thr; SEQ. ID No. 67 is Gly-Ser-Val-Val-Val-Arg-Thr-Gly; SEQ. ID No. 68 is Ala-His-Ile-Val-Val-Gly-Thr; SEQ. ID No. 69 is Gly-His-Ile-Val-Val-Gly-Thr-Ala; SEQ. ID No. 70 is His-Ile-Val-Val-Gly-Thr-Leu-Ala; and SEQ. ID No. 71 is Ala-Leu-His-Ile-Val-Val-Gly-Thr.

The peptides of this invention can exist as stereoisomers or mixtures of stereoisomers; for example, the amino acids which comprise them can have the configuration L-, D-, or be racemic independently of each other. Therefore, it is possible to obtain isomeric mixtures as well as racemic mixtures or diastereomer mixtures, or pure diastereomers or enantiomers, depending on the number of asymmetric carbons and on which isomers or isomeric mixtures are present. The preferred structures of the peptides of the invention are pure isomers, i.e., enantiomers or diastereomers.

For example, when it is stated that $AA_1$ can be Ser, it is understood that $AA_1$ is selected from -L-Ser-, -D-Ser- or mixtures of both, racemic or non-racemic. In the same way, when it is said that $AA_2$ can be -Ile-, it is understood that it can be -L-Ile-, -D-Ile- or mixtures of both, racemic or non-racemic. The preparation process described in this document enable the person skilled in the art to obtain each of the stereoisomers of the peptide of the invention by choosing the amino acid with the right configuration.

In the context of this invention, the term "amino acids" includes the amino acids codified by the genetic code as well as uncodified amino acids, whether they are natural or not. Examples of uncodified amino acids are, without restriction, citrulline, ornithine, sarcosine, desmosine, norvaline, 4-aminobutyric acid, 2-aminobutyric acid, 2-aminoisobutyric acid, 6-aminohexanoic acid, 1-naphthylalanine, 2-naphthylalanine, 2-aminobenzoic acid, 4 aminobenzoic acid, 4-chlorophenylalanine, 2,3-diaminopropionic acid, 2,4 diaminobutyric acid, cycloserine, carnitine, cysteine, penicillamine, pyroglutamic acid, thienylalanine, hydroxyproline, allo-isoleucine, allo-threonine, isonipecotic acid, isoserine, phenylglycine, statin, β-alanine, norleucine, N-methylamino acids, α-amino acids and β-amino acids, among others, as well as their derivatives. A list of unnatural amino acids can be found in the article "*Unusual amino acids in peptide synthesis*" by D. C. Roberts and F. Vellaccio, in *The Peptides*, Vol. 5 (1983), *Chapter VI, Gross E. and Meienhofer J., Eds.*, Academic Press, New York, USA or in the commercial catalogues of the companies specialized in the field.

In the context of this invention, when n, m, p or q are not 0 it is clearly understood that the nature of W, X, Y and/or Z does not hinder the activity of the peptides of the invention, but that it contributes to the modulation of PGC-1α or has no effect on PGC-1α.

The cosmetically and pharmaceutically acceptable salts of the peptides provided by this invention are also found within the field of this invention. The term "cosmetically or pharmaceutically acceptable salts" means a salt recognized for its use in animals and more specifically in human beings, and includes salts used to form base addition salts, either they are inorganic, such as and not restricted to, lithium, sodium, potassium, calcium, magnesium, manganese, copper, zinc or aluminium among others, either they are organic, such as and not restricted to, ethylamine, diethylamine, ethylenediamine, ethanolamine, diethanolamine, arginine, lysine, histidine or piperazine among others, or acid addition salts, either they are organic, such as and not restricted to, acetate, citrate, lactate, malonate, maleate, tartrate, fumarate, benzoate, aspartate, glutamate, succinate, oleate, trifluoroacetate, oxalate, pamoate or gluconate among others, or inorganic, such as and not restricted to, chloride, sulfate, borate or carbonate, among others. The nature of the salt is not critical, provided that it is cosmetically or pharmaceutically acceptable. The cosmetically or pharmaceutically acceptable salts of the peptides of the invention can be obtained by the conventional methods, well known in the prior art [Berge S. M. et al., "*Pharmaceutical Salts*", *J. Pharm. Sci.*, (1977), 66, 1-19].

In another particular aspect, this invention relates to a peptide of general formula (I), its stereoisomers, mixtures thereof and/or its cosmetically or pharmaceutically acceptable salts, as described in this invention, for its use in the modulation of PGC-1α.

In another particular aspect, this invention relates to a peptide of general formula (I), its stereoisomers, mixtures thereof and/or its cosmetically or pharmaceutically acceptable salts, as described in this invention, for its use in the modulation of the receptor PPARγ.

In another particular aspect, this invention refers to a peptide of general formula (I), its stereoisomers, mixtures thereof and/or its cosmetically or pharmaceutically acceptable salts, as described in this invention, for its use in the treatment and/or care of conditions, disorders and/or diseases selected from the group formed by metabolic diseases and/or disorders such as diseases related to lipid metabolism, changes to gluconeogenesis, obesity, type 2 diabetes, cellulitis, gynecomastia, pseudogynecomastia, lipoatrophy, semicircular lipoatrophy, lipodystrophy, aging, photoaging, cutaneous traumas, reepithelialization of injuries, dehydration of the skin, xerosis, keratinization disorders, callouses, hard skin, psoriasis, lichen planus, skin lesions associated with lupus, dermatitis, atopic dermatitis, seborrheic dermatitis, senile dermatitis, dandruff, cradle cap, seborrhea, hyperseborrhea of acne, solar dermatitis seborrheic keratosis, senile keratosis, actinic keratosis, photoinduced keratosis, follicular keratosis, acne vulgar, nevus, keloids, change in the function of fibroblasts, nodular fascitis, scleroderma, Dupuytren's contracture, fibrous scar formation, disorders of the sebaceous glands, acne rosacea, polymorphic acne, comedones, polymorphous, rosacea, nodulocystic acne, conglobate acne, senile acne, ichthyosis, Darier's disease, keratodermia palmoplantaris, leukoplakia, mucosal lichen, cutaneous lichen, cutaneous psoriasis, mucosal psoriasis, nail psoriasis, psoriatic rheumatism, eczema, common warts, flat warts, epidermodysplasia verruciformis, oral papillomatosis, lupus erythematosus, bullous diseases, bullous pemphigoid, scleroderma, actinic keratosis, pigmentation disorders, vitiligo, alopecia greata, Alzheimer's disease, Parkinson's disease, Huntington's disease, Pick's disease, Kuf's disease, Lewy Body disease, neurofibrillary tangles, Rosenthal fibers, Mallory's hyaline, senile dementia, myasthenia gravis, Gilles de la Tourette syndrome, multiple sclerosis, amyotrophic lateral sclerosis, progressive supranuclear palsy, epilepsy, Creutzfeldt-Jakob disease, deafness-dystonia syndrome, Leigh's disease, Leber's hereditary optic neuropathy, parkinsonism, dystonia, motor neurone disease, neuropathy syndrome, ataxia and retinitis pigmentosa, maternally inherited Leigh's disease, Friedreich's ataxia, hereditary spastic paraplegia, Mohr-Tranebjaerg syndrome, Wilson's disease, sporadic Alzheimer's disease, sporadic amyotrophic lateral sclerosis, sporadic Parkinson's disease, changes in autonomic function, hypertension, sleep disorders, neuropsychiatric disorders, depression, schizophrenia, schizoaffective disorder, Korsakoff psychosis, mania, anxiety disorders, phobic disorder, learning or memory disorders, amnesia or age-related memory loss, attention deficit disorder, dysthymic disorder, major depressive disorder, obsessive-compulsive disorder, disorders due to psychoactive substance use, panic disorder, affective bipolar disorder, migraines, hyperactivity disorders and movement disorders.

In another more particular aspect, this invention refers to a peptide of general formula (I), its stereoisomers, mixtures thereof and/or its cosmetically or pharmaceutically acceptable salts, as described in this invention, for its use in the treatment and/or care of the skin.

In another more particular aspect, this invention refers to a peptide of general formula (I), its stereoisomers, mixtures thereof and/or its cosmetically or pharmaceutically acceptable salts, as described in this invention, which increases or reduces the volume of the adipose tissue, preferably of the subcutaneous adipose tissue, more preferably of the subcutaneous adipose tissue of the thighs, breasts, lower part of the neck, neckline, buttocks, face, lips, cheeks, eyelids and/or hands.

In another more particular aspect, this invention refers to a peptide of general formula (I), its stereoisomers, mixtures thereof and/or its cosmetically or pharmaceutically acceptable salts, as described in this invention, which increases or reduces the triglyceride content of the adipose tissue, preferably of the subcutaneous adipose tissue, more preferably of the subcutaneous adipose tissue of the thighs, breasts, lower part of the neck, neckline, buttocks, face, lips, cheeks, eyelids and/or hands.

In another more particular aspect, this invention refers to a peptide of general formula (I), its stereoisomers, mixtures thereof and/or its cosmetically or pharmaceutically acceptable salts, as described in this invention, which reduces, prevents or delays the appearance of cellulitis.

In another aspect, this invention refers to a peptide of general formula (I), its stereoisomers, mixtures thereof and/or its cosmetically or pharmaceutically acceptable salts, as described in this invention, for the treatment and/or care of the skin which reduces, delays and/or prevents the signs of aging and/or photoaging.

In another more particular aspect, this invention refers to a peptide of general formula (I), its stereoisomers, mixtures thereof and/or its cosmetically or pharmaceutically acceptable salts, as described in this invention, which increases the temperature of the skin.

In another more particular aspect, this invention refers to a peptide of general formula (I), its stereoisomers, mixtures thereof and/or its cosmetically or pharmaceutically acceptable salts, as described in this invention, which is topically, transdermally, orally or parenterally applied.

In another more particular aspect, this invention refers to a peptide of general formula (I), its stereoisomers, mixtures thereof and/or its cosmetically or pharmaceutically acceptable salts, as described in this invention, in which the topical or transdermal application is performed by iontophoresis, sonophoresis, electroporation, mechanical pressure, osmotic pressure gradient, occlusive cure, microinjections, by needle-free injections by means of pressure, by microelectric patches, face masks or any combination thereof.

In another more particular aspect, the treatment and/or care is carried out by oral administration.

Preparation Process

Synthesis of the peptides of the invention, their stereoisomers or their cosmetically or pharmaceutically acceptable salts can be carried out according to conventional methods, known in the prior art, such as using solid phase peptide synthesis methods [Stewart J. M. and Young J. D., "*Solid Phase Peptide Synthesis, 2nd edition*", (1984), Pierce Chemical Company, Rockford, Ill.; Bodanzsky M., Bodanzsky A. "*The practice of Peptide Synthesis*", (1984), Springer Verlag, New Cork; Lloyd-Williams P., Albericio F., Giralt E. "*Chemical Approaches to the Synthesis of Peptides and Proteins*", (1997), *CRC*, Boca Raton, Fla., USA], synthesis in solution, a combination of the methods of solid phase synthesis and synthesis in solution or enzymatic synthesis [Kullmann W., "*Proteases as catalysts for enzymic syntheses of opioid peptides*", (1980), *J. Biol. Chem.*, 255, 8234-8238]. Peptides can also be made by biotechnological processes with the aim of producing the desired sequences, or by controlled hydrolysis of proteins with animal, fungal, or preferably plant origins, which free peptide fragments which contain, at least, the desired sequence.

For example, a method of obtaining the peptides of the invention of formula (I) comprises the stages of:
coupling of an amino acid, with the N-terminal end protected and the C-terminal end free, with an amino acid with the N-terminal end free and the C-terminal end protected or bound to a solid carrier;
elimination of the group protecting the N-terminal end;
repetition of the coupling sequence and elimination of the group protecting the N-terminal end until the desired peptide sequence is obtained;
elimination of the group protecting the C-terminal end or cleavage of the solid carrier.

Preferably, the C-terminal end is bound to a solid carrier and the process is carried out in solid phase and, therefore, comprises the coupling of an amino acid with the protected N-terminal end and the free C-terminal end with an amino acid with the N-terminal end free and the C-terminal end bound to a polymer carrier; elimination of the group protecting the N-terminal end; and repetition of this sequence as many times as is necessary to thus obtain the peptide of the desired length, finally followed by the cleavage of the synthesized peptide of the original polymeric carrier.

The functional groups of the side chains of the amino acids are maintained conveniently protected with temporary or permanent protective groups throughout synthesis, and can be unprotected simultaneously or orthogonally to the process of cleavage of the peptide of the polymeric carrier.

Alternatively, solid phase synthesis can be carried out using a convergent strategy coupling a peptide with the polymeric carrier or with an amino acid previously bound to the polymeric carrier. Convergent synthesis strategies are widely known by persons skilled in the art and are described in Lloyd-Williams P. et al, "*Convergent solid-phase peptide synthesis*", (1993), Tetrahedron, 49, 11065-11133.

The process can comprise the additional stages of the N-terminal and C-terminal ends deprotection and/or cleavage of the peptide of the polymeric carrier in an indiscriminant order, using standard processes and conditions known in the prior art, after which the functional groups of these ends can be modified. The optional modification of the N-terminal and C-terminal ends can be carried out with the peptide of formula (I) anchored to the polymeric carrier or once the peptide has been separated from the polymeric carrier.

Optionally, $R_1$ can be introduced by the reaction of the N-terminal end of the peptide of the invention with a $R_1$—X compound, wherein $R_1$ has the aforementioned meaning and X is a leaving group, such as and not restricted to, the tosyl group, the mesyl group and halogen groups among others; through a nucleophilic substitution reaction, in the presence of an adequate base and solvent, wherein the fragments that have the functional groups not involved in the N—C bond formation are suitably protected with temporary or permanent protective groups.

Optionally and/or additionally, the $R_2$ radicals can be introduced by the reaction of a compound $HR_2$ wherein $R_2$ is —$OR_3$, —$NR_3R_4$ or —$SR_3$, with a complementary fragment which corresponds to the peptide of formula (I) in which $R_2$ is —OH in the presence of an adequate solvent and a base such as, N,N-diisopropylethylamine (DIEA) or triethylamine or an additive such as 1-hydroxybenzotriazole (HOBt) or 1-hydroxyazabenzotriazole (HOAt) and a dehydrating agent, such as a carbodiimide, a uronium salt, a phosphonium salt or amidinium salt, among others, or by prior formation of an acyl halide with, for example, thionyl chloride, and thereby obtaining a peptide according to the invention of general formula (I), wherein the fragments that have the functional groups not involved in the N—C bond formation are suitably protected with temporary or permanent protective groups, or alternatively other $R_2$ radicals may be introduced by simultaneous incorporation to the peptide cleavage process from the polymeric carrier.

A person skilled in the art would easily understand that the deprotection/cleavage steps of the C-terminal and N-terminal ends and their subsequent derivatization can be performed in a different order, according to the processes known in the prior art.

The term "protective group" relates to a group which blocks an organic functional group and which can be removed in controlled conditions. The protective groups, their relative reactivities and the conditions in which they remain inert are known to the person skilled in the art.

Examples of representative protective groups for the amino group are amides, such as amide acetate, amide benzoate, amide pivalate; carbamates such as benzyloxycarbonyl (Cbz or Z), 2-chlorobenzyl (ClZ), para-nitrobenzyloxycarbonyl (pNZ), tert-butyloxycarbonyl (Boc), 2,2,2-trichloroethyloxycarbonyl (Troc), 2-(trimethylsilyl)ethyloxycarbonyl (Teoc), 9-fluorenylmethyloxycarbonyl (Fmoc) or allyloxycarbonyl (Alloc), trityl (Trt), methoxytrityl (Mtt), 2,4-dinitrophenyl (Dnp), N-[1-(4,4-dimethyl-2,6-dioxocyclohex-1-ylidene)ethyl (Dde), 1-(4,4-dimethyl-2,6-dioxocyclohexylidene)-3-methylbutyl (ivDde), 1-(1-adamantyl)-1-methylethoxycarbonyl (Adpoc), among others, preferably Boc or Fmoc.

Examples of representative protective groups for the carboxyl group are esters, such as the tert-butyl ester (tBu), allyl ester (All), triphenylmethyl ester (trityl ester, Trt), cyclohexyl ester (cHx), benzyl ester (Bzl), ortho-nitrobenzyl ester, para-nitrobenzyl ester, para-methoxybenzyl ester, trimethylsilyl-ethyl ester, 2-phenylisopropyl ester, fluorenylmethyl ester (Fm), 4-(N-[1-(4,4-dimethyl-2,6-dioxocyclohexylidene)-3-methylbutyl]amino)benzyl ester (Dmab), among others; preferred protective groups of the invention are the All, tBu, cHx, Bzl and Trt esters.

The side chains of the trifunctional amino acids can be protected during the synthetic process with temporary or permanent protective groups orthogonal to the protective groups of the N-terminal and C-terminal ends.

The hydroxyl group of the tyrosine side chain can be protected by the 2-bromobenzyloxycarbonyl (2-BrZ) group, tert-butyl (tBu), allyl (All), benzyl (BzI) or 2,6-dichlorobenzyl (2,6-diClZ), among others. The arginine side chain is protected by a protective group selected from the group formed by tosyl (Tos), 4-methoxy-2,3,6-trimethylbenzenesulfonyl (Mtr), Alloc, nitro, 2,2,4,6,7-pentamethyldihydrobenzofuran-5-sulfonyl (Pbf) and 2,2,5,7,8-pentamethylchroman-6-sulfonyl (Pmc). The histidine side chain is protected by a protective group selected from the group formed by Tos, Dnp, methyl (Me), Boc, benzyloxymethyl (Bom), Bzl, Fmoc, Mts, Trt and Mtt. The threonine and serine side chain is protected by a protective group selected from the group formed by tBu, Bzl, Trt and Ac.

In a preferred embodiment, the protective group strategy used is the strategy wherein the amino groups are protected by Boc, the carboxyl groups are protected by Bzl, cHex or All, the tyrosine side chain is protected by 2-BrZ or BzI, the threonine and serine side chains are protected by Bzl, the histidine side chain is protected by Tos or Bom and the arginine side chain is protected by the Tos group.

In another preferred embodiment, the protective group strategy used is the strategy wherein the amino groups are protected by Fmoc, the carboxyl groups are protected by tBu, All or Trt, the tyrosine side chain is protected by tBu, the threonine and serine side chains are protected by tBu, the histidine side chain is protected by Trt or Mtt and the arginine side chain is protected by the Pmc or Pbf group.

Examples of these and other additional protective groups, their introduction and removal, can be found in the literature [Atherton B. and Sheppard R. C., "*Solid Phase Peptide Synthesis: A practical approach*", (1989), IRL Oxford University Press]. The term "protective groups" also includes the polymeric carriers used in solid phase synthesis.

When synthesis takes place totally or partially in solid phase, the possible solid carriers used in the process of the invention involve polystyrene carriers, polyethylene glycol grafted to polystyrene and similar, such as and not restricted to, p-methylbenzhydrylamine resins (MBHA) [Matsueda G. R. et al, "*A p-methyl benzhydrylamine resin for improved solid-phase synthesis of peptide amides*". Peptides, (1981), 2, 45-50], 2-chlorotrityl resins [Barlos K. et al., "*Darstellung geschützter Peptid-Fragmente un ter Einsatz substituierter Triphenylmethyl-Harze*". Tetrahedron Lett., (1989), 30, 3943-3946; Barlos K. et al., "*Veresterung von partiell geschützten Peptid-Fragmenten mit Harzen. Einsatz von 2-Chlorotritylchlorid zur Synthese von Leu1-Gastrin I*". Tetrahedron Lett., (1989), 30, 3947-3951], TentaGel® resins (Rapp Polymere GmbH), ChemMatrix® resins (Matrix Innovation, Inc) and similar, which may or may not include a labile linker, such as 5-(4-aminomethyl-3,5-dimethoxyphenoxy) valeric acid (PAL) [Albericio F. et al., "*Preparation and application of the 5-(4-(9-fluorenylmethyloxycarbonyl)aminomethyl-3, 5-dimethoxy-phenoxy)valeric acid (PAL) handle for the solid-phase synthesis of C-terminal peptide amides under mild conditions*". J. Org. Chem., (1990), 55, 3730-3743], 2-(AM) [Rink H., "*Solid-phase synthesis of protected peptide fragments using a trialkoxy-diphenyl-methylester resin*". Tetrahedron Lett., (1987), 28, 3787-3790], Wang [Wang S. S., "p-Alkoxybenzyl Alcohol Resin and p-Alkoxybenzyloxycarbonylhydrazide Resin for Solid Phase Synthesis of Protected Peptide Fragments." J. Am. Chem. Soc., (1973), 95, 1328-1333] and similar, which enable simultaneous deprotection and cleavage of the peptide from the polymeric carrier.

Cosmetic or Pharmaceutical Compositions of the Invention

The peptides of the invention can be administered to modulate PGC-1α by any means which causes contact between the peptides and the site of action in a mammal's body, preferably that of a human being, and in the form of a composition which contains them.

In this regard, another aspect of the invention is a cosmetic or pharmaceutical composition which comprises at least one peptide of general formula (I), its stereoisomers, mixtures thereof, and/or its cosmetically or pharmaceutically acceptable salts together with at least one cosmetically or pharmaceutically acceptable adjuvant. These compositions can be prepared by conventional means known to persons skilled in the art ["Harry's Cosmeticology", Seventh edition, (1982), Wilkinson J. B., Moore R. J., ed. Longman House, Essex, GB].

The peptides of this invention have variable solubility in water, according to the nature of their sequence or any possible modifications in the N-terminal and/or C-terminal ends. Therefore, the peptides of this invention can be incorporated into the compositions by aqueous solution, and those which are not soluble in water can be solubilized in cosmetically or pharmaceutically acceptable conventional solvents such as and not restricted to, ethanol, propanol, isopropanol, propylene glycol, glycerine, butylene glycol or polyethylene glycol or any combination thereof.

The cosmetically or pharmaceutically effective amount of the peptides of the invention which should be administered, as well as their dosage, will depend on numerous factors, including age, state of the patient, the nature or severity of the condition, disorder or disease to be treated and/or cared for, the route and frequency of administration and of the particular nature of the peptides to be used.

"Cosmetically and pharmaceutically effective amount" is understood to mean a non-toxic but sufficient amount of the peptide or peptides of the invention to provide the desired effect. The peptides of the invention are used in the cosmetic or pharmaceutical composition of this invention at cosmetically or pharmaceutically effective concentrations to achieve the desired effect; in a preferred form with regards to the total weight of the composition, between 0.00000001% (in weight) and 20% (in weight); preferably between 0.000001% (in weight) and 15% (in weight), more preferably between 0.0001% (in weight) and 10% (in weight) and even more preferably between 0.0001% (in weight) and 5% (in weight).

The peptides of the invention or their functionally equivalent variants, their stereoisomers, mixtures thereof and/or their cosmetically or pharmaceutically acceptable salts, can also be incorporated into cosmetic or pharmaceutical delivery and/or sustained release systems.

The term "delivery systems" relates to a diluent, adjuvant, excipient or carrier with which the peptide of the invention is administered. These cosmetic or pharmaceutical carriers can be liquids, such as water, oils or surfactants, including those of petroleum, animal, plant or synthetic origin, such as and not restricted to, peanut oil, soybean oil, mineral oil, sesame oil, castor oil, polysorbates, sorbitan esters, ether sulfates, sulfates, betaines, glycosides, maltosides, fatty alcohols, nonoxynols, poloxamers, polyoxyethylenes, polyethylene glycols, dextrose, glycerol, digitonin and similar. A person skilled in the art knows the diluents which can be used in the different delivery systems in which the peptide of the invention can be administered.

The term "sustained release" is used in a conventional sense relating to a delivery system of a compound which provides the gradual release of this compound during a period of time and preferably, although not necessarily, with relatively constant compound release levels over a period of time.

Examples of delivery or sustained release systems include, without restriction, liposomes, mixed liposomes, oleosomes, niosomes, ethosomes, millicapsules, microcapsules, nanocapsules, nanostructured lipid carriers, sponges, cyclodextrins, vesicles, micelles, mixed micelles of surfactants, surfactant-phospholipid mixed micelles, millispheres, microspheres, nanospheres, lipospheres, microemulsions, nanoemulsions, miniparticles, milliparticles, microparticles, nanoparticles and solid lipid nanoparticles, as well as in microemulsions and nanoemulsions, which can be added to achieve a greater penetration of the active principle and/or improve its pharmacokinetic and pharmacodynamic properties. Preferred delivery or sustained release systems are liposomes, surfactant-phospholipid mixed micelles, nanocapsules containing microemulsions and microemulsions, more preferably water-in-oil microemulsions with an internal structure of reverse micelle.

The sustained release systems can be prepared by methods known in the prior art, and the compositions which contain them can be administered, for example, by topical or transdermal administration, including adhesive patches, non-adhesive patches, occlusive patches and microelectric patches, or by systemic administration, for example and not restricted to, oral or parenteral route, including nasal, rectal, subcutaneous implantation or injection, or direct implantation or injection into a specific body part, and preferably should release a relatively constant quantity of the peptides of the invention. The amount of peptide contained in the sustained release system will depend, for example, on where the composition is to be administered, the kinetics and duration of the release of the peptide of the invention, as well as the nature of the condition, disorder and/or disease to be treated and/or cared for.

The peptides of this invention can also be adsorbed on solid organic polymers or solid mineral supports such as and not restricted to, talc, bentonite, silica, starch or maltodextrin among others.

The compositions which contain the peptides of the invention, their stereoisomers, mixtures thereof and/or their cosmetically or pharmaceutically acceptable salts can be incorporated into fabrics, non-woven fabrics and medical devices which are in direct contact with the skin, thus releasing the peptides of the invention whether by biodegradation of the binding system to the fabric, non-woven fabric or medical device, or by the friction between them and the body, due to body moisture, the skin's pH or body temperature. Furthermore, the peptides of the invention can be incorporated into fabric and non-woven fabrics used for making garments that are in direct contact with the body. Preferably, the fabrics, non-woven fabrics and medical devices containing the peptides of the invention are used for the treatment and/or care of those conditions, disorders and/or diseases which improve or are prevented by PGC-1α modulation.

Examples of fabrics, non-woven fabrics, garments, medical devices and means for immobilizing the peptides to them, among which are the delivery systems and/or the sustained release systems described above, can be found in literature and are known in the prior art [Schaab C. K. "*Impregnating Fabrics With Microcapsules*", (1986), HAPPI May 1986;

Nelson G. "Application of microencapsulation in textiles". *Int. J. Pharm.*, (2002), 242, 55-62; "Biofunctional Textiles and the Skin". *Curr. Probl. Dermatol.*, (2006), v.33; Hipler U. C. and Elsner P., eds. S. Karger A G, Basel, Switzerland; Malcom R. K.; McCullagh S. D. et al., "Controlled release of a model antibacterial drug from a novel self-lubricating silicone biomaterial"., *J. Cont. Release*, (2004), 97, 313-320]. The preferred fabrics, non-woven fabrics, garments and medical devices are bandages, gauzes, t-shirts, socks, tights, underwear, girdles, gloves, diapers, sanitary napkins, dressings, bedspreads, wipes, adhesive patches, non-adhesive patches, occlusive patches, microelectric patches and/or face masks.

The cosmetic or pharmaceutical compositions which contain the peptides of this invention, their stereoisomers, mixtures thereof and/or their cosmetically or pharmaceutically acceptable salts, can be used in different types of compositions of topical, transdermal, oral or parenteral application, which optionally include cosmetically or pharmaceutically acceptable excipients necessary for formulating the desired administration form. A person skilled in the art knows the different excipients which can be used in the cosmetic or pharmaceutical compositions which contain the peptides of the invention.

The compositions of topical or transdermal application can be produced in any solid, liquid or semisolid formulation, such as and not restricted to, creams, multiple emulsions such as and not restricted to, oil and/or silicone in water emulsions, water-in-oil and/or silicone emulsions, water/oil/water or water/silicone/water type emulsions, and oil/water/oil or silicone/water/silicone type emulsions, anhydrous compositions, aqueous dispersions, oils, milks, balsams, foams, lotions, gels, cream gels, hydroalcoholic solutions, hydroglycolic solutions, hydrogels, liniments, sera, soaps, shampoos, conditioners, serums, polysaccharide films, ointments, mousses, pomades, powders, bars, pencils and sprays or aerosols, including leave-on and rinse-off formulations. These topical or transdermal application formulations can be incorporated using techniques known by the person skilled in the art into different types of solid accessories such as and not restricted to, bandages, gauzes, t-shirts, socks, tights, underwear, girdles, gloves, diapers, sanitary napkins, dressings, bedspreads, wipes, adhesive patches, non-adhesive patches, occlusive patches, microelectric patches or face masks, or they can be incorporated into different make-up products such as make-up foundation, such as fluid foundations and compact foundations, make-up removal lotions, make-up removal milks, under-eye concealers, eye shadows, lipsticks, lip protectors, lip glosses and powders among others.

The cosmetic or pharmaceutical compositions of the invention may include agents which increase the percutaneous absorption of the peptides of this invention, such as and not restricted to, dimethyl sulfoxide, dimethylacetamide, dimethylformamide, surfactants, azone (1-dodecylazacycloheptane-2-one), alcohol, urea, ethoxydiglycol, acetone, propylene glycol or polyethylene glycol, among others. Furthermore, the cosmetic or pharmaceutical compositions of this invention can be applied to local areas to be treated by means of iontophoresis, sonophoresis, electroporation, microelectric patches, mechanical pressure, osmotic pressure gradient, occlusive cure, microinjections or needle-free injections by means of pressure, such as injections by oxygen pressure, or any combination thereof, to achieve a greater penetration of the peptide of the invention. The application area will be determined by the nature of the condition, disorder and/or disease to be treated and/or cared for.

Furthermore, the cosmetic compositions containing the peptides of this invention, their stereoisomers and/or their cosmetically or pharmaceutically acceptable salts can be used in different types of formulations for oral administration, preferably in the form of oral cosmetics or drugs, such as and not restricted to, capsules, including gelatin capsules, soft capsules, hard capsules, tablets, including sugar coated tablets, powders, granules, chewing gum, solutions, suspensions, emulsions, syrups, elixirs, polysaccharide films, jellies or gelatins, and any other form known by the person skilled in the art. In particular, the peptides of the invention can be incorporated into any form of functional food or fortified food, such as and not restricted to, dietary bars or compact or non-compact powders. These powders can be dissolved in water, juices, soda, dairy products, soy derivatives or can be incorporated into dietary bars. The peptides of this invention can be formulated with common excipients and adjuvants for oral compositions or food supplements, such as and not restricted to, fat components, aqueous components, humectants, preservatives, texturizing agents, flavors, aromas, antioxidants and colorants common in the food industry.

Cosmetic or pharmaceutical compositions containing the peptides of the invention, their stereoisomers, mixtures thereof and/or their cosmetically or pharmaceutically acceptable salts can also be administered, as well as by topical or transdermal route, by any other appropriate route, such as oral or parenteral route, for which they will include the pharmaceutically acceptable excipients necessary for the formulation of the desired administration form. In the context of this invention, the term "parenteral" includes nasal, auricular, ophthalmic, vaginal, urethral, rectal route, subcutaneous, intradermal, intravascular injections, such as intravenous, intramuscular, intraocular, intravitreous, intracorneal, intraspinal, intramedullary, intracranial, intracervical, intracerebral, intrameningeal, intraarticular, intrahepatic, intrathoracic, intratracheal, intrathecal and intraperitoneal, and any another similar injection or infusion technique. A person skilled in the art knows the different means by which the cosmetic or pharmaceutical compositions which contain the peptides of the invention can be administered.

Among the cosmetically or pharmaceutically acceptable adjuvants contained in the cosmetic or pharmaceutical compositions described in this invention are additional ingredients commonly used in compositions for the treatment and/or care of the skin such as and not restricted to, other PGC-1α modulating agents, other PPARγ modulating agents, other agents which increase or reduce the triglyceride content of adipocytes, agents stimulating or delaying adipocyte differentiation, lipolytic agents or agents stimulating lipolysis, anti-cellulite agents, adipogenic agents, agents which stimulate adipocyte proliferation, inhibitors of acetylcholine-receptor aggregation, agents inhibiting muscle contraction, anticholinergic agents, elastase inhibiting agents, matrix metalloproteinase inhibiting agents, melanin synthesis stimulating or inhibiting agents, whitening or depigmenting agents, propigmenting agents, self-tanning agents, anti-aging agents, NO-synthase inhibiting agents, 5α-reductase inhibiting agents, lysyl- and/or prolyl hydroxylase inhibiting agents, antioxidants, free radical scavengers and/or agents against atmospheric pollution, reactive carbonyl species scavengers, anti-glycation agents, antihistamine agents, antiviral agents, antiparasitic agents, emulsifiers, emollients, organic solvents, liquid propellants, skin conditioners such as humectants, substances that retain moisture, alpha hydroxyacids, beta hydroxyacids, moisturizers, epidermal hydrolytic enzymes, vitamins, amino acids, proteins, pigments or colorants, dyes, biopolymers, gelling polymers, thickeners, surfactants, softening agents, emulsifiers, binding agents, preservatives, anti-wrinkle agents, agents able to reduce or treat bags under the eyes, exfoliating agents, desquamating agents, keratolytic agents, antimicrobial agents, antifungal agents, fungistatic agents, bactericidal agents, bacteriostatic agents, agents stimulating the synthesis of dermal or epidermal macromolecules and/or capable of inhibiting or preventing their degradation, collagen synthesis-stimulating agents, elastin synthesis-stimulation agents, decorin synthesis-stimulation agents, laminin synthesis-stimulation agents, defensin synthesis-stimulating agents, chaperone synthesis-stimulating agents, cAMP synthesis-stimulating agents, heat shock proteins, HSP70 synthesis stimulators, heat shock protein synthesis-stimulating agents, aquaporin synthesis-stimulating agents, hyaluronic acid synthesis-stimulating agents, fibronectin synthesis-stimulating agents, sirtuin synthesis-stimulating agents, agents stimulating the synthesis of lipids and components of the stratum corneum, ceramides, fatty acids, agents that inhibit collagen degradation, agents that inhibit elastin degradation, agents that inhibit serine proteases such as cathepsin G, agents stimulating fibroblast proliferation, agents stimulating keratinocyte proliferation, agents stimulating melanocyte proliferation, agents stimulating keratinocyte differentiation, agents that inhibit acetylcholinesterase, skin relaxant agents, glycosaminoglycan synthesis-stimulating agents, antihyperkeratosis agents, comedolytic agents, anti-psoriasis agents, DNA repair agents, DNA protecting agents, stabilizers, anti-itching agents, agents for the treatment and/or care of sensitive skin, firming agents, redensifying agents, restructuring agents, anti-stretch mark agents, binding agents, agents regulating sebum production, antiperspirant agents, agents stimulating healing, coadjuvant healing agents, agents stimulating reepithelialization, coadjuvant reepithelialization agents, cytokine growth factors, calming agents, anti-inflammatory agents, anesthetic agents, agents acting on capillary circulation and/or microcirculation, agents stimulating angiogenesis, agents that inhibit vascular permeability, venotonic agents, agents acting on cell metabolism, agents to improve dermal-epidermal junction, agents inducing hair growth, hair growth inhibiting or retardant agents, perfumes, chelating agents, plant extracts, essential oils, marine extracts, agents obtained from a biofermentation process, mineral salts, cell extracts, sunscreens and organic or mineral photoprotective agents active against ultraviolet A and/or B rays or mixtures thereof, provided that they are physically and chemically compatible with the rest of components in the composition and particularly with the peptides of general formula (I) contained in the composition of this invention. Likewise, the nature of these additional ingredients should not unacceptably alter the benefits of the peptides of this invention. The nature of these additional ingredients can be synthetic or natural, such as plant extracts, or come from a biotechnological process, or from a combination of a synthetic process and a biotechnological process. Additional examples can be found in "*CTFA International Cosmetic Ingredient Dictionary & Handbook*", 12th Edition, (2008). In the context of this invention, biotechnological process is understood to be any process to produce the active ingredient, or part of it, in an organism, or in part of it.

An additional aspect of this invention relates to a pharmaceutical composition which comprises a pharmaceutically effective quantity of at least one peptide according to the general formula (I), its stereoisomers, mixtures thereof and/or its pharmaceutically acceptable salts, as well as a pharmaceutically effective quantity of at least one anti-diabetic agent. Examples of anti-diabetic agents are for example and not restricted to, metformin, buformin, phenformin, acetohexamide, chlorpropamide, carbutamide, tolbutamide, tolazamide, glipizide, gliclazide, glibenclamide, glyburide, gliquidone, glyclopyramide, glimepiride, pramlintide acetate, liraglutide, exenatide, lixisenatide, taspoglutide, acarbose, miglitol, rosiglitazone, rivoglitazone, pioglitazone, repaglinide, nateglinide, mitiglinide, canagliflozin, dapagliflozin, sergliflozin, aleglitazar, muraglitazar or tesaglitazar among others.

An additional aspect of this invention relates to a cosmetic or pharmaceutical composition containing a cosmetically or pharmaceutically effective amount of at least one peptide of the invention according to the general formula (I), its stereoisomers, mixtures thereof and/or its cosmetically or pharmaceutically acceptable salts, and also a cosmetically or pharmaceutically effective amount of at least one extract, a synthetic compound or product of biotechnological origin which is an agent that increases or reduces the triglyceride content of adipocytes, an agent that stimulates or delays adipocyte differentiation, anti-cellulite agent, lipolytic agent, venotonic agent, adipogenic agent and/or agent which stimulates adipocyte proliferation for example and not restricted to extracts or hydrolyzed extracts of *Agave americana, Agave sisalana, Alchemilla vulgaris, Anemarrhena apshodeloides, Angelica sinensis, Armeniacea* sp., *Arnica montana* L, *Asparagus adscende, Asparagus cochichinensis, Asparagus filicinus, Asparagus meioclados, Asparagus munitus, Asparagus myriancanthus, Asparagus officinalis, Asparagus racemosus, Asparagus taliensis, Asparagus trichoclados, Atractylodis platicodon*, bamboo, *Betula alba, Bupleurum chinensis, Calendula officinalis*, cangzhu, *Cecropia obtusifolia, Celosia cristata, Centella asiatica, Chenopodium quinoa, Chrysanthellum indicum, Cimifuga racemosa, Citrus aurantium amara, Cnicus benedictus, Coffea arabica, Cola nipida, Coleus barbatus, Coleus blumei, Coleus esquirolii, Coleus forskohlii, Coleus scutellaroides, Coleus* sp., *Coleus xanthantus, Commiphora myrrha, Crithmum maritimum, Cuminum cyminum, Dioscorea colettii, Dioscorea villosa, Eugenia caryophyllus, Filipendula ulmaria* L, *Foeniculum vulgare, foenum-graecum, Fucus vesiculosus, Ginkgo biloba, ginkgo biloba, Glycine max, Glycyrrhiza glabra, Hedera helix* (ivy extract), *Hibiscus sabdariffa, Hordeum vulgare, Humulus lupulus, Hyperycum perforatum, Ilex paraguariensis, Kigelia africana, Laminaria digitata, Lilium brownfi, Lupinus perennis, Lycopersicon pimpinellifolium, Medusomyces gisevi, Nelumbium speciosum, Nicotianum tabacum, Orthosiphon stamincus benth, Panax ginseng, Paullinia cupana, Peumus boldus, Phyllacantha fibrosa, Piper methysticum, Piper nigrum, Prunella vulgaris, Prunus amygdalus dulcis, Quillaja saponaria, Radix asparagi, Radix sarsaparrilla, Rosmarinus officinalis, Rubus idaeus, Ruscus aculeatus* (extract of Butcher's broom), *Salvia officinalis* L, *Sambucus nigra, Serenoa repens, Smilax aristolochiaefolia, Smilax aspera* (rough bindweed), *Smilax ornata, Solanum paniculatum, Spirulina platensis* algae, *Taraxacum erythrospermum, Taraxacum officinale*, green tea, Tian-dong, *Tribulus terrestri, Trifolium pratense, Trifolium repens, Trigonella foenum graecum, Turnera diffusa, Ulmus rubra, Uncaria tomentosa, Verbena officinalis, Vitex agnus-castus, Yuca* spp, *Yucca brevifolia, Yucca filamentosa, Yucca filifera, Yucca schudufera, Yucca vaccata* or zhi-mu among others, alverin, alverin citrate, dihydromyricetin, coenzyme A, lipase, cerulenin, sirtuin, rutin, glaucine, esculin, visnadine, caffeine, theophylline, theobromine, aminophylline, xanthine, carnitine, forskolin, escin, ruscogenin, hederin, triethanolamine iodide, sarsasapogenin, parigenin, smilagenin, isosarsasapogenin, epi-tigogenin, tigogenin, epi-sarsasapogenin, neotigogenin, epi-smilagenin, parillin, timosaponin, xilingsaponin, filiferin, AMPc synthesis inducing or inhibiting agents, Lanachrys® [INCI: *Chrysanthellum Indicum* Extract] marketed by Atrium/Unipex, Slim-Excess™ [INCI: Water, Butylene Glycol, Sodium Chloride, Hydrolyzed Carrageenan, Xanthan Gum], Sveltine™ [INCI: Water, Butylene Glycol, Carnitine, Lecithin, Caffeine, Carbomer, Salicylic Acid, Atelocollagen, *Centella Asiatica* Extract, Esculin, Sodium Chondroitin Sulfate], Peru Liana [INCI: *Uncaria Tomentosa* Extract] or Flavenger™ [INCI: Caprylic/Capric Triglyceride, Silica Dimethyl Silylate, Glyceryl Oleate, Quercetin Caprylate] marketed by BASF, Scopariane [INCI: *Sphacelaria Scoparia*], Phyco R75 [INCI: *Laminaria Digitata*], Pheoslim [INCI: *Phyllacantha Fibrosa* Extract], Buckwheat Wax [INCI: *Polygonum fagopyrum*] or Areaumat Samphira [INCI: *Crithmum Maritimum* Extract] marketed by Codif, Slimming Factor Karkade™ [INCI: *Hibiscus Sabdariffa*] marketed by Cosmetochem, Liposuctionine [proposed INCI: Acetyl Hexapeptide] marketed by Infinitec Activos, Xantalgosil C® [INCI: Acefylline Methylsilanol Mannuronate], Theophyllisilane C® [INCI: Methylsilanol Carboxymethyl Theophylline Alginate] or Glutrapeptide® [INCI: Pyroglutamylamidoethyl Indole] marketed by Exsymol, Timiline® [INCI: Polyglucuronic acid] or Kigeline® [INCI: *Kigelia Africana* Extract] marketed by Greentech, Visnadine [INCI: Visnadine] or *Ginkgo Biloba* Dimeric Flavonoids Phytosome [INCI: Phospholipids, *Ginkgo Biloba* Leaf Extract] marketed by Indena, Slimfit® LS 9509 [INCI: *Cecropia Obtusifolia* Bark Extract] marketed by Laboratoires Serobiologiques/Cognis, Liporeductyl® [INCI: Water, Glycerin, Lecithin, Caffeine, Butcherbroom (*Ruscus Aculeatus*) Root Extract, Maltodextrin, Silica, Tea-Hydroiodide, Propylene Glycol, Ivy (*Hedera Helix*) Extract, Carnitine, Escin, Tripeptide-1, Xanthan Gum, Carrageenan (*Chondrus Crispus*), Disodium EDTA] (Water, Glycerin, Lecithin, Caffeine, Extract of Butcher's Broom root (*Ruscus Aculeatus*), Maltodextrin, Silica, Triethanolamine Hydroiodide, Propylen Glycol, Ivy Extract (*Hedera Helix*), Carnitine, Escin, Tripeptide-1, Xanthan Gum, Carrageenan (*Chondrus Crispus*), EDTA (Disodium) marketed by Lipotec, Iso-Slim Complex [INCI: Soy Isoflavones, Caffeine, Carnitine, *Spirulina Platensis* Extract, Polysorbate 80, Alcohol, Phenoxyethanol, Aqua], Happybelle-PE [INCI: Lecithin, *Vitex Agnus Castus* Extract, Glycerin, Ascorbyl Tetraisopalmitate, Tocopherol, Caprylic/Capric Triglyceride, Cyclodextrin, Alcohol, Water] or AmaraShape [INCI: Lecithin, Caffeine, *Citrus Aurantium Amara* Extract, Pentylene Glycol, Alcohol, Water] marketed by Mibelle Biochemistry, Regu®-Slim [INCI: Maltodextrin, Caffeine, *Paullinia Cupana* Seed Extract, Carnitine, Microcrystalline Cellulose, Cysteic Acid, Pantheine Sulfonate] or Regu®-Shape [INCI: Isomerized Linoleic Acid, Lecithin, Glycerin, Polysorbate 80] marketed by Pentapharm/DSM, Voluplus™ [INCI: *Macadamia Ternifolia* Seed Oil, Macelignan, Tocopherol], Provislim™ [INCI: Propanediol, Water (Aqua), Fisetin, Raspberry Ketone], Noline [INCI: Macelignan (*Myristica fragans*)], Myriceline [INCI: Dihydromyricetin] or Drenalip [INCI: *Ruscus Aculeatus* Root Extract, *Citrus Medica Limonum* Peel Extract, *Solidago Virgaurea* Extract, *Astragalus Membranaceus* Root Extract] marketed by Provital, Actisculpt [INCI: *Commiphora Myrrha* Extract, *Coleus Forskohlii* Root Extract] marketed by Quest, Perfeline® [INCI: Water, Carnitine, Caffeine, *Ruscus Aculeatus* Extract], CellActive® Shape [INCI: *Chlorella Vulgaris/Lupinus Albus* Protein Ferment, *Coleus Forskohlii*, Caffeine] or CellActive® Form [INCI: *Garcinia Mangostana* Peel Extract, *Chlorella Vulgaris/Lupinus Albus* Protein Ferment, *Pyrus Cydonia* Seed Extract] marketed by Rahn, ProContour™ [INCI: Water, Alcohol, Lecithin, Caffeine, Carnitine, *Centella Asiatica* Leaf Extract, Potassium Phosphate, *Coleus Forskohlii* Root Extract] marketed by Rovi Cosmetics, Volufiline™ [INCI: *Anemarrhena asphodeloides* (root) extract], Unislim™ [INCI: *Ilex Paraguariensis* (Leaf) Extract, Water, Butylene Glycol, *Coffea Arabica* (Coffee) Seed Extract (Bean), PEG-60 Almond Glycerides, Glycerin, Cetyl Hydroxyethylcellulose], Redulite™ [INCI: Glycerin, Aqua, Ethoxydiglycol, *Sambucus Nigra*, Sodium Polyacrylate], Pleurimincyl™ [INCI: Caffeine, *Bupleurum Chinensis* extract], Phytotal™ SL [INCI: Glycerin, *Verbena Officinalis* Extract, Butylene Glycol, *Sambucus Nigra* Flower Extract, *Eugenia Caryophyllus* (Clove) Flower Extract, Lecithin], Phytosonic™ [INCI: Aqua, *Euglena Gracilis* Extract, Caffeine, *Glaucium Flavum* Leaf Extract], Ovaliss™ [INCI: Glycerin, Aqua, Coco-glucoside, Caprylyl Glycol, Alcohol, Glaucine], Lipocare™ [INCI: Caffeine, Coenzym A, *Bupleurum Chinensis* extract], Cyclolipase™ [INCI: Glyceryl Polymethacrylate, Water, Caffeine, Lipase, Adenosine Phosphate], Coaxel™ [INCI: Caffeine, Coenzyme A, Carnitine, Water, Glycerin] or Bodyfit™ [INCI: Glycerin, Aqua (Water), Coco-Glucoside, Caprylyl Glycol, Alcohol, Glaucine] marketed by Sederma/Croda, Voluform [INCI: Palmitoyl isoleucine], Adiposlim [INCI: Sorbitan Laurate, Lauroyl Proline] or Adipoless [INCI: Butylene Glycol, *Chenopodium Quinoa* Seed Extract] marketed by Seppic, Slimactive® [INCI: *Peumus Boldus* Leaf Extract], Remoduline® [INCI: *Citrus Aurantium Amara* Flower Extract], Pro-Sveltyl [INCI: *Nelumbium Speciosum* Extract], Biosculptine® [INCI: Hydrolyzed *Celosia Cristata* Flower/Seed Extract, Hydrolyzed *Prunella Vulgaris* Extract] or Affiness® [INCI: Hydrolyzed *Coriandrum Sativum* Fruit Extract, *Citrus Aurantium Dulcis* (Orange) Fruit Extract] marketed by Silab, Delipidol [INCI: Tyrosyl Punicate], Guaraslim® [INCI: Butylene Glycol, Water, Caffeine, *Paullinia Cupana* Seed Extract, *Ptychopetalum Olacoides* Bark Extract] or Caobromine® [INCI: *Theobroma Cocoa* Shell Extract] marketed by Solabia, Abdoliance [INCI: Sucrose palmitate, Polysorbate 20, Glyceryl Linolenate, *Paullinia Cupana* Seed Extract, Maltodextrin, *Prunus Amygdalus Dulcis* (Sweet Almond) Oil, Lecithin, Water, *Citrus Aurantium Amara* (Bitter Orange) Peel Extract, Phenoxyethanol, Tocopherol], Betaphroline [INCI: *Tephrosia Purpurea* Seed Extract] or Commipheroline [INCI: *Commiphora Mukul* Resin Extract] marketed by Soliance, UCPeptide™ V [INCI: Water, Butylene Glycol, Pentapeptide] or ATPeptide™ IS [INCI: Tripeptide-3] marketed by Vincience/ISP among others, or mixtures thereof.

An additional aspect of this invention relates to a cosmetic or pharmaceutical composition which comprises a cosmetically or pharmaceutically effective amount of at least one peptide according to the general formula (I), its stereoisomers, mixtures thereof and/or its cosmetically or pharmaceutically acceptable salts, and also a cosmetically or pharmaceutically effective amount of at least one extract, a synthetic compound or product of biotechnological origin which is a firming, redensifying and/or restructuring agent for example and not restricted to extracts or hydrolyzed extracts of *Malpighia punicitolia, Cynara scolymus, Gossypium herbaceum, Aloe Barbadensis, Panicum miliaceum, Morus nigra, Sesamum indicum, Glycine soja* or *Triticum vulgare* among others, ActiMatrix [INCI: *Lentinus Edodes* (Shiitake Mushroom) Extract] marketed by Active Organics, Peptamide 6 [INCI: Hexapeptide-11] marketed by Arch, Lanablue [INCI: Algae extract], Hydriame [INCI: Water, Glycosaminoglycans, Sclerotium Gum] or ChroNOline [INCI: Caprooyl Tetrapeptide-3] marketed by Atrium Innovations/ISP, Deliner [INCI: *Zea Mays* (Corn) Kernel Extract] marketed by BASF, Ursolisome [INCI: Lecithin, Ursolic Acid, Atelocollagen, Xanthan Gum, Sodium chondroitin sulfate] or Collalift [INCI: Hydrolyzed Malt Extract] marketed by Coletica/Engelhard/BASF, Syn-Hycan [INCI: Tetradecyl Aminobutyroylvalylaminobutyric Urea Trifluoroacetate, Glycerin, Magnesium Chloride], Syn-Glycan [INCI: Glycerin, Tetradecyl Aminobutyroylvalyl-aminobutyric Urea Trifluoroacetate, Magnesium Chloride] or BeauActive MTP [INCI: Hydrolyzed Milk Protein] marketed by DSM, Phytokine [INCI: Hydrolyzed Soy Protein] or Basaline [INCI: Hydrolyzed Malt Extract] marketed by Engelhard, Phytosphingosine SLC [INCI: Salicyloyl Phytosphingosine] marketed by Evonik Goldschmidt, Collageneer [INCI: *Helianthus Annuus* Seed Oil, *Lupinus Albus* Extract] marketed by Expanscience Laboratoires, Hematite [INCI: Hematite] or Gatuline Skin-Repair Bio [INCI: *Onopordum Acanthium* Flower/Leaf/Stem Extract] marketed by Gattefossé, Glycosann [INCI: Sodium Chondroitin Sulfate] marketed by Impag, Laminixyl IS [INCI: Heptapeptide-8] or Aquarize IS [INCI: Hydrolyzed Rice Extract] marketed by ISP, Vit-A-Like [INCI: *Vigna Acontifolia* Seed Extract], Triactigen [INCI: Mannitol, Cyclodextrin, Yeast Extract, Disodium Succinate], Syniorage [INCI: Acetyl Tetrapeptide-11], Sphingoceryl Veg [INCI: Phyto-ceramides], Prodejine [INCI: Mannitol, Cyclodextrin, Yeast Extract, Disodium Succinate], Hibiscin HP [INCI: *Hibiscus Esculentus* Seed Extract], Eterniskin [INCI: *Grifola Frondosa* Fruiting Body Extract], Dermican [INCI: Acetyl Tetrapeptide-9], Arganyl [INCI: *Argania Spinosa* Leaf Extract] or Aqu'activ [INCI: Behenyl Alcohol, Glyceryl Oleate, Cocamide MIPA, Calcium Citrate] marketed by Laboratoires Serobiologiques/Cognis, Antarcticine® [INCI: *Pseudoalteromonas* Ferment Extract], Decorinyl® [INCI: Tripeptide 10 Citrulline], Relistase™ [INCI: Acetylarginyltriptophyl Diphenylglycine], Serilesine® [INCI: Hexapeptide-10] or Trylagen® [INCI: *Pseudoalteromonas* Ferment Extract, Hydrolyzed Wheat Protein, Hydrolyzed Soy Protein, Tripeptide 10 Citrulline, Tripeptide 1] marketed by Lipotec, Ronacare Cyclopeptide-5 [proposed INCI: Cyclopeptide-5] marketed by Merck, Lipobelle Soyaglicane [INCI: Soy Isoflavones] marketed by Mibelle, Syn-Tacks [INCI: Glycerin, Palmitoyl Dipeptide-5 Diaminobutyloyl Hydroxythreonine, Palmitoyl Dipeptide-6 Diaminohydroxybutyrate], Syn-Coll [INCI: Palmitoyl Tripeptide-5], Pepha-Tight [INCI: Algae Extract, Pullulan], Pepha-Nutrix [INCI: Natural Nutrition Factors] or Pentacare-NA [INCI: Hydrolyzed Wheat Gluten, *Ceratonia Siliqua* Gum, Water] marketed by Pentapharm, Zirhafirm [INCI: *Zizyphus Jujuba* Seed Extract, Phytoecdysteroids], Vitasource [INCI: Propanediol, Water, Baicalin], Pronalen Firming [INCI: Lady's Thistle Extract, Lady's Mantle Extract, Horsetail Extracti, Soy Germ Extract, Wheat Germ Extract, Alfalfa Extract, Radish Extract, Water (Aqua), Butylene Glycol, Decyl Glucoside], Homeostatine [INCI: *Enteromorpha Compressa, Caesalpinia Spinosa*] or Gladback [INCI: *Poria Cocos* Polysaccharide] marketed by Provital, Reforcyl [INCI: Glycerin, Water, Glutamine, Decyl Glucoside, Phenethyl Alcohol, *Cistus Incanus* Flower/Leaf/Stem Extract, *Gynostemma Pentaphyllum* Leaf/Stem Extract] marketed by Rahn, Subliskin [INCI: *Sinorhizobium Meliloti* Ferment, Cetyl Hydroxyethyl Cellulose, Lecithin], Rigin [INCI: Palmitoyl Tetrapeptide-3], Renovage [INCI: Caprylic/Capric Triglyceride, Teprenone], Kombuchka [INCI: *Saccharomyces*/Xylinum Black Tea Ferment, Glycerin, Hydroxyethyl cellulose], Essenskin [INCI: 3-aminopropane Sulfonic Acid, Pentylene Glycol], Dynalift [INCI: Water (Aqua), Sodium Polystyrene Sulfonate, *Sorghum Bicolor* Stalk Juice, Glycerin], Biopeptide EL [INCI: Palmitoyl Oligopeptide], Biopeptide CL [INCI: Palmitoyl Oligopeptide] or Biobustyl [INCI: Glyceryl Polymethacrylate, Rahnella/Soy Protein Ferment, Water, Propylene Glycol, Glycerin, PEG-8, Palmitoyl Oligopeptide] marketed by Sederma/Croda, Sepilift DPHP [INCI: Dipalmitoyl hydroxyproline], Lipacide PVB [INCI: Palmitoyl hydrolyzed Wheat Protein] or Deepaline PVB [INCI: Palmitoyl hydrolyzed Wheat Protein] marketed by Seppic, Toniskin [INCI: Yeast Extract], Ridulisse C [INCI: Soybean], Retilactyl [INCI: hydrolyzed pepper fruit extract], Raffermine [INCI: Hydrolyzed Soy Flour] or Coheliss [INCI: Arabinoxylans purified from Rye Seeds] marketed by Silab, Peptiskin [INCI: Arginine/Lysine polypeptide] or Nuteline C [INCI: Hydrolyzed Hazelnut Protein], marketed by Solabia, RenovHyal [INCI: Sodium Hyaluronate] or Dakaline [INCI: *Prunus Amygdalus Dulcis, Anogeissus Leiocarpus* Bark Extract] marketed by Soliance, SymPeptide 230 [INCI: Glycerin, Water (Aqua), Myristoyl Hexapeptide-4] or SymPeptide 225 [INCI: Glycerin, Water (Aqua), Myristoyl Pentapeptide-11] marketed by Symrise, Exo-T [INCI: Vibrio Exopolysaccharide Extract] marketed by Unipex or Peptide Vinci 01 [INCI: Penta-decapeptide-1] or Collaxyl [INCI: Hexapeptide-9] marketed by Vincience/ISP among others, or mixtures thereof.

An additional aspect of this invention relates to a cosmetic or pharmaceutical composition which comprises a cosmetically or pharmaceutically effective amount of at least one peptide according to the general formula (I), its stereoisomers, mixtures thereof and/or its cosmetically or pharmaceutically acceptable salts, and also a cosmetically or pharmaceutically effective amount of at least one extract, a synthetic compound or product of biotechnological origin which is an anti-stretch mark agent for example and not restricted to extracts or hydrolyzed extracts of *Centella Asiatica, Rosa canina, Rosa moschata, Rosa rubiginosa, Echinacea angustifolia, Symphytum officinal, Equisetum arvense, Hypericum perforatum, Mimosa tenuiflora, Aloe vera*, Dermochlorella [INCI: *Chlorella Vulgaris* Extract] marketed by Codif, Hydroxyprolisilane C N [INCI: Methylsilanol Hydroxyproline Aspartate] or Algisium C [INCI: Methylsilanol Mannuronate] marketed by Exsymol, Gatuline In-Tense [INCI: *Spilanthes Acmella* Flower Extract] marketed by Gattefossé, Anti-stretchmarks Phytogreen [INCI: *Alchemilla Vulgaris* Extract] marketed by Greentech, Cikaderm [INCI: *Croton Lechleri*, Aluminium Sucrose Octasulfate, Glycerin, Aqua] marketed by Kalichem Italia S. R. L., Lipofructyl Argan [INCI: *Argania Spinosa* Kernel Oil] marketed by Laboratoires Serobiologiques/Cognis, Vanistryl® [INCI: Water, Caprylyl/Capryl Glucoside, Lecithin, Glycerin, *Pseudoalteromonas* Ferment Extract, Acetyl Tripeptide-30 Citrulline, Pentapeptide-18, Xanthan Gum, Caprylyl Glycol] marketed by Lipotec, Regu-Stretch [INCI: Water, Glycerin, Palmitoyl tripeptide-5, Panthenol, *Marrubium vulgare* extract] marketed by Pentapharm/DSM, Darutoside [INCI: Butylene Glycol, Darutoside, *Centella Asiatica* Extract] marketed by Sederma/Croda, Regestril [INCI: Butylene Glycol, Water, Cetyl Hydroxyethylcellulose, Rutin, Palmitoyl Oligopeptide, Palmitoyl Tetrapeptide-3, *Phaseolus Lunatus* (Green Bean) Extract] marketed by Sederma, Elastonyl [INCI: Hydrolyzed *Cucurbita Pepo* (Pumpkin) Seedcake] marketed by Silab or Peptide Vinci 02 [INCI: Hexapeptide-3] marketed by Vincience among others, or mixtures thereof.

An additional aspect of this invention relates to a cosmetic or pharmaceutical composition which comprises a cosmetically or pharmaceutically effective amount of at least one peptide according to the general formula (I), its stereoisomers, mixtures thereof and/or its cosmetically or pharmaceutically acceptable salts, and also a cosmetically or pharmaceutically effective amount of at least one extract, a synthetic compound or product of biotechnological origin which is an anti-wrinkle agent and/or anti-aging agent for example and not restricted to the extracts or hydrolyzed extracts of *Vitis vinifera, Rosa canina, Curcuma longa, Theobroma cacao, Ginkgo biloba, Leontopodium alpinum* or *Dunaliella salina* among others, Matrixyl® [INCI: Palmitoyl Pentapeptide-4], Matrixyl 3000® [INCI: Palmitoyl Tetrapeptide-7, Palmitoyl Oligopeptide], Essenskin™ [INCI: calcium hydroxymethionine], Renovage [INCI: teprenone] or Dermaxyl® [INCI: Palmitoyl Oligopeptide] marketed by Sederma/Croda, Vialox® [INCI: Pentapeptide 3], Syn® Ake® [INCI: Dipeptide Diaminobutyroyl Benzylamide Diacetate], Syn®-Coll [INCI: Palmitoyl Tripeptide-5], Phytaluronate [INCI: Locust Bean (*Ceratonia siliqua*) Gum] or Preregen® [INCI: *Glycine soja* (Soybean) Protein, Oxido Reductases] marketed by Pentapharm/DSM, Myoxinol™ [INCI: Hydrolyzed *Hibiscus esculentus* Extract], Syniorage™ [INCI: Acetyl Tetrapeptide-11], Dermican™ [INCI: Acetyl Tetrapeptide-9] or DN AGE™ LS [INCI: *Cassia alata* leaf Extract] marketed by Laboratoires Sérobiologiques/Cognis, Algisum C® [INCI: Methylsilanol Mannuronate] or Hydroxyprolisilane CN® [INCI: Methylsilanol Hydroxyproline Aspartate] marketed by Exsymol, Argireline® [INCI: Acetyl Hexapeptide-8], SNAP-7 [INCI: Acetyl Heptapeptide-4], SNAP-8 [INCI: Acetyl Octapeptide-3], Leuphasyl® [INCI: Pentapeptide-18], Inyline™ [INCI: Acetyl Hexapeptide-30], Aldenine® [INCI: Hydrolized wheat protein, hydrolized soy protein, Tripeptide 1], Preventhelia™ [INCI: Diaminopropionoyl Tripeptide-33], Decorinyl® [INCI: Tripeptide-10 Citrulline], Trylagen® [INCI: *Pseudoalteromonas* Ferment Extract, Hydrolyzed Wheat Protein, Hydrolyzed Soy Protein, Tripeptide 10 Citrulline, Tripeptide 1], Eyeseryl® [INCI: Acetyl Tetrapeptide-5], Peptide AC29 [INCI: Acetyl Tripeptide-30 Citrulline], Relistase™ [INCI: Acetylarginyltriptophyl Diphenylglycine], Thermostressine® [INCI: Acetyl Tetrapeptide-22], Lipochroman 6 [INCI: Dimethylmethoxy Chromanol], Chromabright™ [INCI: Dimethylmethoxy Chromanyl Palmitate], Antarcticine® [INCI: *Pseudoalteromonas* Ferment Extract], dGlyage™ [INCI: Lysine HCl, Lecithin, Tripeptide-9 Citrulline], Vilastene™ [INCI: Lysine HCl, Lecithin, Tripeptide-10 Citrulline] or Hyadisine™ [INCI: *Pseudoalteromonas* Ferment Extract] marketed by Lipotec, Kollaren® [INCI: Tripeptide 1, Dextran] marketed by Institut Europeen de Biologie Cellulaire, Collaxyl® IS [INCI: Hexapeptide-9], Laminixyl IS™ [INCI: Heptapeptide], Orsirtine™ GL [INCI: *Oryza sativa* (Rice) Extract], D'Orientine™ IS [INCI: *Phoenix dactylifera* (Date) Seed Extract], Phytoquintescine™ [INCI: Einkorn (*Triticum monococcum*) Extract] or Quintescine™ IS [INCI: Dipeptide-4] marketed by Vincience/ISP, BONT-L-Peptide [INCI: Palmitoyl Hexapeptide-19] marketed by Infinitec Activos, Deepaline™ PVB [INCI: Palmitoyl hydrolyzed Wheat Protein] or Sepilift® DPHP [INCI: Dipalmitoyl Hydroxyproline] marketed by Seppic, Gatuline® Expression [INCI: *Acmella oleracea* Extract], Gatuline® In-Tense [INCI: *Spilanthes acmella* Flower Extract] or Gatuline® Age Defense 2 [INCI: *Juglans regia* (Walnut) Seed Extract] marketed by Gattefossé, Thalassine™ [INCI: Algae Extract] marketed by Biotechmarine, ChroNOline™ [INCI: Caprooyl Tetrapeptide-3] or Thymulen-4 [INCI: Acetyl Tetrapeptide-2] marketed by Atrium Innovations/Unipex Group, EquiStat [INCI: *Pyrus malus* Fruit Extract, *Glycine soja* Seed Extract] or Juvenesce [INCI: Ethoxydiglicol and Caprylic Triglycerid, Retinol, Ursolic Acid, Phytonadione, Ilomastat] marketed by Coletica/Engelhard/BASF, Ameliox [INCI: Carnosine, Tocopherol, *Silybum marianum* Fruit Extract or PhytoCellTec *Malus Domestica* [INCI: *Malus domestica* Fruit Cell Culture] marketed by Mibelle Biochemistry, Bioxilift [INCI: *Pimpinella anisum* Extract] or SMS Anti-Wrinkle®[INCI: *Annona squamosa* Seed Extract] marketed by Silab, antagonists of the $Ca^{2+}$ channel such as and not restricted to, alverine, manganese or magnesium salts, certain secondary or tertiary amines, retinol and its derivatives, idebenone and its derivatives, Coenzyme Q10 and its derivatives, boswellic acid and its derivatives, GHK and its derivatives and/or salts, carnosine and its derivatives, DNA repair enzymes such as and not restricted to, photolyase or T4 endonuclease V, or chloride channel agonists among others, and/or mixtures thereof.

Another aspect of this invention relates to a cosmetic or pharmaceutical composition which comprises a cosmetically or pharmaceutically effective amount of at least one peptide according to the general formula (I), its stereoisomers, mixtures thereof and/or its cosmetically or pharmaceutically acceptable salts, and also a cosmetically or pharmaceutically effective amount of at least one protein, preferably from the PGC family, more preferably, PGC-1α.

Applications

An aspect of this invention relates to the use of at least one peptide of general formula (I), its stereoisomers, mixtures thereof and/or its cosmetically or pharmaceutically acceptable salts in the preparation of a cosmetic or pharmaceutical composition for the modulation of PGC-1α.

Another aspect of this invention relates to the use of at least one peptide of general formula (I), its stereoisomers, mixtures thereof and/or its cosmetically or pharmaceutically acceptable salts in the preparation of a cosmetic or pharmaceutical composition for the modulation of PPARγ.

In another particular embodiment, this invention relates to the use of at least one peptide of general formula (I), its stereoisomers, mixtures thereof and/or its cosmetically or pharmaceutically acceptable salts, in the treatment and/or care of conditions, disorders and/or diseases selected from the group formed by metabolic diseases and/or disorders such as diseases related to lipid metabolism, changes to gluconeogenesis, obesity, type 2 diabetes, cellulitis, gynecomastia, pseudogynecomastia, lipoatrophy, semicircular lipoatrophy, lipodystrophy, aging, photoaging, cutaneous traumas, reepithelialization of injuries, dehydration of the skin, xerosis, keratinization disorders, callouses, hard skin, psoriasis, lichen planus, skin lesions associated with lupus, dermatitis, atopic dermatitis, seborrheic dermatitis, senile dermatitis, dandruff, cradle cap, seborrhea, hyperseborrhea of acne, solar dermatitis, seborrheic keratosis, senile keratosis, actinic keratosis, photoinduced keratosis, follicular keratosis, acne vulgar, nevus, keloids, change in the function of fibroblasts, nodular fascitis, scleroderma, Dupuytren's contracture, fibrous scar formation, disorders of the sebaceous glands, acne rosacea, polymorphic acne, comedones, polymorphous, rosacea, nodulocystic acne, conglobate acne, senile acne, ichthyosis, Darier's disease, keratodermia palmoplantaris, leukoplakia, mucosal lichen, cutaneous lichen, cutaneous psoriasis, mucosal psoriasis, nail psoriasis, psoriatic rheumatism, eczema, common warts, flat warts, epidermodysplasia verruciformis, oral papillomatosis, lupus erythematosus, bullous diseases, bullous pemphigoid, scleroderma, actinic keratosis, pigmentation disorders, vitiligo, alopecia greata, Alzheimer's disease, Parkinson's disease, Huntington's disease, Pick's disease, Kuf's disease, Lewy Body disease, neurofibrillary tangles, Rosenthal fibers, Mallory's hyaline, senile dementia, myasthenia gravis, Gilles de la Tourette syndrome, multiple sclerosis, amyotrophic lateral sclerosis, progressive supranuclear palsy, epilepsy, Creutzfeldt-Jakob disease, deafness-dystonia syndrome, Leigh's disease, Leber's hereditary optic neuropathy, parkinsonism, dystonia, motor neurone disease, neuropathy syndrome, ataxia and retinitis pigmentosa, maternally inherited Leigh's disease, Friedreich's ataxia, hereditary spastic paraplegia, Mohr-Tranebjaerg syndrome, Wilson's disease, sporadic Alzheimer's disease, sporadic amyotrophic lateral sclerosis, sporadic Parkinson's disease, changes in autonomic function, hypertension, sleep disorders, neuropsychiatric disorders, depression, schizophrenia, schizoaffective disorder, Korsakoff psychosis, mania, anxiety disorders, phobic disorder, learning or memory disorders, amnesia or age-related memory loss, attention deficit disorder, dysthymic disorder, major depressive disorder, obsessive-compulsive disorder, disorders due to psychoactive substance use, panic disorder, affective bipolar disorder, migraines, hyperactivity disorders and movement disorders.

Another aspect of this invention relates to the use of at least one peptide of general formula (I), its stereoisomers, mixtures thereof and/or its cosmetically or pharmaceutically acceptable salts, in the preparation of a cosmetic or pharmaceutical composition for the treatment and/or care of the skin.

In another particular aspect, this invention relates to the use of one peptide of general formula (I), its stereoisomers, mixtures thereof and/or its cosmetically or pharmaceutically acceptable salts in the preparation of a cosmetic or pharmaceutical composition which increases or reduces the volume of the adipose tissue, preferably of the subcutaneous adipose tissue, more preferably of the subcutaneous adipose tissue of the thighs, breasts, lower part of the neck, neckline, buttocks, face, lips, cheeks, eyelids and/or hands.

In another particular aspect, this invention relates to the use of one peptide of general formula (I), its stereoisomers, mixtures thereof and/or its cosmetically or pharmaceutically acceptable salts in the preparation of a cosmetic or pharmaceutical composition which increases or reduces the triglyceride content of the adipose tissue, preferably of the subcutaneous adipose tissue, more preferably of the subcutaneous adipose tissue of the thighs, breasts, lower part of the neck, neckline, buttocks, face, lips, cheeks, eyelids and/or hands.

In another particular aspect, this invention relates to the use of one peptide of general formula (I), its stereoisomers, mixtures thereof and/or its cosmetically or pharmaceutically acceptable salts in the preparation of a cosmetic or pharmaceutical composition which reduces, prevents or delays the appearance of cellulitis.

In another aspect, this invention refers to a peptide of general formula (I), its stereoisomers, mixtures thereof and/or its cosmetically or pharmaceutically acceptable salts in the preparation of a cosmetic or pharmaceutical composition which reduces, delays and/or prevents the signs of aging and/or photoaging.

According to a preferred embodiment, this invention refers to the use of a peptide of general formula (I), its stereoisomers, mixtures thereof and/or its cosmetically or pharmaceutically acceptable salts in the preparation of a cosmetic or pharmaceutical composition which increases the temperature of the skin.

In another aspect, this invention relates to a method for the modulation of PGC-1α, which comprises the administration of a cosmetically or pharmaceutically effective amount of at least one peptide of general formula (I), its stereoisomers, mixtures thereof and/or their cosmetically or pharmaceutically acceptable salts.

In another aspect, this invention relates to a method for the modulation of PPARγ, which comprises the administration of a cosmetically or pharmaceutically effective amount of at least one peptide of general formula (I), its stereoisomers, mixtures thereof and/or their cosmetically or pharmaceutically acceptable salts.

In another aspect, this invention relates to a method for the treatment and/or care of diseases and/or disorders selected from the group formed by metabolic diseases and/or disorders such as diseases related to lipid metabolism, changes to gluconeogenesis, obesity, type 2 diabetes, cellulitis, gynecomastia, pseudogynecomastia, lipoatrophy, semicircular lipoatrophy, lipodystrophy, aging, photoaging, cutaneous traumas, reepithelialization of injuries, dehydration of the skin, xerosis, keratinization disorders, callouses, hard skin, psoriasis, lichen planus, skin lesions associated with lupus, dermatitis, atopic dermatitis, seborrheic dermatitis, senile dermatitis, dandruff, cradle cap, seborrhea, hyperseborrhea of acne, solar dermatitis, seborrheic keratosis, senile keratosis, actinic keratosis, photoinduced keratosis, follicular keratosis, acne vulgar, nevus, keloids, change in the function of fibroblasts, nodular fascitis, scleroderma, Dupuytren's contracture, fibrous scar formation, disorders of the sebaceous glands, acne rosacea, polymorphic acne, comedones, polymorphous, rosacea, nodulocystic acne, conglobate acne, senile acne, ichthyosis, Darier's disease, keratodermia palmoplantaris, leukoplakia, mucosal lichen, cutaneous lichen, cutaneous psoriasis, mucosal psoriasis, nail psoriasis, psoriatic rheumatism, eczema, common warts, flat warts, epidermodysplasia verruciformis, oral papillomatosis, lupus erythematosus, bullous diseases, bullous pemphigoid, scleroderma, actinic keratosis, pigmentation disorders, vitiligo, alopecia greata, Alzheimer's disease, Parkinson's disease, Huntington's disease, Pick's disease, Kuf's disease, Lewy Body disease, neurofibrillary tangles, Rosenthal fibers, Mallory's hyaline, senile dementia, myasthenia gravis, Gilles de la Tourette syndrome, multiple sclerosis, amyotrophic lateral sclerosis, progressive supranuclear palsy, epilepsy, Creutzfeldt-Jakob disease, deafness-dystonia syndrome, Leigh's disease, Leber's hereditary optic neuropathy, parkinsonism, dystonia, motor neurone disease, neuropathy syndrome, ataxia and retinitis pigmentosa, maternally inherited Leigh's disease, Friedreich's ataxia, hereditary spastic paraplegia, Mohr-Tranebjaerg syndrome, Wilson's disease, sporadic Alzheimer's disease, sporadic amyotrophic lateral sclerosis, sporadic Parkinson's disease, changes in autonomic function, hypertension, sleep disorders, neuropsychiatric disorders, depression, schizophrenia, schizoaffective disorder, Korsakoff psychosis, mania, anxiety disorders, phobic disorder, learning or memory disorders, amnesia or age-related memory loss, attention deficit disorder, dysthymic disorder, major depressive disorder, obsessive-compulsive disorder, disorders due to psychoactive substance use, panic disorder, affective bipolar disorder, migraines, hyperactivity disorders and movement disorders, which comprises the administration of a cosmetically or pharmaceutically effective amount of at least one peptide of general formula (I), its stereoisomers, mixtures thereof and/or their cosmetically or pharmaceutically acceptable salts.

Alternatively, this invention relates to a method for the treatment and/or care of the skin which comprises the administration of a cosmetically or pharmaceutically effective amount of at least one peptide of general formula (I), its stereoisomers, mixtures thereof and/or their cosmetically or pharmaceutically acceptable salts.

In another particular aspect, this invention relates to a method for increasing or reducing the volume of the adipose tissue, preferably of the subcutaneous adipose tissue, more preferably of the subcutaneous adipose tissue of the thighs, breasts, lower part of the neck, neckline, buttocks, face, lips, cheeks, eyelids and/or hands, which comprises the administration of a cosmetically or pharmaceutically effective amount of at least one peptide of general formula (I), its stereoisomers, mixtures thereof and/or their cosmetically or pharmaceutically acceptable salts.

In another particular aspect, this invention relates to a method for increasing or reducing the triglyceride content of the adipose tissue, preferably of the subcutaneous adipose tissue, more preferably of the subcutaneous adipose tissue of the thighs, breasts, lower part of the neck, neckline, buttocks, face, lips, cheeks, eyelids and/or hands, which comprises the administration of a cosmetically or pharmaceutically effective amount of at least one peptide of general formula (I), its stereoisomers, mixtures thereof and/or their cosmetically or pharmaceutically acceptable salts.

In another particular aspect, this invention relates to a method for reducing, preventing or delaying the appearance of cellulitis which comprises the administration of a cosmetically or pharmaceutically effective amount of at least one peptide of general formula (I), its stereoisomers, mixtures thereof and/or their cosmetically or pharmaceutically acceptable salts.

In another aspect, this invention relates to a method for reducing, delaying and/or preventing the signs of aging and/or photoaging which comprises the administration of a cosmetically or pharmaceutically effective amount of at least one peptide of general formula (I), its stereoisomers, mixtures thereof and/or their cosmetically or pharmaceutically acceptable salts.

In another aspect, this invention relates to a method for increasing the temperature of the skin which comprises the administration of a cosmetically or pharmaceutically effective amount of at least one peptide of general formula (I), its stereoisomers, mixtures thereof and/or their cosmetically or pharmaceutically acceptable salts.

The frequency of application or administration can vary greatly, depending on the needs of each subject, with a recommendation of an application or administration range from once a month to ten times a day, preferably from once a week to four times a day, more preferably from three times a week to three times a day, even more preferably once or twice a day.

The following specific examples provided here illustrate the nature of this invention. These examples are included for illustrative purposes only and should not be construed as limitations on the invention claimed herein.

EXAMPLES

General Methodology

All reagents and solvents are of synthesis quality and are used without additional treatment.

Abbreviations

The abbreviations used for amino acids follow the 1983 IUPAC-IUB Joint Commission on Biochemical Nomenclature recommendations outlined in *Eur. J. Biochem.* (1984) 138:937.

®, resin; 2,6-diClZ, 2,6-dichlorobenzyl; 2-BrZ, 2-bromobenzyloxycarbonyl; 2-ClTrt®, 2-chlorotrityl resin; Ac, acetyl; Adpoc, 1-(1-adamantyl)-1-methylethoxy-carbonyl; AIDS, acquired immune deficiency syndrome; Ala, alanine; All, allyl; Alloc, allyloxycarbonyl; AM, 2-[4-aminomethyl-(2,4-dimethoxyphenyl)] phenoxyacetic acid; Arg, arginine; Boc, tert-butyloxycarbonyl; Bom, benzyloxymethyl; Bzl, benzyl; cAMP, cyclic adenosine monophosphate; Cbz, carboxybenzyl; cHx, cyclohexyl; ClZ, 2-chlorobenzyl; C-terminal, carboxy-terminal; DCM, dichloromethane; Dde, N-[1-(4,4-dimethyl-2,6-dioxocyclohex-1-ylidene)ethyl]; DIEA, N,N'-diisopropylethylamine; DIPCDI, N,N'-diisopropylcarbodiimide; Dmab, 4-(N-[1-(4,4-dimethyl-2,6-dioxocyclohexylidene)-3-methylbutyl]amino)benzyl, DMF, N,N-dimethylformamide; DNA, deoxyribonucleic acid; Dnp, 2,4-dinitrophenol; EDTA, ethylenediaminetetraacetic acid; equiv, equivalent; ESI-MS, electrospray ionization mass spectrometry; Fm, fluorenylmethyl; Fmoc, 9-fluorenylmethyloxycarbonyl; Gly, glycine; His, histidine; HOAt, 1-hydroxy-7-azabenzotriazole; HOBt, 1-hydroxybenzotriazole; HPLC, high performance liquid chromatography; HSP70, heat shock protein 70 kDa; Ile, isoleucine; INCI, International Nomenclature of Cosmetic Ingredients; ivDde, 1-(4,4-dimethyl-2,6-dioxocyclohexylidene)-3-methyl-butyl; MBHA, p-methylbenzhydrylamine; Me, methyl; MeCN, acetonitrile; MeOH, methanol; mRNA, messenger ribonucleic acid; Mtr, 4-methoxy-2,3,6-trimethylbenzenesulfonyl; Mts, mesitylenesulfonyl; Mtt, methoxytrityl or methyltrityl; N-terminal, amino-terminal; PAL, 5-(4-aminomethyl-3,5-dimethoxyphenoxy) valeric acid; Palm, palmitoyl; Pbf, 2,2,4,6,7-pentamethyldihydrobenzofuran-5-sulfonyl; PCR, polymerase chain reaction; PDM-2, pre-adipocyte differentiation medium; PGC-1α, PPARγ coactivator 1α; PGM™-2, pre-adipocyte growth medium; Pmc, 2,2,5,7,8-pentamethylchroman-6-sulfonyl; pNZ, p-nitrobenzyloxycarbonyl; PPARγ, peroxisome proliferator-activated receptor gamma; q.s, quantity sufficient; q.s.p, quantity sufficient for; RNA, ribonucleic acid; Ser, serine; tBu, tert-butyl; Teoc, 2-(trimethylsilyl)ethyloxycarbonyl; TFA, trifluoroacetic acid; THF, tetrahydrofuran; Thr, threonine; TIS, triisopropylsilane; Tos, tosyl or p-toluenesulfonyl; Troc, 2,2,2-trichloroethoxycarbonyl; Trt, triphenylmethyl or trityl; Tyr, tyrosine; Val, valine; Z, benzyloxycarbonyl.

Chemical Synthesis

All synthetic processes were carried out in polypropylene syringes fitted with porous polyethylene discs. All the reagents and solvents were synthesis quality and were used without any additional treatment. The solvents and soluble reagents were removed by suction. The Fmoc group was removed with piperidine-DMF (2:8, v/v) (at least 1×1 min, 1×5 min, 5 mL/g resin) [Lloyd Williams P. et al. (1997) "*Chemical Approaches to the Synthesis of Peptides and Proteins*" CRC, Boca Raton (Fla., USA)]. Washes between stages of deprotection, coupling, and, again, deprotection, were carried out with DMF (3×1 min) each time using 10 mL solvent/g resin. Coupling reactions were performed with 3 mL solvent/g resin. The control of the couplings was performed by carrying out the ninhydrin test [Kaiser E. et al. (1970) *Anal. Biochem.* 34: 595598] or chloranil test [Christensen T. (1979) *Acta Chem. Scand.* 33B: 763766]. All synthetic reactions and washes were carried out at 25° C.

HPLC chromatographic analysis was carried out with Shimadzu equipment (Kyoto, Japan) using a reversed-phase column thermostatized at 30° C. (250×4.0 mm, Kromasil $C_8$, 5 μm, Akzo Nobel, Sweden). The elution was carried out using a gradient of acetonitrile (+0.07% TFA) in water (+0.1% TFA) at a flow rate of 1 mL/min and detection was carried out at 220 nm. The electrospray ionization mass spectrometry was carried out in a WATERS Alliance ZQ 2000 detector using a mixture of MeCN:$H_2O$ 4:1 (+0.1% TFA) as the mobile phase and a flow rate of 0.2 mL/min.

Example 1

Prophetic

Obtaining Fmoc-$W_n$—$X_m$-$AA_1$-$AA_2$-$AA_3$-$AA_4$-$AA_5$-$AA_6$-$Y_p$—$Z_q$—O-2-ClTrt-®, Wherein $AA_1$ is -L-His- or -L-Ser-; $AA_2$ is -L-Ile- or -L-Val-; $AA_3$ is -L-Tyr- or -L-Val-; $AA_4$ is -L-Val-; AA$_5$ is -L Ala-, -L-Arg- or -Gly-; AA$_6$ is -L-Thr- or -L-Val-; and n, m, p and q are 0.

3.50 g of Fmoc-L-Thr(tBu)-OH or 2.99 g of Fmoc-L-Val-OH (8.8 mmol; 1 equiv) dissolved in 55 mL of DCM to which is added 1.3 mL of DIEA (7.6 mmol; 0.86 equiv) are coupled to the dry 2-chlorotrityl resin (5.5 g; 8.8 mmol). They are stirred for 5 min, after which 2.5 mL of DIEA are added (14.6 mmol; 1.66 equiv). The mixture was allowed to react for 40 min. The remaining chloride groups are blocked by treatment with 4.4 mL of MeOH.

The N-terminal Fmoc group is deprotected as described in the general methods and 14.27 g of Fmoc-L-Arg(Pbf)-OH, 7.25 g of Fmoc-L-Ala-OH or 6.54 g of Fmoc-Gly-OH (22 mmol; 2.5 equiv) are coupled onto the peptide resin in the presence of DIPCDI (3.39 mL; 22 mmol; 2.5 equiv) and HOBt (3.37 g; 22 mmol; 2.5 equiv) using DMF as a solvent for 1 hour. The resin is then washed as described in the general methods and the deprotection treatment of the Fmoc group is repeated to couple the following amino acid. Following the protocols described 7.47 g of Fmoc-L-Val-OH (22 mmol; 2.5 equiv); 7.47 g of Fmoc-L-Val-OH or 10.11 g of Fmoc-L-Tyr (tBu)-OH (22 mmol; 2.5 equiv); 7.78 g of Fmoc-L-Ile-OH or 7.47 g of Fmoc-L-Val-OH (22 mmol; 2.5 equiv) and subsequently 13.63 g of Fmoc-L-His(Trt)-OH or 8.44 g of Fmoc-L-Ser(tBu)-OH (22 mmol; 2.5 equiv) are sequentially coupled in the presence of each coupling of 3.37 g of HOBt (22 mmol; 2.5 equiv) and 3.39 mL of DIPCDI (22 mmol; 2.5 equiv).

After synthesis, the peptide resins are washed with DCM (5×3 min) and dried by nitrogen stream.

Example 2

Obtaining Fmoc-W$_n$—X$_m$-AA$_1$-AA$_2$-AA$_3$-AA$_4$-AA$_5$-AA$_6$-Y$_p$—Z$_q$-AM-MBHA-®, Wherein AA$_1$ is -L-His- or -L-Ser-; AA$_2$ is -L-Ile- or -L-Val-; AA$_3$ is -L-Tyr- or -L-Val-; AA$_4$ is -L-Val-; AA$_5$ is -L Ala-, -L-Arg- or -Gly-; AA$_6$ is -L-Thr- or -L-Val-; and n, m, p and q are 0.

Weights have been normalized. 6.85 g of the Fmoc-AM-MBHA resin with a functionalization of 0.73 mmol/g (5 mmol) were treated with piperidine-DMF according to the described general protocol in order to remove the Fmoc group. 4.97 g of Fmoc-L-Thr(tBu)-OH or 4.24 g of Fmoc-L-Val-OH (12.5 mmol; 2.5 equiv) were incorporated onto the deprotected resin in the presence of DIPCDI (1.93 mL; 12.5 mmol; 2.5 equiv) and HOBt (1.93 g; 12.5 mmol; 2.5 equiv) using DMF as a solvent for one hour.

The resin was then washed as described in the general methods and the deprotection treatment of the Fmoc group was repeated to couple the next amino acid. Following the previously described protocols 4.12 g of Fmoc-L-Ala-OH, 8.11 g of Fmoc-L-Arg(Pbf)-OH or 3.72 g of Fmoc-Gly-OH (12.5 mmol; 2.5 equiv); 4.24 g of Fmoc-L-Val-OH (12.5 mmol; 2.5 equiv); 5.74 g of Fmoc-L-Tyr(tBu)-OH or 4.24 g of Fmoc-L-Val-OH (12.5 mmol; 2.5 equiv); 4.42 g of Fmoc-L-Ile-OH or 4.24 g of Fmoc-L-Val-OH (12.5 mmol; 2.5 equiv); and subsequently 7.75 g of Fmoc-L-His(Trt)-OH or 4.79 g of Fmoc-L-Ser(tBu)-OH (12.5 mmol; 2.5 equiv) were coupled sequentially each coupling in the presence of 1.93 g of HOBt (12.5 mmol; 2.5 equiv) and 1.93 mL of DIPCDI (12.5 mmol; 2.5 equiv).

After the synthesis, the peptide resins were washed with DCM (5×3 min) and dried by nitrogen stream.

Example 3

General Process for Removal of Fmoc N-Terminal Protective Group.

Weights have been normalized. The N-terminal Fmoc group of the peptide resins obtained in example 2 was deprotected as described in the general methods (20% piperidine in DMF). The peptide resins were washed with DMF (5×1 min), DCM (4×1 min), diethyl ether (4×1 min) and dried under vacuum. The same process could have been applied to the N-terminal Fmoc group of the peptidyl resin obtained in prophetic Example 1.

Example 4

Prophetic

Process for Introducing the R1 Palmitoyl Group onto the Peptide Resins Obtained in Example 3.

2.56 g of palmitic acid (10 mmol; 10 equiv) pre-dissolved in DMF (1 mL) are added onto 1 mmol of the peptide resins obtained in Example 3, in the presence of 1.53 g of HOBt (10 mmol; 10 equiv) and 1.54 mL of DIPCDI (10 mmol; 10 equiv). They are allowed to react for 15 hours, after which the resins are washed with THF (5×1 min), DCM (5×1 min), DMF (5×1 min), MeOH (5×1 min), DMF (5×1 min) THF (5×1 min), DMF (5×1 min), DCM (4×1 min), ether (3×1 min), and are dried under vacuum.

Example 5

Process for Introducing the R1 Acetyl Group onto the Peptide Resins Obtained in Example 3.

Weights have been normalized. 1 mmol of peptide resins obtained in Example 3 was treated with 25 equiv of acetic anhydride in the presence of 25 equiv of DIEA using 5 mL of DMF as a solvent. They were allowed to react for 30 min, after which the peptide resins were washed with DMF (5×1 min), DCM (4×1 min), diethyl ether (4×1 min) and were dried under vacuum.

Example 6

Prophetic

Cleavage Process from the Polymeric Support of the Peptide Resins Obtained in Examples 3, 4 and 5.

Weights have been normalized. 200 mg of the dried peptide resins obtained in Example 5 are treated with 5 mL of TFA:TIS:H2O (90:5:5) for 2 hours at room temperature under stirring. Filtrates are collected onto 50 mL cold diethyl ether, they are filtered through polypropylene syringes fitted with porous polyethylene discs and washed 5 times with 50 mL diethyl ether. The final precipitates were dried under vacuum.

HPLC analysis of the obtained peptides in gradients of MeCN (+0.07% TFA) in H2O (+0.1% TFA) showed a purity exceeding 80% in all cases. The identity of the peptides obtained was confirmed by ESI-MS. The same procedures could be applied to the peptidyl resins obtained in Examples 3 and 4.

Example 7

Prophetic

Cleavage Process of the Polymeric Support and Functionalization with R2 Substituted Amine: Obtaining Fmoc-W$_n$—

$X_m$-$AA_1$-$AA_2$-$AA_3$-$AA_4$-$AA_5$-$AA_6$-$Y_p$-$Z_q$—NH—$(CH_2)_{15}$—$CH_3$, Wherein $AA_1$ is -L-His- or -L-Ser-; $AA_2$ is -L-Ile- or -L-Val-; $AA_3$ is -L-Tyr- or -L-Val-; $AA_4$ is -L-Val-; $AA_5$ is -L-Ala-, -L-Arg- or -Gly-; $AA_6$ is -L-Thr- or -L-Val-; and n, m, p and q are 0.

The peptides Ac—$W_n$—$X_m$-$AA_1$-$AA_2$-$AA_3$-$AA_4$-$AA_5$-$AA_6$-$Y_p$-$Z_q$—OH with fully protected side chains are obtained by treating 150 mg of the peptide resins Ac—$W_n$—$X_m$-$AA_1$-$AA_2$-$AA_3$-$AA_4$-$AA_5$-$AA_6$-$Y_p$-$Z_q$—O-2-ClTrt-® of Example 5, previously desiccated under vacuum in the presence of KOH, with 3 mL of a 3% solution of TFA in DCM for 5 min. The filtrates are collected onto 50 mL of cold diethyl ether and the treatment is repeated three times. Ethereal solutions are evaporated to dryness at reduced pressure and room temperature, the precipitates are redissolved in 50% MeCN in $H_2O$ and lyophilized. 10 mg of the obtained crude peptides are weighed in a flask and 3 equiv of hexadecylamine and 25 mL of anhydrous DMF are added. 2 equiv of DIPCDI are added, and left to react being magnetically stirred at 47° C. The reactions are monitored by HPLC until disappearance of the initial products, which are complete after 24-48 hours. Solvents are evaporated to dryness and co-evaporated twice with DCM. The obtained residues [Ac—$W_n$—$X_m$-$AA_1$-$AA_2$-$AA_3$-$AA_4$-$AA_5$-$AA_6$-$Y_p$-$Z_q$—NH—$(CH_2)_{15}$—$CH_3$ with fully protected side chains] are redissolved in 25 mL of a mixture of TFA-DCM-anisole (49:49:2) and left to react for 30 min at room temperature. 250 mL of cold diethyl ether are added, the solvents are evaporated under reduced pressure and two additional co-evaporations with ether are carried out. The residues are dissolved in a mixture of 50% MeCN in $H_2O$ and lyophilized.

HPLC analysis of the obtained peptides in gradients of MeCN (+0.07% TFA) in $H_2O$ (+0.1% TFA) show a purity exceeding 60% in all cases. The identity of the peptides obtained is confirmed by ESI-MS.

Example 8

Prophetic

Modulation of the Human PGC-1α Promoter Activity.

The modulation capacity of the promoter of human PGC-1α is evaluated by the peptides in the invention in the hepatocellular Hep G2 carcinoma cell line transfected with the luciferase gene under the regulation of the human PGC-1α promoter. The cells are seeded at a density of 20,000 cells/25 $cm^2$ plate) and incubated for 24 hours in RPMI-1640 complete medium, after which the peptides of the invention are added at 0.5 mg/mL and are incubated for another 24 hours. The RPMI-1640 complete medium (carrier) is used as a negative control. The measurement of the promoter's activity is carried out using the Steady-Glo® Luciferase Assay System (PROMEGA) kit following the manufacturer's instructions. The luminescence values are read on a luminometer at 630 nm and the activity of the promoter is determined, which is normalized with regards to the values of the negative control.

TABLE 2

Modulation of the activity of the human PGC-1α promoter

| Treatment | Activity of the PGC-1α promoter (%) |
|---|---|
| Carrier | 100% |
| 0.5 mg/mL Ac-L-His-L-Val-L-Val-L-Val-L-Arg-L-Val-$NH_2$ (Ac-SEQ ID NO. 39-$NH_2$) | 186% |
| 0.5 mg/mL Ac-L-Ser-L-Ile-L-Val-L-Val-L-Arg-L-Val-$NH_2$ (Ac-SEQ ID NO. 38-$NH_2$) | 180% |
| 0.5 mg/mL Ac-L-Ser-L-Ile-L-Tyr-L-Val-L-Arg-L-Thr-$NH_2$ (Ac-SEQ ID NO. 11-$NH_2$) | 151% |
| 0.5 mg/mL Ac-L-Ser-L-Ile-L-Val-L-Val-L-Arg-L-Thr-$NH_2$ (Ac-SEQ ID NO. 15-$NH_2$) | 150% |
| 0.5 mg/mL Ac-L-Ser-L-Ile-L-Val-L-Val-L-Ala-L-Thr-$NH_2$ (Ac-SEQ ID NO. 7-$NH_2$) | 145% |
| 0.5 mg/mL Ac-L-Ser-L-Val-L-Val-L-Val-L-Arg-L-Val-$NH_2$ (Ac-SEQ ID NO. 40-$NH_2$) | 141% |
| 0.5 mg/mL Ac-L-Ser-L-Val-L-Tyr-L-Val-L-Arg-L-Val-$NH_2$ (Ac-SEQ ID NO. 36-$NH_2$) | 136% |
| 0.5 mg/mL Ac-L-Ser-L-Ile-L-Tyr-L-Val-L-Arg-L-Val-$NH_2$ (Ac-SEQ ID NO. 34-$NH_2$) | 134% |
| 0.5 mg/mL Ac-L-His-L-Val-L-Tyr-L-Val-L-Arg-L-Val-$NH_2$ (Ac-SEQ ID NO. 35-$NH_2$) | 132% |
| 0.5 mg/mL Ac-L-Ser-L-Val-L-Tyr-L-Val-L-Arg-L-Thr-$NH_2$ (Ac-SEQ ID NO. 13-$NH_2$) | 131% |
| 0.5 mg/mL Ac-L-Ser-L-Ile-L-Val-L-Val-L-Ala-L-Val-$NH_2$ (Ac-SEQ ID NO. 30-$NH_2$) | 120% |
| 0.5 mg/mL Ac-L-His-L-Ile-L-Val-L-Val-L-Arg-L-Val-$NH_2$ (Ac-SEQ ID NO. 37-$NH_2$) | 118% |
| 0.5 mg/mL Ac-L-His-L-Ile-L-Tyr-L-Val-L-Arg-L-Val-$NH_2$ (Ac-SEQ ID NO. 33-$NH_2$) | 117% |
| 0.5 mg/mL Ac-L-His-L-Ile-L-Tyr-L-Val-L-Arg-L-Thr-$NH_2$ (Ac-SEQ ID NO. 10-$NH_2$) | 115% |
| 0.5 mg/mL Ac-L-His-L-Val-L-Tyr-L-Val-L-Arg-L-Thr-$NH_2$ (Ac-SEQ ID NO. 12-$NH_2$) | 114% |
| 0.5 mg/mL Ac-L-Ser-L-Val-L-Val-L-Val-L-Arg-L-Thr-$NH_2$ (Ac-SEQ ID NO. 2-$NH_2$) | 114% |
| 0.5 mg/mL Ac-L-His-L-Ile-L-Val-L-Val-L-Gly-L-Thr-$NH_2$ (Ac-SEQ ID NO. 21-$NH_2$) | 110% |
| 0.5 mg/mL Ac-L-Ser-L-Val-L-Val-L-Val-L-Gly-L-Thr-$NH_2$ (Ac-SEQ ID NO. 24-$NH_2$) | 90% |
| 0.5 mg/mL Ac-L-His-L-Val-L-Val-L-Val-L-Ala-L-Thr-$NH_2$ (Ac-SEQ ID NO. 8-$NH_2$) | 89% |

TABLE 2-continued

Modulation of the activity of the human PGC-1α promoter

| Treatment | Activity of the PGC-1α promoter (%) |
|---|---|
| 0.5 mg/mL Ac-L-Ser-L-Val-L-Val-L-Val-L-Ala-L-Val-NH₂ (Ac-SEQ ID NO. 32-NH₂) | 82% |
| 0.5 mg/mL Ac-L-His-L-Ile-L-Val-L-Val-L-Ala-L-Val-NH₂ (Ac-SEQ ID NO. 29-NH₂) | 81% |
| 0.5 mg/mL Ac-L-Ser-L-Ile-L-Val-L-Val-Gly-L-Val-NH₂ (Ac-SEQ ID NO. 46-NH₂) | 78% |
| 0.5 mg/mL Ac-L-His-L-Val-L-Tyr-L-Val-L-Ala-L-Thr-NH₂ (Ac-SEQ ID NO. 4-NH₂) | 77% |
| 0.5 mg/mL Ac-L-Ser-L-Val-L-Tyr-L-Val-Gly-L-Thr-NH₂ (Ac-SEQ ID NO. 20-NH₂) | 76% |
| 0.5 mg/mL Ac-L-His-L-Ile-L-Tyr-L-Val-L-Ala-L-Val-NH₂ (Ac-SEQ ID NO. 25-NH₂) | 76% |
| 0.5 mg/mL Ac-L-Ser-L-Ile-L-Tyr-L-Val-L-Ala-L-Val-NH₂ (Ac-SEQ ID NO. 26-NH₂) | 40% |
| 0.5 mg/mL Ac-L-His-L-Val-L-Tyr-L-Val-Gly-L-Val-NH₂ (Ac-SEQ ID NO. 43-NH₂) | 75% |
| 0.5 mg/mL Ac-L-Ser-L-Val-L-Val-L-Val-Gly-L-Val-NH₂ (Ac-SEQ ID NO. 48-NH₂) | 75% |
| 0.5 mg/mL Ac-L-His-L-Ile-L-Val-L-Val-L-Ala-L-Thr-NH₂ (Ac-SEQ ID NO. 6-NH₂) | 72% |
| 0.5 mg/mL Ac-L-Ser-L-Val-L-Tyr-L-Val-L-Ala-L-Thr-NH₂ (Ac-SEQ ID NO. 5-NH₂) | 69% |
| 0.5 mg/mL Ac-L-Ser-L-Val-L-Tyr-L-Val-Gly-L-Val-NH₂ (Ac-SEQ ID NO. 44-NH₂) | 67% |
| 0.5 mg/mL Ac-L-Ser-L-Ile-L-Tyr-L-Val-Gly-L-Thr-NH₂ (Ac-SEQ ID NO. 18-NH₂) | 64% |
| 0.5 mg/mL Ac-L-Ser-L-Ile-L-Tyr-L-Val-Gly-L-Val-NH₂ (Ac-SEQ ID NO. 42-NH₂) | 64% |
| 0.5 mg/mL Ac-L-Ser-L-Ile-L-Val-L-Val-Gly-L-Thr-NH₂ (Ac-SEQ ID NO. 22-NH₂) | 63% |
| 0.5 mg/mL Ac-L-Ser-L-Val-L-Val-L-Val-L-Ala-L-Thr-NH₂ (Ac-SEQ ID NO. 9-NH₂) | 62% |
| 0.5 mg/mL Ac-L-Ser-L-Ile-L-Tyr-L-Val-L-Ala-L-Thr-NH₂ (Ac-SEQ ID NO. 1-NH₂) | 57% |
| 0.5 mg/mL Ac-L-His-L-Val-L-Tyr-L-Val-L-Ala-L-Val-NH₂ (Ac-SEQ ID NO. 27-NH₂) | 42% |

Example 9

Prophetic

Effect of the Peptides Ac-L-Ser-L-Ile-L-Tyr-L-Val-L-Ala-L-Thr-NH₂(Ac-SEQ ID NO. 1-NH₂) and Ac-L-Ser-L-Val-L-Val-L-Val-L-Arg-L-Thr-NH₂(Ac-SEQ ID NO. 2-NH₂) on the Transcription of the PGC-1α Gene.

The expression levels of the gene PGC-1α are measured by PCR in quantitative real time. A cell line of subcutaneous human pre-adipocytes is incubated in PGM™-2 medium at a density of 100,000 cells/well in a volume of 100 μL for 24 hours. Differentiation is induced by changing the medium to PDM-2 in the presence of the peptides Ac-L-Ser-L-Ile-L-Tyr-L-Val-L-Ala-L-Thr-NH₂ (Ac-SEQ ID NO. 1-NH₂) and Ac-L-Ser-L-Val-L-Val-L-Val-L-Arg-L-Thr-NH₂ (Ac-SEQ ID NO. 2-NH₂) at 0.1 mg/mL for 10 days, after which the cells were lysed and the RNA is extracted. The PCR is carried out in quantitative real time using the Taqman® Gene Expression Cells-to-CT (Applied Biosystems) kit according to the manufacturer's instructions and with the appropriate probes (TaqMan® Hs01016719_m1 probe for the PGC-1α gene and Taqman® Hs99999901_s1 probe for the eukaryotic ribosomal subunit 18S, the endogenous control of expression) and the values are normalized with regards to the maximum differentiation controls (PDM-2 medium, maximum quantity of PGC-1α mRNA) and minimal differentiation (PGM™-2 medium, minimum quantity of PGC-1α mRNA).

Table 3 shows the values of relative quantification of mRNA of the PGC-1α gene after incubation with the different peptides at the stated concentrations.

TABLE 3

Relative quantification of PGC-1α mRNA in subcutaneous human adipocytes

| Treatment | % relative quantity of PGC-1α mRNA |
|---|---|
| PGM™-2 | 0% |
| PDM-2 | 100% |
| 0.1 mg/mL Ac-L-Ser-L-Ile-L-Tyr-L-Val-L-Ala-L-Thr-NH₂ (Ac-SEQ ID NO. 1-NH₂) | 63% |
| 0.1 mg/mL Ac-L-Ser-L-Val-L-Val-L-Val-L-Arg-L-Thr-NH₂ (Ac-SEQ ID NO. 2-NH₂) | 125% |

Example 10

Modulation of the Accumulation of Lipids.

The levels of accumulation of lipids in subcutaneous human pre-adipocytes were quantified using the AdipoRed™ (Lonza) reagent. 100,000 cells were cultivated per well in PGM™-2 medium at a final volume of 100 μL. After 24 hours, the differentiation from pre-adipocytes to mature adipocytes was induced changing the medium to PDM-2 in the presence of the different peptides at 0.1 mg/mL. After 10 days of treatment with the peptides in differentiation medium, the quantity of intracellular lipids was evaluated using the AdipoRed™ reagent following the manufacturer's instructions measuring the fluorescence of the samples (length of the excitation wave 485 nm and emission 535 nm) after adding the AdipoRed™ reagent. The fluorescence values were corrected with regards to the basal fluorescence and were normalized with regards to the maximum differentiation controls (PDM-2 medium, maximum accumulation of lipids) and minimum differentiation (PGM™-2 medium, minimum accumulation of lipids).

Table 4 shows the values of quantification of the intracellular lipids after incubation with the peptides indicated at the stated concentrations.

Beta sitosterol [INCI: Beta-Sitosterol] is added (phase A2) and Glycosylceramides IRB3 [INCI: Lecithin, Glycolipids] (phase A3) under constant stirring.

Evening primrose oil [INCI: Evening Primrose (*Oenothera biennis*) Oil], borage seed oil [INCI: *Borago Officinalis* Seed Oil], Vitamin F Glyceryl Ester CLR™ [INCI: Glyceryl Linoleate, Glyceryl Linolenate], and tocopheryl acetate [INCI: Tocopheryl Acetate] (phase B ingredients) are mixed under stirring and mixed with phase A at 40° C.

In a separate vessel isostearic acid [INCI: Isostearic Acid] and Empipearl XA 500™ [INCI: Water (Aqua), Sodium Laureth Sulfate, Glycol Cetearate, Cocamide DEA, Formaldehyde] are mixed under stirring (phase C ingredients) and then Ac-L-Ser-L-Val-L-Val-L-Val-Gly-L-Val-NH$_2$ (Ac-SEQ ID NO. 48-NH$_2$) is added (phase D) to the mixture. Denatured alcohol is added [INCI: Alcohol Denat] (phase E) under stirring. Lastly the mixture of phase A is poured into this mixture under stirring, obtaining a cosmetic composition with the proportions shown in Table 5.

TABLE 4

Accumulation of intracellular lipids in subcutaneous human adipocytes

| Treatment | % Accumulation of intracellular lipids |
|---|---|
| PGM ™-2 | 0% |
| PDM-2 | 100% |
| 0.1 mg/mL Ac-L-Ser-L-Ile-L-Tyr-L-Val-L-Ala-L-Thr-NH$_2$ (Ac-SEQ ID NO. 1-NH$_2$) | 33% |
| 0.1 mg/mL Ac-L-Ser-L-Val-L-Tyr-L-Val-L-Ala-L-Thr-NH$_2$ (Ac-SEQ ID NO. 5-NH$_2$) | 48% |
| 0.1 mg/mL Ac-L-Ser-L-Ile-L-Tyr-L-Val-L-Arg-L-Thr-NH$_2$ (Ac-SEQ ID NO. 11-NH$_2$) | 76% |
| 0.1 mg/mL Ac-His-L-Val-L-Tyr-L-Val-L-Arg-L-Thr-NH$_2$ (Ac-SEQ ID NO. 12-NH$_2$) | 84% |
| 0.1 mg/mL Ac-L-Ser-L-Val-L-Tyr-L-Val-L-Arg-L-Thr-NH$_2$ (Ac-SEQ ID NO. 13-NH$_2$) | 79% |
| 0.1 mg/mL Ac-L-Ser-L-Val-L-Val-L-Val-L-Arg-L-Thr-NH$_2$ (Ac-SEQ ID NO. 2-NH$_2$) | 128% |
| 0.1 mg/mL Ac-His-L-Ile-L-Val-L-Val-Gly-L-Thr-NH$_2$ (Ac-SEQ ID NO. 21-NH$_2$) | 114% |
| 0.1 mg/mL Ac-L-Ser-L-Ile-L-Val-L-Val-Gly-L-Thr-NH$_2$ (Ac-SEQ ID NO. 22-NH$_2$) | 43% |
| 0.1 mg/mL Ac-L-Ser-L-Ile-L-Val-L-Val-Gly-L-Val-NH$_2$ (Ac-SEQ ID NO. 46-NH$_2$) | 38% |
| 0.1 mg/mL Ac-L-Ser-L-Val-L-Val-L-Val-Gly-L-Val-NH$_2$ (Ac-SEQ ID NO. 48-NH$_2$) | 37% |

Example 11

Prophetic

Preparation of a Water in Oil Microemulsion (W/O) Containing Ac-L-Ser-L-Val-L-Val-L-Val-Gly-L-Val-NH$_2$(Ac-SEQ ID NO. 48-NH$_2$).

In a suitable vessel the following are mixed together: caprylic/capric triglyceride [INCI: Caprylic/Capric Triglyceride], oleic acid [INCI: Oleic Acid], Edenor LS2M GS [INCI: Stearic Acid, Palmitic Acid] and ceramide [INCI: Ceramide 3] (phase A1 ingredients), and heated to 80-85° C.

TABLE 5

Microemulsion

| Phase | Ingredients | % in weight |
|---|---|---|
| A1 | CAPRYLIC/CAPRIC TRIGLYCERIDE | c.s.p. 100 |
| A1 | OLEIC ACID | 0.018 |
| A1 | EDENOR L2SM GS | 0.0045 |
| A1 | CERAMIDE 3 | 0.0045 |

TABLE 5-continued

Microemulsion

| Phase | Ingredients | % in weight |
|---|---|---|
| A2 | BETA SITOSTEROL | 0.0225 |
| A3 | GLYCOSYLCERAMIDES IRB 3 | 0.0135 |
| B | EVENING PRIMROSE (*OENOTHERA BIENNIS*) OIL | 9 |
| B | *BORAGO OFFICINALIS* SEED OIL | 9 |
| B | VITAMIN F GLYCERYL ESTER CLR | 4.5 |
| B | TOCOPHERYL ACETATE | 0.45 |
| C | ISOSTEARIC ACID | 7.87 |
| C | EMPIPEARL XA 500 | 1.39 |
| D | Ac-L-Ser-L-Val-L-Val-L-Val-Gly-L-Val-NH$_2$ (Ac-SEQ ID NO. 48-NH$_2$) | 0.001 |
| E | ALCOHOL DENAT. | 0.745 |

Example 12

Prophetic

Preparation of Coacervates of Nanostructured Lipid Carriers Containing Ac-L-Ser-L-Val-L-Val-L-Val-L-Arg-L-Thr-NH$_2$ (Ac-SEQ ID NO. 2-NH$_2$).

In a suitable vessel the following are added in this order: water [INCI: Water (Aqua)], starch hydroxypropyl starch phosphate [INCI: Hydroxypropyl Starch Phosphate], sclerotium gum [INCI: Sclerotium Gum], sodium hyaluronate [INCI: Sodium Hyaluronate], propanediol [INCI: Propanediol], phenoxyethanol [INCI: Phenoxyethanol] (phase A ingredients). The mixture of ingredients from phase A is heated at 65° C.

In another vessel sorbitan sesquiolate [INCI: Sorbitan Sesquiolate], and isohexadecane [INCI: Isohexadecane] are added (phase B ingredients) and are dissolved at 60-65° C.

In a third vessel water [INCI: Water (Aqua)], Ac-L-Ser-L-Val-L-Val-L-Val-L-Arg-L-Thr-NH$_2$ (Ac-SEQ ID NO. 2-NH$_2$), soybean oil [INCI: Soybean (*Glycine Soja*) Oil], sorbitan tristearate [INCI: Sorbitan Tristearate] and cetyl PEG/PPG-10/1 dimethicone [INCI: Cetyl PEG/PPG-10/1 Dimethicone] are mixed (phase B1 ingredients).

In another vessel water [INCI: Water (Aqua)] and Quat-soy LDMA-25 [INCI: Water (Aqua), Lauryldimonium Hydroxypropyl Hydrolyzed Soy Protein] are mixed (phase C ingredients).

In another vessel hydroxypropyl starch phosphate [INCI: Hydroxypropyl Starch Phosphate], Sclerotium gum [INCI: Sclerotium Gum] are mixed (phase D ingredients).

Phase B1 is added to phase B. The mixture is added to phase A under constant stirring and is microfluidified. Phase C and phase D are added under constant stirring, obtaining a composition with the proportions shown in Table 6.

TABLE 6

Coacervates of nanostructured lipid carriers

| Phase | Ingredients | % weight |
|---|---|---|
| A | WATER (AQUA) | c.s.p. 100 |
| A | HYDROXYPROPYL STARCH PHOSPHATE | 1 |
| A | SCLEROTIUM GUM | 0.5 |
| A | SODIUM HYALURONATE | 0.01 |
| A | PROPANEDIOL | 5 |
| A | PHENOXYETHANOL | 2.6 |
| B | SORBITAN SESQUIOLEATE | 4 |
| B | ISOHEXADECANE | 5 |
| B1 | WATER (AQUA) | 16.75 |
| B1 | Ac-L-Ser-L-Val-L-Val-L-Val-L-Arg-L-Thr-NH$_2$ (Ac-SEQ ID NO. 2-NH$_2$) | 0.05 |
| B1 | SOYBEAN (*GLYCINE SOJA*) OIL | 11.1 |
| B1 | SORBITAN TRISTEARATE | 0.6 |
| B1 | CETYL PEG/PPG-10/1 DIMETHICONE | 1.5 |
| C | WATER (AQUA) | 6 |
| C | QUAT-SOY LDMA-25 | 0.2 |
| D | HYDROXYPROPYL STARCH PHOSPHATE | 1.5 |
| D | SCLEROTIUM GUM | 0.75 |

Example 13

Prophetic

Preparation of Nanocapsules of Microemulsion Containing Ac-L-Ser-L-Ile-L-Tyr-L-Val-L-Ala-L-Thr-NH$_2$(Ac-SEQ ID NO. 1-NH$_2$).

In a suitable vessel water [INCI: water (AQUA)], hydroxypropyl starch phosphate [INCI: Hydroxypropyl Starch Phosphate], sclerotium gum [INCI: Sclerotium Gum], sodium hyaluronate [INCI: Sodium Hyaluronate], propanediol [INCI: Propanediol], phenoxyethanol [INCI: Phenoxyethanol] are added (phase A ingredients). The mixture of phase A ingredients was heated to 65° C.

In another vessel Ac-L-Ser-L-Ile-L-Tyr-L-Val-L-Ala-L-Thr-NH$_2$ (Ac-SEQ ID NO. 1-NH$_2$), soybean oil [INCI: Soybean (*Glycine Soja*) oil], sorbitan sesquiolate [INCI: Sorbitan Sesquiolate], and isohexadecane [INCI: Isohexadecane] are added (phase B ingredients).

In another vessel water [INCI: Water (Aqua)] and Quat-soy LDMA-25 [INCI: Water (Aqua), Lauryldimonium Hydroxypropyl Hydrolyzed Soy Protein] are mixed together (phase C ingredients).

In another vessel hydroxypropyl starch phosphate [INCI: Hydroxypropyl Starch Phosphate], sclerotium gum [INCI: Sclerotium Gum] are mixed together (phase D ingredients).

Mixture B was poured into phase A under constant stirring and the mixture is microfluidified. Phase C and phase D are added under constant stirring, obtaining a cosmetic composition with the proportions shown in Table 7.

TABLE 7

Nanocapsules of microemulsions

| Phase | Ingredients | % weight |
|---|---|---|
| A | WATER (AQUA) | c.s.p. 100 |
| A | HYDROXYPROPYL STARCH PHOSPHATE | 1 |
| A | SCLEROTIUM GUM | 0.52 |
| A | SODIUM HYALURONATE | 0.01 |
| A | PROPANEDIOL | 5 |
| A | PHENOXYETHANOL | 2.6 |
| B | SORBITAN SESQUIOLEATE | 5.3 |
| B | ISOHEXADECANE | 3.2 |
| B1 | Ac-L-Ser-L-Ile-L-Tyr-L-Val-L-Ala-L-Thr-NH$_2$ (Ac-SEQ ID NO. 1-NH$_2$) | 0.05 |
| B1 | SOYBEAN (*GLYCINE SOJA*) OIL | 5 |
| C | WATER (AQUA) | 6 |
| C | QUAT-SOY LDMA-25 | 0.2 |
| D | HYDROXYPROPYL STARCH PHOSPHATE | 1.5 |
| D | SCLEROTIUM GUM | 0.75 |

TABLE 8

Cosmetic facial composition

| Phase | Ingredients | % in weight |
|---|---|---|
| A | WATER (AQUA) | c.s.p. 100 |
| A | PENTYLENE GLYCOL | 4.9 |
| A | BENZYL ALCOHOL | 0.98 |
| A1 | CARBOMER | 0.49 |
| A2 | POTASSIUM CETYL PHOSPHATE | 0.49 |
| B | C12-15 ALKYL BENZOATE | 4.9 |
| B | PHENOXYETHANOL | 0.88 |
| B | TOCOPHERYL ACETATE | 0.49 |
| B | DIMETHICONE | 0.98 |
| B | ETHYLHEXYL COCOATE | 2.45 |
| B | PHYTOCREAM 2000 ™ | 0.49 |
| C | SEPIGEL 305 ™ | 0.98 |
| D | SODIUM HYDROXIDE (20% in aqueous solution) | c.s. |
| E | FRAGANCE (PARFUM) | 0.098 |
| F | Ac-L-Ser-L-Val-L-Val-L-Val-L-Arg-L-Thr-NH$_2$ (Ac-SEQ ID NO. 2-NH$_2$) | 0.001 |

Example 14

Prophetic

Preparation of a Cosmetic Facial Composition Containing Ac-L-Ser-L-Val-L-Val-L-Val-L-Arg-L-Thr-NH$_2$(Ac-SEQ ID NO. 2-NH$_2$).

In a suitable vessel water [INCI: Water (Aqua)], Pentylene glycol [INCI: Pentylene Glycol], and benzyl alcohol [INCI: Benzyl Alcohol] are mixed together (phase A ingredients). Carbomer [INCI: Carbomer] (phase A1 ingredient) and potassium cetyl phosphate [INCI: Potassium Cetyl Phosphate] are added (phase A2 ingredient) to phase A under constant stirring until completely dissolved. The mixture is heated to 65-70° C.

Ethylhexyl cocoate [INCI: Ethylhexyl Cocoate], C12-C15 alkyl benzoate [INCI: C12-15 Alkyl Benzoate], Phytocream 2000™ [INCI: Glyceryl Stearate, Cetearyl Alcohol, Potassium Palmitoyl Hydrolyzed Wheat Protein] Phenoxyethanol [INCI: Phenoxyethanol], Tocopheryl acetate [INCI: Tocopheryl Acetate] and Dimethicone [INCI: Dimethicone] are mixed in another vessel (phase B ingredients) and the mixture is mixed together at 65-70° C. Phase B is added to phase A. It is cooled and Sepigel 305™ [INCI: Polyacrylamide, Water (Aqua), C13-14 Isoparaffin, Laureth-7] is added to it (phase C ingredients) under constant stirring. The pH is adjusted with sodium hydroxide [INCI: Sodium Hydroxide (20% in aqueous solution)] (phase D ingredient) and fragrance is added (phase E). Lastly Ac-L-Ser-L-Val-L-Val-L-Val-L-Arg-L-Thr-NH$_2$ (Ac-SEQ ID NO. 2-NH$_2$) (phase F) is added under stirring, obtaining a cosmetic composition with the proportions shown in Table 8.

Example 15

Prophetic

Preparation of a Corporal Cosmetic Composition Containing Nanocapsules of Microemulsions According to Example 13

In a suitable vessel water [INCI: Water (Aqua)], betaine [INCI: Betaine], glycerin [INCI: Glycerin], pentylene glycol [INCI: Pentylene Glycol] and benzyl alcohol [INCI: Benzyl Alcohol] are mixed together (phase A ingredients) until they dissolved. Carbomer [INCI: Carbomer] (phase A1) and potassium cetylphosphate are added (phase A2) under constant stirring and the mixture is heated to 65-70° C.

Isohexadecane [INCI: Isohexadecane], C12-15 alkyl benzoate [INCI: C12-15 Alkyl Benzoate], phenoxyethanol [INCI: Phenoxyethanol], Edenor L2SM [INCI: Stearic Acid, Palmitic Acid], cetyl alcohol [INCI: Cetyl Alcohol] and Polysorbate 20 are mixed in a separate vessel (phase B ingredients) and the mixture is heated to 65-70° C. Phase B is added to phase A. Cyclomethicone [INCI: Cyclomethicone] is added (phase C) at 40° C. The pH is adjusted with sodium hydroxide at 20% in an aqueous solution [INCI: Sodium Hydroxide] and the fragrance is added [INCI: Fragrance (parfum)]. The nanocapsules of microemulsions are added according to example 13 containing Ac-L-Ser-L-Ile-L-Tyr-L-Val-L-Ala-L-Thr-NH$_2$ (Ac-SEQ ID NO. 1-NH$_2$) (phase F) under constant stirring and are dissolved, obtaining a cosmetic composition with the proportions shown in Table 9.

TABLE 9

Corporal cosmetic composition

| Phase | Ingredients | % in weight |
|---|---|---|
| A | WATER (AQUA) | c.s.p. 100 |
| A | BETAINE | 2.99 |
| A | GLYCERIN | 2.99 |
| A | PENTYLENE GLYCOL | 4.99 |
| A | BENZYL ALCOHOL | 1 |
| A1 | CARBOMER | 0.3 |
| A2 | POTASSIUM CETYL PHOSPHATE | 0.4 |
| B | ISOHEXADECANE | 1 |
| B | C12-15 ALKYL BENZOATE | 1.5 |
| B | PHENOXYETHANOL | 0.9 |
| B | EDENOR L2SM GS | 0.5 |
| B | CETYL ALCOHOL | 1.79 |
| B | POLYSORBATE 20 | 0.8 |
| C | CYCLOMETHICONE | 2 |
| D | SODIUM HYDROXIDE (20% in aqueous solution) | c.s. |
| E | FRAGANCE (PARFUM) | 0.1 |
| F | Nanocapsules Example 13 | 2 |

Example 16

Preparation of a Corporal Cosmetic Composition Containing Ac-L-Ser-L-Val-L-Val-L-Val-L-Arg-L-Thr-$NH_2$(Ac-SEQ ID NO. 2-$NH_2$).

In a suitable vessel water [INCI: Water (Aqua)], betaine [INCI: Betaine], glycerin [INCI: Glycerin], pentylene glycol [INCI: Pentylene Glycol] and benzyl alcohol [INCI: Benzyl Alcohol] were mixed together (phase A ingredients) until they dissolved. Carbomer [INCI: Carbomer] (phase A1) and potassium cetylphosphate were added (phase A2) under constant stirring and the mixture was heated to 65-70° C.

Isohexadecane [INCI: Isohexadecane], C12-15 alkyl benzoate [INCI: C12-15 Alkyl Benzoate], phenoxyethanol [INCI: Phenoxyethanol], Edenor L2SM [INCI: Stearic Acid, Palmitic Acid], cetyl alcohol [INCI: Cetyl Alcohol] and Polysorbate 20 were mixed in a separate vessel (phase B ingredients) and the mixture was heated to 65-70° C. Phase B was added to phase A. Cyclomethicone [INCI: Cyclomethicone] was added (phase C) at 40° C. The pH was adjusted with sodium hydroxide at 20% in an aqueous solution [INCI: Sodium Hydroxide] and the fragrance was added [INCI: Fragrance (parfum)]. Ac-L-Ser-L-Val-L-Val-L-Val-L-Arg-L-Thr-$NH_2$ (Ac-SEQ ID NO. 2-$NH_2$) (phase F) was added under constant stirring and was dissolved, obtaining a cosmetic composition with the proportions shown in Table 10.

TABLE 10

Corporal cosmetic composition

| Phase | Ingredients | % in weight |
|---|---|---|
| A | WATER (AQUA) | c.s.p. 100 |
| A | BETAINE | 2.94 |
| A | GLYCERIN | 2.94 |
| A | PENTYLENE GLYCOL | 4.9 |
| A | BENZYL ALCOHOL | 0.98 |

TABLE 10-continued

Corporal cosmetic composition

| Phase | Ingredients | % in weight |
|---|---|---|
| A1 | CARBOMER | 0.29 |
| A2 | POTASSIUM CETYL PHOSPHATE | 0.39 |
| B | ISOHEXADECANE | 0.98 |
| B | C12-15 ALKYL BENZOATE | 1.47 |
| B | PHENOXYETHANOL | 0.88 |
| B | EDENOR L2SM GS | 0.49 |
| B | CETYL ALCOHOL | 1.76 |
| B | POLYSORBATE 20 | 0.78 |
| C | CYCLOMETHICONE | 1.96 |
| D | SODIUM HYDROXIDE (20% in aqueous solution) | c.s. |
| E | FRAGANCE (PARFUM) | 0.1 |
| F | Ac-L-Ser-L-Val-L-Val-L-Val-L-Arg-L-Thr-$NH_2$ (Ac-SEQ ID NO. 2-$NH_2$) | 0.001 |

Example 17

Prophetic

Effect of the Composition from Example 15 on the Reduction of Cellulitis.

20 Caucasian volunteers between the age of 25 and 45, with healthy skin and affected by cellulitis levels I-III according to the pinch test applied the composition from Example 15 to one thigh and a placebo composition (the same composition from Example 15 without the peptide) to the other thigh, twice a day for 21 days. The length of the dermo-hypodermic junction line was instrumentally assessed using the Ultrasound Scanner Dermascan C® (Cortex Technology, Denmark) at the beginning of the study and at the end of the study (21 days). The measurement of the length of the dermo-hypodermic junction line is related to the formation of cellulitis and skin irregularities [Quatresooz P et al., "*Cellulite histopathology and related mechanobiology*", (2006), *Int. J. Cosm. Sci.*, 28, 207-210]. A reduction in the length of the dermo-hypodermic junction line leads to softer and more regular skin, and as such cellulitis will be less visible.

The statistical analysis of the evolution of the parameters measured during the study was carried out using the Student's t-test. The statistical significance threshold was established at 5%.

The results of the study detailed in Table 11 show that treatment with the peptide Ac-L-Ser-L-Ile-L-Tyr-L-Val-L-Ala-L-Thr-$NH_2$ (Ac-SEQ ID NO. 1-$NH_2$) induces a reduction in the length of the dermo-hypodermic junction line after 21 days of treatment and therefore a reduction in cellulitis.

TABLE 11

Change in the skin's roughness and the dermo-hypodermic junction line

| | start | 21 days | Reduction (%) |
|---|---|---|---|
| Placebo Composition | 17.82 | 17.12 | −3.9% |
| Composition example 15 | 20.43 | 16.13 | −21.0% |

Example 18

Prophetic

Effect of the Composition of Example 16 on the Volume of the Breasts.

22 Caucasian volunteers between the age of 25 and 40, with healthy skin and a bra size of between 36 C to 40 E applied the composition from Example 16 to one breast and a placebo composition (the same composition from Example 16 without the peptide) to the other breast, twice a day for 56 days. The volume of the breasts was instrumentally assessed at the beginning of the study, after 14 days and 28 days of applying the compositions and at the end of the study (56 days) using the Fast Optical In Vivo Topometry Technique, which enables the volume of the breasts to be calculated in mm$^3$. The volume of the breasts was normalized initially at an arbitrary value of 100,000 mm$^3$ and the changes in volume of the breasts was measured at the different treatment times in relation to their initial volume.

The statistical analysis of the evolution of the parameters measured during the study was carried out using the Student's t-test or the Wilcoxon test. The statistical significance threshold was established at 5%.

The results from the study detailed in Table 12 show that treatment with the peptide Ac-L-Ser-L-Val-L-Val-L-Val-L-Arg-L-Thr-NH$_2$ (Ac-SEQ ID NO. 2-NH$_2$) induces an increase in the volume of the breasts.

TABLE 12

Change of breast volume

| Product | 14 days | 28 days | 56 days |
|---|---|---|---|
| Placebo composition | +7.78 mm$^3$ | +110.33 mm$^3$ | −29.96 mm$^3$ |
| Composition example 16 | +522.27 mm$^3$ | +848.52 mm$^3$ | +888.29 mm$^3$ |

The invention claimed is:

1. A peptide of general formula (I)

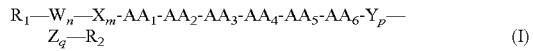

its stereoisomers, mixtures thereof and/or its cosmetic or pharmaceutical acceptable salts, wherein:

$AA_1$ is selected from the group consisting of -His- and -Ser-;

$AA_2$ is selected from the group consisting of -Ile- and -Val-;

$AA_3$ is selected from the group consisting of -Tyr- and -Val-, $AA_4$ is -Val-;

$AA_5$ is selected from the group consisting of -Ala-, -Arg- and -Gly-;

$AA_6$ is selected from the group consisting of -Thr- and -Val-;

W, X, Y and Z are amino acids and are independently selected from amongst themselves;

n, m, p and q are independently selected from amongst themselves and have a value of 0 or 1;

n+m+p+q is lower or equal to 2;

$R_1$ is selected from the group consisting of H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO—, wherein $R_5$ is selected from the group consisting of H, substituted or unsubstituted non-cyclic aliphatic group, substituted or unsubstituted alicyclyl, substituted or unsubstituted aryl, substituted or unsubstituted aralkyl, substituted or unsubstituted heterocyclyl, and substituted or unsubstituted heteroarylalkyl;

$R_2$ is selected from the group consisting of —$NR_3R_4$, —$OR_3$ and —$SR_3$, wherein $R_3$ and $R_4$ are independently selected from the group consisting of H, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl; and on condition that $R_1$ and $R_2$ are not α-amino acids.

2. The peptide according to claim 1, wherein $R_1$ is selected from the group consisting of H and $R_5$—CO— wherein $R_5$ is selected from the group consisting of substituted or unsubstituted alkyl $C_1$-$C_{24}$, substituted or unsubstituted alkenyl $C_2$-$C_{24}$, substituted or unsubstituted alkynyl $C_2$-$C_{24}$, substituted or unsubstituted cycloalkyl $C_3$-$C_{24}$, substituted or unsubstituted cycloalkenyl $C_5$-$C_{24}$, substituted or unsubstituted cycloalkynyl $C_8$-$C_{24}$, substituted or unsubstituted aryl $C_6$-$C_{30}$, substituted or unsubstituted aralkyl $C_7$-$C_{24}$, substituted or unsubstituted heterocyclyl with 3-10 ring members, and substituted or unsubstituted heteroarylalkyl of 2 to 24 carbon atoms and 1 to 3 atoms other than carbon and an alkyl chain of 1 to 6 carbon atoms.

3. The peptide according to claim 2, wherein $R_1$ is selected from the group consisting of H, acetyl, tert-butanol, hexanoyl, 2-methylhexanoyl, cyclohexanecarboxyl, octanoyl, decanoyl, lauroyl, myristoyl, palmitoyl, stearoyl, oleoyl, and linoleoyl.

4. The peptide according to claim 1, wherein $R_2$ is —$NR_3R_4$ or —$OR_3$, wherein $R_3$ and $R_4$ are independently selected from the group consisting of H, substituted or unsubstituted alkyl $C_1$-$C_{24}$, substituted or unsubstituted alkenyl $C_2$-$C_{24}$ substituted or unsubstituted alkynyl $C_2$-$C_{24}$, substituted or unsubstituted cycloalkyl $C_3$-$C_{24}$, substituted or unsubstituted cycloalkenyl $C_5$-$C_{24}$, substituted or unsubstituted cycloalkynyl $C_8$-$C_{24}$, substituted or unsubstituted aryl $C_6$-$C_{30}$, substituted or unsubstituted aralkyl $C_7$-$C_{24}$, substituted or unsubstituted heterocyclyl with 3-10 ring members, and substituted or unsubstituted heteroarylalkyl of 2 to 24 carbon atoms and 1 to 3 atoms other than carbon and an alkyl chain of 1 to 6 carbon atoms.

5. The peptide according to claim 4, wherein $R_3$ and $R_4$ are independently selected from the group consisting of H, methyl, ethyl, hexyl, dodecyl, and hexadecyl.

6. The peptide according to claim 1, wherein $R_1$ is selected from the group consisting of H, acetyl, lauroyl, myristoyl or palmitoyl, $AA_1$ is -L-Ser-, $AA_2$ is -L-Ile-, $AA_3$ is -L-Tyr-, $AA_4$ is -L-Val-, $AA_5$ is -L-Ala $AA_6$ is -L-Thr-, and $R_2$ is —$NR_3R_4$ or —$OR_3$, wherein $R_3$ and $R_4$ are independently selected from H, methyl, ethyl, hexyl, dodecyl, and hexadecyl.

7. The peptide according to claim 1, wherein $R_1$ is selected from the group consisting of H, acetyl, lauroyl, myristoyl and palmitoyl, $AA_1$ is -L-Ser-, $AA_2$ is -L-Val-, $AA_3$ is -L-Tyr-, $AA_4$ is -L-Val-, $AA_5$ is -L-Ala $AA_6$ is -L-Thr-, and $R_2$ is —$NR_3R_4$ or —$OR_3$, wherein $R_3$ and $R_4$ are independently selected from H, methyl, ethyl, hexyl, dodecyl, and hexadecyl.

8. The peptide according to claim 1, wherein $R_1$ is selected from the group consisting of H, acetyl, lauroyl, myristoyl and palmitoyl, $AA_1$ is -L-Ser-, $AA_2$ is -L-Ile-, $AA_3$ is -L-Val-, $AA_4$ is -L-Val-, $AA_5$ is -L-Gly $AA_6$ is -L-Thr- and $R_2$ is —$NR_3R_4$ or —$OR_3$, wherein $R_3$ and $R_4$ are independently selected from H, methyl, ethyl, hexyl, dodecyl, and hexadecyl.

9. The peptide according to claim 1, wherein $R_1$ is selected from the group consisting of H, acetyl, lauroyl, myristoyl, and palmitoyl, is -L-Ser-, $AA_2$ is -L-Val-, $AA_3$ is -L-Val-, $AA_4$ is -L-Val-, $AA_5$ is -L-Arg $AA_6$ is -L-Thr-, and $R_2$ is —$NR_3R_4$ or —$OR_3$, wherein $R_3$ and $R_4$ are independently selected from H, methyl, ethyl, hexyl, dodecyl, and hexadecyl.

10. The peptide according to claim 1, wherein $R_1$ is selected from the group consisting of H, acetyl, lauroyl, myristoyl and palmitoyl, $AA_1$ is -L-His-, $AA_2$ is -L-Ile-, $AA_3$ is -L-Val-, $AA_4$ is -L-Val-, $AA_5$ is -L-Gly $AA_6$ is -L-Thr-, and $R_2$ is —$NR_3R_4$ or —$OR_3$, wherein $R_3$ and $R_4$ are independently selected from H, methyl, ethyl, hexyl, dodecyl, and hexadecyl.

11. A process for preparing a peptide of general formula (I), its stereoisomers, mixtures thereof and/or its cosmetically or pharmaceutically acceptable salts, according to claim 1, wherein the preparation process is carried out in solid phase or solution.

12. A cosmetic or pharmaceutical composition which comprises a cosmetically or pharmaceutically effective amount of at least one peptide of general formula (I), its stereoisomers, mixtures thereof and/or its cosmetically or pharmaceutically acceptable salts, according to claim 1, and at least one cosmetically or pharmaceutically acceptable excipient or agent.

13. The composition according to claim 12, wherein the peptide of general formula (I), its stereoisomers, mixtures thereof and/or its cosmetically or pharmaceutically acceptable salts, is incorporated into a cosmetic or pharmaceutical delivery system or sustained release system selected from the group formed by liposomes, mixed liposomes, oleosomes, niosomes, ethosomes, millicapsules, microcapsules, nanocapsules, nanostructured lipid carriers, sponges, cyclodextrins, vesicles, micelles, mixed micelles of surfactants, surfactant-phospholipid mixed micelles, millispheres, microspheres, nanospheres, liposheres, microemulsions, nanoemulsions, miniparticles, milliparticles, microparticles, nanoparticles and solid lipid nanoparticles, or is adsorbed on a cosmetically or pharmaceutically acceptable solid organic polymer or solid mineral support selected from the group consisting of talc, bentonite, silica, starch, and maltodextrin.

14. The composition according to claim 12, wherein the peptide of general formula (I), its stereoisomers, mixtures thereof and/or its cosmetically or pharmaceutically acceptable salts is in a formulation selected from the group consisting of creams, multiple emulsions, anhydrous compositions, aqueous dispersions, oils, milks, balsams, foams, lotions, gels, cream gels, hydroalcoholic solutions, hydroglycolic solutions, hydrogels, liniments, sera, soaps, shampoos, conditioners, serums, ointments, mousses, pomades, powders, bars, pencils, sprays, aerosols, capsules, gelatin capsules, soft capsules, hard capsules, tablets, sugar coated tablets, granules, chewing gum, solutions, suspensions, emulsions, syrups, elixirs, polysaccharide films, jellies, and gelatins.

15. The composition according to claim 12, wherein the peptide of the general formula (I), its stereoisomers, mixtures thereof and/or its cosmetically or pharmaceutically acceptable salts is incorporated into a product selected from the group consisting of under-eye concealers, make-up foundation, make-up removing lotions, make-up removing milks, eye shadows, lipsticks, lip gloss, lip protectors, and powders.

16. The composition according to claim 12, wherein the peptide of general formula (I), its stereoisomers, mixtures thereof and/or its cosmetically or pharmaceutically acceptable salts, is incorporated into a fabric, a non-woven fabric, or a medical device.

17. The composition according to claim 12, wherein the agent is selected from the group consisting of other PGC-1α modulating agents, other PPARγ modulating agents, agents which increase or reduce the triglyceride content of adipocytes, agents stimulating or delaying adipocyte differentiation, lipolytic agents or agents stimulating lipolysis, anti-cellulite agents, adipogenic agents, agents stimulating adipocyte proliferation, inhibitors of acetylcholine-receptor aggregation, agents inhibiting muscle contraction, anticholinergic agents, elastase inhibiting agents, matrix metalloproteinase inhibiting agents, melanin synthesis stimulating or inhibiting agents, whitening or depigmenting agents, propigmenting agents, self-tanning agents, anti-aging agents, NO-synthase inhibiting agents, 5α-reductase inhibiting agents, lysyl- and/or prolyl hydroxylase inhibiting agents, antioxidants, free radical scavengers and/or agents against atmospheric pollution, reactive carbonyl species scavengers, antiglycation agents, antihistamine agents, antiviral agents, antiparasitic agents, emulsifiers, emollients, organic solvents, liquid propellants, skin conditioners, humectants, substances which retain moisture, alpha-hydroxy acids, beta-hydroxy acids, moisturizers, hydrolytic epidermal enzymes, vitamins, amino acids, proteins, pigments or colorants, dyes, biopolymers, gelling polymers, thickening agents, surfactants, softening agents, emulsifiers, binding agents, preservatives, anti-wrinkle agents, agents able to reduce or treat bags under the eyes, exfoliating agents, desquamating agents, keratolytic agents, antimicrobial agents, antifungal agents, fungistatic agents, bactericidal agents, bacteriostatic agents, agents stimulating the synthesis of dermal or epidermal macromolecules and/or capable of inhibiting or preventing their degradation, collagen synthesis-stimulating agents, elastin synthesis-stimulation agents, decorin synthesis-stimulation agents, laminin synthesis-stimulation agents, defensin synthesis-stimulating agents, chaperone synthesis-stimulating agents, cAMP synthesis-stimulating agents, heat shock proteins, HSP70 synthesis stimulators, heat shock protein synthesis-stimulating agents, aquaporin synthesis stimulating agents, hyaluronic acid synthesis-stimulating agents, fibronectin synthesis-stimulating agents, sirtuin synthesis-stimulating agents, agents stimulating the synthesis of lipids and components of the stratum corneum, ceramides, fatty acids, agents that inhibit collagen degradation, agents that inhibit elastin degradation, agents that inhibit serine proteases, agents stimulating fibroblast proliferation, agents stimulating keratinocyte proliferation, agents stimulating melanocyte proliferation, agents stimulating keratinocyte differentiation, agents that inhibit acetylcholinesterase, skin relaxant agents, glycosaminoglycan synthesis-stimulating agents, antihyperkeratosis agents, comedolytic agents, anti-psoriasis agents, DNA repair agents, DNA protecting agents, stabilizers, anti-itching agents, agents for the treatment and/or care of sensitive skin, firming agents, redensifying agents, restructuring agents, anti-stretch mark agents, binding agents, agents regulating sebum production, antiperspirant agents, agents stimulating healing, coadjuvant healing agents, agents stimulating reepithelialization, coadjuvant reepithelialization agents, cytokine growth factors, calming agents, anti-inflammatory agents, anesthetic agents, agents acting on capillary circulation and/or microcirculation, agents stimulating angiogenesis, agents that inhibit vascular permeability, venotonic agents, agents acting on cell metabolism, agents to improve dermal-epidermal junction, agents inducing hair growth, hair growth inhibiting or retardant agents, fragrances, chelating agents, plant extracts, essential oils, marine extracts, agents obtained from a biofermentation process, mineral salts, cell extracts, sunscreens and organic or mineral photoprotective agents active against ultraviolet A and/or B rays, and mixtures thereof.

* * * * *